US009738694B2

(12) United States Patent
Yeo et al.

(10) Patent No.: US 9,738,694 B2
(45) Date of Patent: Aug. 22, 2017

(54) GENE OF PORCINE ALPHA-S1 CASEIN, A PROMOTER OF THE SAME AND USE THEREOF

(75) Inventors: Myeong Goo Yeo, Seoul (KR); Sung-Jo Kang, Seongnam-si (KR); Jong Deok Ahn, Seoul (KR)

(73) Assignee: CHO-A PHARM. CO., LTD., Seoul (KR)

( * ) Notice: Subject to any disclaimer, the term of this patent is extended or adjusted under 35 U.S.C. 154(b) by 1749 days.

(21) Appl. No.: 12/737,319

(22) PCT Filed: Jun. 29, 2009

(86) PCT No.: PCT/KR2009/003516
§ 371 (c)(1),
(2), (4) Date: Apr. 27, 2011

(87) PCT Pub. No.: WO2010/002160
PCT Pub. Date: Jan. 7, 2010

(65) Prior Publication Data
US 2011/0239314 A1    Sep. 29, 2011

(30) Foreign Application Priority Data
Jun. 30, 2008    (KR) .................... 10-2008-0062765

(51) Int. Cl.
| C12N 15/85 | (2006.01) |
| C12N 15/90 | (2006.01) |
| C12N 5/16 | (2006.01) |
| C07K 14/47 | (2006.01) |
| A01K 67/027 | (2006.01) |
| C07K 14/505 | (2006.01) |

(52) U.S. Cl.
CPC ...... *C07K 14/4732* (2013.01); *A01K 67/0275* (2013.01); *C07K 14/505* (2013.01); *C12N 15/8509* (2013.01); *A01K 2217/072* (2013.01); *A01K 2217/206* (2013.01); *A01K 2227/105* (2013.01); *A01K 2227/108* (2013.01); *A01K 2267/01* (2013.01); *C12N 2830/48* (2013.01)

(58) Field of Classification Search
CPC .. C12N 15/85; C12N 2830/85; C12N 15/907; C12N 2510/00; C12N 2800/107; C12N 5/16
USPC ............................... 435/320.1, 325
See application file for complete search history.

(56) References Cited

U.S. PATENT DOCUMENTS

| 4,873,316 A | 10/1989 | Meade ..................... 530/412 |
| 5,304,489 A | 4/1994 | Rosen ..................... 435/320.1 |
| 5,610,053 A | 3/1997 | Chung ..................... 435/240.1 |
| 5,959,171 A | 9/1999 | Hyttinen et al. .............. 800/200 |
| 5,994,616 A | 11/1999 | Rosen ..................... 800/7 |
| 6,136,597 A | 10/2000 | Hope et al. .................. 435/325 |
| 6,287,863 B1 | 9/2001 | Hodgson ................... 435/455 |
| 6,436,707 B1 | 8/2002 | Zambrowicz et al. ........ 435/455 |
| 6,548,653 B1 | 4/2003 | Young et al. ................ 536/23.4 |
| 7,416,886 B2 | 8/2008 | Kim et al. .................. 536/24.1 |
| 8,420,388 B2 | 4/2013 | Kim et al. .................. 435/320.1 |
| 2004/0133932 A1 | 7/2004 | Cooper et al. ............... 800/4 |
| 2005/0229261 A1 | 10/2005 | Cheng et al. ................ 800/14 |
| 2010/0205680 A1 | 8/2010 | Kim et al. .................. 435/320.1 |
| 2011/0209229 A1 | 8/2011 | Kim et al. .................. 800/7 |

FOREIGN PATENT DOCUMENTS

| EP | 1 557 084 | 7/2005 |
| JP | 1997-298981 | 11/1997 |
| JP | 1998-084981 | 4/1998 |
| JP | 2001-197846 | 7/2001 |
| JP | 2003-521914 | 7/2003 |
| JP | 2005-160359 | 6/2005 |
| JP | 2006-503560 | 2/2006 |
| KR | 10-0145802 | 5/1998 |
| KR | 10-0232640 | 9/1999 |
| KR | 10-0358754 | 10/2002 |
| KR | 10-2004-0039168 | 5/2004 |
| KR | 10-0434729 | 5/2004 |
| KR | 10-2004-0101793 | 12/2004 |
| WO | WO 01/57079 | 8/2001 |
| WO | WO 01/59074 | * 8/2001 |
| WO | WO 03/097818 | 11/2003 |
| WO | WO 2004/042062 | 5/2004 |
| WO | WO 2007/131180 | 11/2007 |
| WO | WO 2008/021136 | 2/2008 |

(Continued)

OTHER PUBLICATIONS

EU025875, Yeo et al., submission Jul. 10, 2007 CHO-A Biotechnology Institute, CHO-A Pharmaceutical Company, 190-1, Sangdaewon 1-dong, Jungwon-gu, Seongnam, Gyeonggi-Do 462-807, Republic of Korea.*
Pollack et al. (1999) J. Immunol. Meth., vol. 231, 147-157.*
Zufferey et al. (1999) J. Virol., vol. 73, 2886-2892.*
U.S. Appl. No. 12/737,318, filed Apr. 21, 2011.
Alexander, L. and C. Beatte, "The sequence of porcine alpha s1-casein cDNA: evidence for protein variants generated by altered RNA splicing," Anim Genet. 23(3):283-288 (1992).
Castro, F. and J. Janne (Ed)., "Mammary Gland Transgenesis: therapeutic protein production", ISBN:3-540-63712-5, published by Springer-Verlag and Landes Bioscience, pp. 91-106 (1998).
Certified English Abstract of Korean Patent No. 10-0145802, Korean Intellectual Property Office, 2 pages.

(Continued)

*Primary Examiner* — Anne Marie S Wehbe
(74) *Attorney, Agent, or Firm* — Dentons US LLP; Stephanie Seidman

(57) ABSTRACT

The present invention relates to a porcine alpha-S1-casein gene, a porcine alpha-S1-casein gene promoter, an expression comprising the same promoter, and a method for the production of a target protein using the same expression vector. The promoter of the present invention facilitates the mammary gland-specific expression of the target protein. Accordingly, an animal transformed with the promoter secretes the target protein in milk at high concentration, and thus can be advantageously used for the production of useful proteins.

12 Claims, 7 Drawing Sheets

(56) References Cited

FOREIGN PATENT DOCUMENTS

| WO | WO 2008/075911 | 6/2008 |
|---|---|---|
| WO | WO 2010/002082 | 1/2010 |

OTHER PUBLICATIONS

Certified English Abstract of Korean Patent No. 10-0434729, Korean Intellectual Property Office, 2 pages.
Certified English Abstract of Korean Patent Publication No. 10-2001-0081456, published Aug. 29, 2001, for Korean Patent No. 10-0358754, Korean Intellectual Property Office, 2 pages.
Certified English Abstract of Korean Patent Publication No. 10-2004-0101793, Korean Intellectual Property Office, 1 page.
Certified English Abstract of Korean Patent No. 10-0232640, Korean Intellectual Property Office, 2 pages.
English Abstract of International Patent Publication No. WO 2003/097818, World Intellectual Property Organization, 1 page.
Cho et al., "Production of transgenic pigs harboring the human erythropoietin (hEPO) gene using somatic cell nuclear transfer," J Reprod Dev 55(2):128-136 (2009).
Genbank Accession No. EU213063 [online], "Sus scrofa beta-casein (csn2) gene, complete cds," Published on Jan. 1, 2008 [retrieved on May 17, 2011] [retrieved from the Internet:<URL:ncbi.nlm.nih.gov/nuccore/EU213063] [9 pages].
Gokana et al., "Chromatographic separation of recombinant human erythropoietin isoforms," Journal of Chromatography 791:109-118 (1997).
Johansen et al., "Increased in vitro and in vivo transgene expression levels mediated through cis-acting elements," J Gene Med 5(12):1080-1089 (2003).
Mastroyiannopoulos et al., "Woodchuck post-transcriptional element induces nuclear export of mytonic dystrophy 3' untranslated region transcripts," EMBO Report 6(5):458-463 (2005).
Mulvihill, D. and P. Fox, "Isolation and characterization of porcine beta-casein," Biochim Biophys Acta. 578(2):317-324 (1979).
Parekh et al., "N-glycosylation and in vitro enzymatic activity of human recombinant tissue plasminogen activator expressed in Chinese hamster ovary cells and a murine cell line," Biochemistry 28(19):7670-7679 (1989).
Park et al., "Production of transgenic pig harboring tissue-type plasminogen activator gene with bovine-beta-casein promoter," Division of Animal Biotechnology, pp. 190 (2004). Abstract.
Park et al., "Recombinant human erythropoietin produced in milk of transgenic pigs," J Biotechnol(3):362-371 (2006).
Prather et al., "In vitro development of embryos from Sinclair miniature pigs: a preliminary report," Theriogenology 43(6):1001-1007 (1995).
Roberts et al., "Cloning of the goat beta-casein-encodeing gene and expression in transgenic mice," Gene 121(2):255-262 (1992).
Schmitt-Ney et al., "Beta-casein gene promoter activity is regulated by the hormone-mediated relief of transcriptional repression and a mammary-gland-specific nuclear factor," Molecular and Cellular Biology 11(7):3745-3755 (1991).
Ziomek, C., "Commercialization of proteins produced in the mammary gland," Theriogenology 49(1):139-144 (1998).
Zufferey et al.,"Woodchuck hepatitis virus posttranscrtiptional regulatory element enhances expression of transgenes delivered by retroviral vectors," J Virol 73(4):2886-2892 (1999).
Letter/Written Disclosure of the Information Disclosure Statement for the above referenced application, mailed on Sep. 8, 2011, 2 pages.
International Search Report, issued Mar. 25, 2010, for International Application No. PCT/KR2009/003516, 3 pages.
Written Opinion, issued Mar. 25, 2010, for International Application No. PCT/KR2009/003516, 6 pages.
International Preliminary Report on Patentability, issued Feb. 8, 2011, for International Application No. PCT/KR2009/003516, 7 pages.
Letter/Written Disclosure of the Supplemental Information Disclosure Statement for the above-referenced application, mailed on May 25, 2012, 2 pages.
Tong et al., "Production of p53 gene knockout rats by homologous recombination in embryonic stem cells," Nature 467(7312):211-213 (2010).
Extended European Search Report, mailed Nov. 24, 2011, in connection with corresponding European Patent No. 09773696.1, 6 pages.
Office Action, issued Mar. 13, 2012 in connection with corresponding Austrailian Patent Application No. 2009266603, 2 pages.
Letter/Written Disclosure of the Information Disclosure Statement for the above-referenced application, mailed on Apr. 4, 2013, 2 pages.
de Jong, "Sus scrofa genomic clone CH242-240J23, genomic survey," Published on Nov. 7, 2005 [online][retrieved on Aug. 5, 2012] Retrieved from:<URL:ncbi.nlm.nih.gov/nucgss/ct146582.1 AF177422 [1 page].
English abstract of Japanese Patent Publication No. JP1997-298981, Japanese Patent Office, 1 page.
English abstract of Japanese Patent Publication No. JP1998-084981, Japanese Patent Office, 1 page.
English abstract of Japanese Patent Publication No. JP2001-197846, Japanese Patent Office, 1 page.
English abstract of Japanese Patent Publication No. JP2005-160359, Espacenet, 1 page.
Genbank Accession No. AY452035, "Sus scrofa beta casein gene, promoter region, exon 1, and partial sequence," Published on Sep. 5, 2008 [online][retrieved on Apr. 27, 2012] Retrieved from:<URL:ncbi.nlm.nih.gov/nucleotide/42525316?report=genbank&log$=nucltop&blast_rank=-4&RID=TNCAAN5701N >, 4 pages.
Kwon et al., "Dynamic control of oligosaccharide modification in the mammary gland: linking recombinant human erythropoietin; functional analysis of transgenic mouse milk-derived hEPO," Transgenic Res, 15(1):37-55 (2006).
Meade et al., "Bovine alpha S1-casein gene sequences direct high level expression of active human urokinase in mouse milk," Biotechnology (N Y) 8(5):443-446 (1990).
NCBI Accession No. NW_003535482, "Sus scrofa breed mixed chromosome 8 genomic scaffold, Sscrofa10.2," Published on Oct. 11, 2011 [online][retrieved on Aug. 5, 2012] Retrieved from:<URL:ncbi.nlm.nih.gov/nuccore/NW_003300496.1?report=genbank>, [5 pages].
NCBI BLAST:Nucleotide Sequence, [online][retrieved on Aug. 5, 2012] Retrieved from:<URL:blast.ncbi.nlm.nih.gov/Blast.cgi >, [3 pages].
NCBI Accession No. CU929598, "Sus scrofa chromosome 8 clone CH242-240J23, Working Draft Sequence, 22 unordered pieces," Published on Sep. 24, 2008 [online][retrieved on Aug. 5, 2012] Retrieved from:<URL:ncbi.nlm.nih.gov/nuccore/206591689 >, [39 pages].
Toledo et al., "High expression level of recombinant human erythropoietin in the milk of non-transgenic goats," J Biotech 123(2):222-235 (2006).
Wikipedia entry for "Promoter (genetics)," Last modified on May 18, 2012 [online][retrieved on Jun. 11, 2012] Retrieved from:<URL:en.wikipedia.org/wiki/Promoter_(genetics) [5 pages].
Yeo et al., submission Jul. 10, 2007 CHO-A Biotechnology Institute, CHO-A Pharmaceutical Company, 190-1, Sangdaewon 1-dong, Jungwon-gu, Seongnam, Gyeonggi-Do 462-807, Republic of Korea 1 pg.
International Search Report, issued Aug. 14, 2009, in connection with International Application No. PCT/KR2008/007823, 3 pages.
Written Opinion of the International Search Authority, issued Aug. 14, 2009, in connection with International Application No. PCT/KR2008/007823, 3 pages.
Extended European Search Report, issued Dec. 23, 2010, in connection with European Patent Application No. EP 07793416, 8 pages.
International Preliminary Report on Patentability, issued Jan. 5, 2011, in connection with International Application No. PCT/KR2008/007823, 4 pages.

(56) References Cited

OTHER PUBLICATIONS

Restriction Requirement, issued Jan. 18, 2011, in connection with U.S. Appl. No. 12/733,087, 31 pages.
Examiner's Report, issued Feb. 24, 2012, in connection with Australian Patent Application No. 2008359017, 2 pages.
Restriction Requirement, issued May 1, 2012, in connection with U.S. Appl. No. 12/737,318, 11 pages.
Response to Restriction Requirement (Election and Preliminary Amendment), issued May 1, 2012, in connection with U.S. Appl. No. 12/737,318, 4 pages.
Response to Extended European Search Report, submitted Jun. 20, 2012, in connection with corresponding European Patent Application No. 09773696.1, 14 pages.
Examination Report, issued Jul. 24, 2012, in connection with corresponding European Patent Application No. 09773696.1, 5 pages.
Office Action, issued Aug. 8, 2012, in connection with U.S. Appl. No. 12/737,318, 22 pages.
Response to Examiner's report, submitted Aug. 16, 2012, in connection with corresponding Austrailian Patent Application No. 2009266603, 17 pages.
Response to Examiner's report, submitted Aug. 21, 2012, in connection with Australian Patent Application No. 2008359017, 16 pages.
Examiner's Report, issued Sep. 3, 2012, in connection with Australian Patent Application No. 2008359017, 2 pages.
Examiner's Report, issued Sep. 3, 2012, in connection with corresponding Australian Patent Application No. 2009266603, 2 pages.
Response to Examination Report, submitted Nov. 23, 2012, in connection with corresponding European Patent Application No. 09773696.1, 15 pages.
Response to Examiner's report, submitted Dec. 3, 2012, in connection with Australian Patent Application No. 2008359017, 6 pages.
Response to Examiner's report, submitted Dec. 6, 2012, in connection with corresponding Austrailian Patent Application No. 2009266603, 6 pages.
Response to Office Action, submitted Dec. 7, 2012, in connection with U.S. Appl. No. 12/737,318 , 4 pages.
Office Action, issued Dec. 18, 2012, in connection with corresponding Japanese Patent Application No. 2011-516140, 9 pages.
Examination Report, issued Mar. 1, 2013, in connection with corresponding European Patent Application No. 09773696.1, 4 pages.
Letter/Written Disclosure of the Information Disclosure Statement for the above-referenced application, mailed on Dec. 16, 2013, 2013, 2 pages.
Cho-A Pharm. Website, Process of EPO Production, [online] [retrieved Oct. 8, 2013] retrieved from the internet <URL:choa.co.kr/eng/research/epo02.asp>, 1 page.
Cho-A Pharm. Website, Research History, [online] [retrieved Oct. 8, 2013] retrieved from the internet <URL:choa.co.kr/eng/research/epo04.asp>, 2 pages.
Cho-A Pharm. Website, Research Performance, [online] [retrieved Oct. 8, 2013] retrieved from the internet <URL:choa.co.kr/eng/research/epo03.asp>, 1 page.
Cho-A Pharm. Website, Our Research Plan, [online] [retrieved Oct. 8, 2013] retrieved from the Internet <URL:choa.co.kr/eng/research/epo05.asp>, 1 page.
NCBI Reference Sequence NW_003535482.2,"Sus scrofa breed mixed chromosome 8 genomic scaffold, Sscrofa10.2," Published on Nov. 5, 2010 [online][retrieved on Aug. 5, 2012] Retrieved from:URL:ncbi.nlm.nih.gov/nucleotide/347616012?report=genbank&log$=nucltop&blast_rank=1&RID=1Y1CR2D301N, 4 pages.
NCBI Reference Sequence: NW_003535482.1, "Sus scrofa breed mixed chromosome 8 genomic scaffold, Sscrofa10," Published on Nov. 5, 2010 [online][retrieved on Aug. 5, 2012]. Retrieved from the Internet:<URL:ncbi.nlm.nih.gov/nuccore/333785014 >, 5 pages.
Notice of Acceptance, issued Jan. 7, 2013, in connection with Australian Patent Application No. 2008359017, 5 pages.
Notice of Acceptance, issued Jan. 9, 2013, in connection with corresponding Austrailian Patent Application No. 2009266603, 6 pages.
Response to Examination Report, submitted Jun. 28, 2013, in connection with corresponding European Patent Application No. 09773696.1, 80 pages.
Examination Report, issued Jul. 22, 2013, in connection with corresponding European Patent Application No. 09773696.1, 4 pages.
Response to to Examination Report, submitted Nov. 22, 2013, in connection with European Patent Application No. 09773696.1, 20 pages.
Invitation persuant to Article 94(3) and Rule 71(1), issued Dec. 6, 2013, in connection with European Patent Application No. 09773696.1, 3 pages.
Letter/Written Disclosure of the Supplemental Information Disclosure Statement for the above-referenced application, mailed on Jul. 30, 2015, 2 pages.
Decision to grant European patent pursuant 97(1) EPC, issued on Jul. 9, 2015, in connection with European Patent Application No. 09773696.1, 1 page.
Letter/Written Disclosure of the Supplemental Information Disclosure Statement for the above-referenced application, filed herewith Aug. 29, 2016, 2 pages.
Examiner's Report, issued Dec. 18, 2013, in connection with Canadian Patent Application No. 2,729,625, 2 pages.
Response to Examiner's Report, submitted Apr. 2, 2014, in connection with Canadian Patent Application No. 2,729,625, 8 pages.
Examiner's Report, issued Mar. 3, 2015, in connection with Canadian Patent Application No. 2,729,625, 3 pages.
Response to Examiner's Report, submitted Sep. 3, 2015, in connection Canadian Patent Application No. 2,729,625, 7 pages.

\* cited by examiner

TG 1 EPO-WPRE

V   1-1   1-2   1-3   1-4   1-5   1-6   V   N

TG 1 WPRE-alpha S1

V   1-1   1-2   1-3   1-4   1-5   1-6   V   N

Western blot assay

```
                        SEQUENCE LISTING

<160> NUMBER OF SEQ ID NOS: 95

<210> SEQ ID NO 1
<211> LENGTH: 33247
<212> TYPE: DNA
<213> ORGANISM: Sus scrofa
<220> FEATURE:
<221> NAME/KEY: gene
<222> LOCATION: (1)..(33247)
<223> OTHER INFORMATION: gene of porcine alpah S1 casein

<400> SEQUENCE: 1
aggattacaa gattgctgtt ggataatgct ggatataaga aattgcatat ctttattctg      60
taacctcagc agaagtattg tgaagtttgt ctttagcaat gctgagatgt tctttactag     120 ttcttttac tctatttctc ggggcttaaa tctttcatct tatatgcatg ttaggcattc     180
tccaccagct aggatgttat ttcctccatc acctatccga agattcgaca ccttgaatac     240
attgcttttg ttgagtaaaa gaataagcag tatgatatat tagaaagagc acaggctctg     300
atgttgggag atctgagtca tcatttactc attagctggt gcaagcattt tgtatggaaa     360
ttaatttact tattaatttt attactttta tttttacttt tatttttgc catttctagg     420 gccgctcccg cagcatatgg aagttcccag gctacgggtc taattggagc tgtagctgcc     480
agcctatgcc agatccttag caacgcagga tccaagtcgc gtctgcaaac tacaccacag     540
ctcacggcaa caccagatcc ttaacccatt gaggaaggtc agggattgaa cctgcaacct     600
catggttcct agttggattc gttaagcact gtgccacaat gggaactcct taatttactt     660
aatttataaa agtttagttt ccttatctac aaaagggaaa ataatgactt gtttctctac     720
attacatgat tcttataagg agtagttgtg aaaataatta taagaagact ttagaaatta     780
taaagaagat tataaattga caaagaaatg aatctatttc attctgctga tggatgactt     840
attaatctat ctggtaaact gtggttctga tggccaataa tgcctgttaa atacattgta     900
tcctcataat aatattgtta aacagggact gccaatgatt ggaccccagg aaagtttatc     960
agtcatgaaa accacatttt gtcaagtcag aagaactatt actgataaga aaaaaatctc    1020
tttacccacc aaattacagt ctttcagaaa gaaatcacta ggtgagattt agttaaccaa    1080
gttaaatttt agcccagttt tcccagatgt cttgagtagg tgaaagcttc cttcatggca    1140
agatgaatga attttggtt ggaggtaaga ggcaggtagt ggtcttggca cgacatagac    1200
agataaactg ttacttgtga gatatcatac ctacaaaaag aatatagggt tggataagga    1260
gatgctttat tgtagacatt gctataaagg taaacacttt catggaaata caattcagca    1320
gttttagcat ctttgttttt gccatatgtg ttacatattt ttacaatttt catatgcttt    1380
taatttttta aaaggtattt tacatacaaa ctttcattat tgggtatttt aaaagagaag    1440
actgtgtatt acattttcaa atctttcagt ttctagctac tcaaagtgtg ctgcatgggt    1500
caccagcagt gacatcacct tagagcttat taaaaattca ttagctcctg gagttcccat    1560
cgtgatgcag cagaaacaaa tttgactagg aaccatgagg ttgcaggttc aatccctgcc    1620
tccctcagtg ggttaaaaat ccgacattac tgtgagctgt ggtataggtc acagacccgg    1680
```

```
ctgggatctg gtgttgctgt gactctagca tagtccagca gaaacagctc tgattagacc    1740
tctagcctgg aaaccttcat atgccgctgg tgccctaaaa ggacaaaaga gaaaaaaaaa    1800
aatacgttag ttcaggacac acctcagatt tactaaatct gaatctgaat tttaacataa    1860
tatcctggtg attcataagc acattaaagc attgttgtag ttcattgttc tgtgagaaca    1920
tcaaatagta taggatttca tcaataaaat tcagaagttc tttctattcc cctctcatat    1980
tccatcccaa gctttcttca gttgtggtca ctaataaaaa ttttgccttc acacacacac    2040
acacacacac acacacacac acataaggtc tttttagggc tgcacccatg gcatatggag    2100
tttcccaggc taagggtcaa atcagagctg tggccgctgg cctatgtcac tgccacaaca    2160
acaccagatc tgaattgcat ctgtaactta caccacagct catggcaata ccgatcctta    2220
acccactgag caaggccagg gatcaatcct gcatcttcat gtttactagt cagatttgtt    2280
tctgctgagc catgacagga accctgcctt tacccttta tacatttta atgcacatac      2340 aatatacaag tatgattcaa gacttctcga aagttaacaa atccacaaga taggaaaatg    2400
atttgggcac aaaataatta gttgaggttt tttttaaaaa aaaaattcta ataatgatcg    2460
ttttaaatga gcacttactt tgtctcaggc tctcttctaa gtgtgtgatc taatttttc     2520 ctctcgatca cacaggaagt ggatgtcctt aaacagatgt ggacactgag gcacagtgat    2580
tttgcaagat taccctgctg gtcattgaga gccagaaatt aaatttacaa tttgacctca    2640
aaatcttgtc ttgcaacaac tacatcatgt gtttcattta agatcttctg agacctattg    2700
atacagcact aaaaaggata ttgttctaaa cacaaacata aaatcaagca taagttccat    2760
atttccaggg atatcacata ccacaccta ccgaaagaac tctattttag ttctagatgc      2820
caagattcca cttgtgcaat acttaagagt aatgattcgg ggggggggga tgcactgggg    2880
gtttgggatg gaaatgctat aaaactgggt tgtgatgata attgtacaac tataaatgta    2940
ataaattcat tgagaaatat agaaaaaaat aaaataaaat cccccctccc aaaaaagaa     3000 ttcactgtgg atcctctctt agattccaaa cagtatgtgg gtttctagag agaaacaaag    3060
atgtctttca tattctcagt aaatttcctt ctggaagttt cactgttaaa agacattttc    3120
ctagaagact caccagtcat aaacccaaat attcctggga gaatgctgac aaactagctt    3180
tgaaattcat gttctgaatt attgactgtc tcatacagaa tgagttctcc aatgaggttt    3240
aatgtggacc agaatatgta gcaacagtac acaaaacttt gcagagtaaa gtttacctcc    3300
tgactcacag ttcccttccc tccaaactcg aagtctattg ctaatgtttc ctctccttt     3360 tgtgctagtt tttctaagaa gtatgaatct aggaaagaat gttccaata ttgaaacttg      3420 aaacacaaga aagctttcag cttggttgtc ccttatctga cctatttcca cttcactga     3480 cttagggatt ctgttggatt tcaaaaccg tcgtgatagt actagagtag ctttgccttt     3540
gtgtgccaaa gatagttttg gtttatggct gtcgttttgt tatgattatt acaaagactc    3600
tcccatactc ataagtgttc catgttgaat gatcagttat atgttcatcc tacatatgac    3660
tattacatca gaaaatcgct attcaggtaa aatttcatt ctttctttac tcacaggaca     3720
aaggcctgtt taactacaaa tcatctaaat atgtgtctca aatgtgaact gtgattttc     3780 ttttttagtg gtttgaactg aacaatttt ttttaattta tttttttccc actgtaaagc     3840
aaggggatca agttatcctt acatgtatac atttttattc cccacccttt gttctgttgc    3900
aatatgagta tctagacata gttctcaatg ctactcagta ggatctcctt gtaaatctac    3960
tctaagttgt gtctgatcag cccaagctcc caatccctcc cactccctcc ctctcccatc    4020
aggcagccac aagtctattt tccaagtcca tgatttttctt ttctgtggaa gggctcattt    4080
```

```
gtgccttata taagattcca ggtatcagtg atatatcatt tggtatttgt ctttctcttt    4140
ctgacttact tcactcagta tgagagtctc tagttccatc catgttgctg caaatggcat    4200
tatgccattc ttttatggc tgagtagtat tccattgtgt gtatatacta catcttccgg    4260
atccaatcat ctgttgatgg acatttgggt tgtttccatg tcctggctat tgtgaataga    4320
gctgcaatga acatgtgggt gcatgtgtct ctttcaaggt aagttttgtc tggatatatg    4380
cccaagagtg ggattgcagg gtcacatggt agttctatgt gtagatttct aaggtatctc    4440
caaactgttc tctatagtgg ctgtaccagc ttacattcac accaacagtg caggagggtt    4500
cccttttctc caccccccccc ccagcatttg ttatttgtgg acttatcaat gatggccatt    4560
ctgactggtg tgaggtggta tctcatggta gttttgtttg catttctcta ataatcaggg    4620
atgttgagca ttttttcatg tgcttgttgg ccatctgtac atcttccttt gagaaatgtc    4680
tattcaggtc ttttgcccat ttttccattg ggttggttgg ctttttttgct gttgagttgt    4740 ataagttgct tgtatattct agagattaag cccttgtcca ttgcatcatt tgaagctatt    4800
ttctcccatt ctgtaagttg tcttttttgtt ttcctttggg tttcctttgc tgtgcaaaag    4860
cttgtcagtt tgatgaggtc ccattggttt atttttgctc ttatttctgt tgctttggga    4920
gattgacctg agaaaatatt catgatgttg atgtcagaga gtattttgcc aatgttctct    4980
tccaggagtt tgatggtgtc ttgtcttata tttaagtctt tcagccattt tgagtttatt    5040
tttgtgcatg gtgtgagagt gtgtaccagt ttcgttaatt ttcatgcagc tgtccaggtt    5100
tcccagcaat gcttgctgaa tagactttct ttttcccatt ttatgttctt gcctcctttg    5160
tcaaagatta attgaccata gttgtcaaag tttatttctg ggttctctat tctgttccat    5220
tggtctgtct gttttgatag cagtggcatg ttgttttgat gactgtggct ttgtaatatt    5280
ttttgaagtc tgggaaagtt atgcctcctg cttgattttt gtttctcagg attgctttgg    5340
caattctgag tcttttgtgg ttccatataa aattttggat tgtttgttct agttctgtga    5400
aaaacgtcat cggtaatttg atagggattg cattgaatct gtatattact ttgggtagta    5460
tggccatttt tacattattg attttttccaa tccatgaaca cggaatatct ttccatttct    5520
ttacatcttc tttgatttct ttgattatag ttttatatga actgaacaac tttaagtgat    5580
aaaagcaaaa ggaaaaatac gaatataaag caaattgaca taagctaaaa ttttgcagga    5640
tttgacgttg tataaatcta caatgaatat gtttgctcga attacagtga acagtcatat    5700
tttacaagta taagaatgat ttatttcaaa atacaaactt aattaactat attctatatc    5760
taataagcaa agtgaagatt gatccttatc cataggtact agaaaaatct gtgttttgag    5820
tttatgagaa ttcctatggt ggatacatgt gttcactaag agttggcttg tctttaaaag    5880
ttctgattgt tcttctttga tggcaagcct tattattatc aaatctaaga ctccagtctc    5940
agttttttga gtctctattt ttggactatc aggaatatta aaattatcag cttttttgtat    6000 gtgaattacc cactatagta tgagactaca gattttgtct tacccaactt ttatttcccc    6060
tgtgtcttgt ctcatttctt cacctctgta aataaataat gtaagaatga gtaaacaaat    6120
gaggatacag tagctttaca caacttacag tatgatcctg aattggaaat aaaataagtc    6180
agttatcctg gatgcattct caggaaaaga caagagccgg gtattgtaag gcagtggaga    6240
atacttgttc tcagccccctt ggataaatca gagtaaatag aaaatactag tgctttttg    6300 acattgatgt aatgcagtca gcaaggacga tactatccaa agagaagttt aacatggaaa    6360
actatagcct tgtctatccc cagtatggaa agcctgagcc actgcgaaat ttcttttaac    6420
```

```
cccaaataat gttcctacca tatgactgta aattggctgt gaatatcact atggatttat    6480
tattttattt ttaaatttt ttggtctttt ttcttttag ggctgcaccc atggcatatg      6540
gaggttccca ggctaggggt cgaattggag ttgtagctgc cagcctacac cacagccaca    6600
gcaatgccag atctgagctg tgtctgcaac ttacaccaca gctcatggca acaccagatc    6660
attgacccct tgagtgaggc cagggatcga acctgcaacc tcatggttcc tagtcagatt    6720
catttccct gcgccacaat gagaattcca gattttttt aaatatatag tgtgatacct      6780
ttctgtaaac aagcagtcac aatcaacaat ttttaaatc cagctctatg tatagatatt     6840
ttattcagca tgcaattttt ttcctaaaat taacaatgcc agttaattct aggattatat    6900
ttcaggactg gaaagaaagt ttttttttcc ttttatttac ttactttaaa aggtggaaaa    6960
ttggagttat ggttgatttt tgggggggg ggagtattta aaaattgtat tcttaaataa     7020
aaattattct tgaataatta ttttaatta agaaatctaa caattaaatt aatgaatact     7080
atcacaacac atatacccaa aataaagcaa gcagaaaatt atttggtgta gttaaaatac    7140
taccaaagtt tataaggcaa ttgtattttc ttttggtta aaaaaaagat cagatcacat     7200
ataaggtaac ttactccaca aggtaactta cttagaatac ttagaataaa tacttagaag    7260
acttagaata aataataggg aataaataga gttttaaaag gtgaaataga tgatgaaatc    7320
ttctcatggt ctagtacaat tataaaaatt aaaatttt gatgatttta ttttgtctca     7380
agaatttccc ttcaggtat tgacttttc aaaagctgta aaggaaattt tattgctata     7440
ttaatctttc caattatcca tttaacttaa aaagcatgtt cttataataa ccataaaatat    7500
ggaatttta tgtatcttaa ttttgaataa tgtcattcca tttcctgtat aatttggtat     7560
catagcatga atcactcctt tgttgaaaac tctcctcaga atttcttggg agaaaaattg    7620
gacagaaaat taatttcctc tttgagagaa ttcttagaat ttaaatgaca ctattggttg    7680
aactgaaacc acaaaattag cattttacta atcactaggt ttaaatattt gtgaaacaaa    7740
gagatctgcc accatcttga tcatcagctc agcttgcttc ttctttccgg tcttgggttc    7800
aaggtatttc atttacatat agcaaaatgt gatatattat gatttcaatc tgtctaatt    7860
ttcactcctc actaaaaaat atgcactggt aacttttctg tgtgattcca aatattgata    7920
ccttttaatg atatactggt ggcttaaaaa tgcatttgca aatgtcgatg ccatctatct    7980
cagagcttta gttgaaaaat aatagttta taaagaccaa atttttttg ccaaatttta    8040
tgaaaactta ttatgtgaaa taatttataa tcttttaaa gatcatagtg aggatcattt     8100
ctggtagaat atttcaagac cattttatt ccatgtcatt aggttaataa aattaattct    8160
ataaaggata tgtcaatgat atacacagat ataaatgact acttttaaa agatggttag     8220
atttggatat ttgaaaaaat gcaaatgaat aaaaccagta aactcatttt ggatttataa    8280
atatgtcttc cttacaaatg cagttagatt ctacaatatg tagactgaaa cagtatgtat    8340
aaaataagct gattagtttg ttggctaatg tataaacaaa ttgcatgtat attatgactt    8400
tccttttccta atttctctgg aaaccagttt cccaggacat aagttctaag tatctctggg    8460
ttcttgtaat ttgatggaac tctagaagtc acacatgata agacatcaga atcttatgat    8520
tctgctcaat gaagtcgtct ttatgcagtc atgtcatgga tatagcaacg tagaaaaaca    8580
taacataata gctagacttt aaaaaaaaat tgatggaggt taaatgtttc tacataatat    8640
gcaccaacag tgttttttcc aaagacgctg aaaaagcagg attctctaac atagacctag    8700
aaaaacacct tcaaaaaatt gcagatagg agttcccgtt gtggctcagt ggttaacaaa     8760
tccgactagg aaccatgagg ttgcaggttc aatccctggc cttgctcagt gggttaaagg    8820
```

```
atctggcatt gatgtgagct gtggtgtagg tcgaagacgt ggcttggatc ccacgttgct    8880
gtggctctgg tgtaggctgg tggctacagc tctgattcaa cccctagcct gggaacctcc    8940
acatgccgtg ggagcggccc aaaaaaaggc aaaaagacca aaaaaaaatt ttttttcag     9000 ataaaattaa atgccagttc cctgtgcctt ttagtttatt atcaattttt agcaaatctg    9060
atggtctaag aggaaatatt taaaataatt aattgtagta ttcttaaatt tagtagtatt    9120
taaatattaa tgtttatgta ttcctctgac aaacccctat taccacttca aggatcaaat    9180
gttttgtttt agagggtgat actggtgttt cttatctcat ataagcacta agcaagataa    9240
tttgaatgat aaattttctc tgtgagtaaa ttttctgtca gacctaaatt tttattttgt    9300
tttcttatat aggtgttgac aaccatgaaa cttctcatct ttatctgtct tgcagctgtt    9360
gcccttgcca ggcctgtgag tatggtagag aatttagagg cttctagatt cttgattgaa    9420
attacctgat atcaaacaca agaaactgag gataataatc ttaaaagtat tgaatgatct    9480
ctaattacct tttgaagcct tgatattaaa actgtagaaa tccttcacat cttgatcatt    9540
attacatagt tcattcaaag tcatcactcc aaataaaatc tgagttgaaa tataaatgcc    9600
tcacagtaaa aaataaaaa caaaaaatga aagaaaaga aaaggaata atgtattaa         9660 caacatagta aatagaatca atgagtgtta ttacgctctt tgcctgggtc caataaagaa    9720
ttagcatata tttaaacata caagtccatg attttttctg tggaagggct catttgtgcc    9780
ttatataaga ttccaggtat cagtgatata tcatttggta tttgtctttc tctttctgac    9840
ttacttcact cagtatgaga gtcttagttc catccatgtt gctgcaaatg gcattatgcc    9900
attcttttta tggctgagta gtattccatt gtgtgtatat actacatctt ccgaatccaa    9960
tcatctgttg atggacattt gggttgtttc catgtcctgg ctattgtgaa tagagctgca   10020
atgaacatgt gggtgcatgt gtctctttca aggtaagttt tgtctggata tatgcccaag   10080
agtgggattg cagggtcaca tggtagttct atgtgtagat ttctaaggta tctccaaact   10140
gttctctata gtggctgtac cagcttacat tcacaccaac agtgcaggag ggttcccttt   10200
tctccacccc cccccagcat ttgttatttg tggacttatc aatgatggcc attctgactg   10260
gtgtgaggtg gtatcttgtg gtagttttga tttgcatttc tctaataatc agggatgtt    10320 agcattttt catgtgcttg ttggccatct gtacatcttc ctttgagaaa gtctattcag   10380
gtcttttgcc catttttcca ttgggggtgtt ggctttttg ctgttgagtt gtaaagttg     10440 tttgtatatt ttagagatta agcccttgtc agttgcatcg tttgaaacta ttttctccca   10500
ttctgtaagt tgtctttttg ttttcttttg ggtttccttt gctgtgcaaa agcttgtcag   10560
tttgatgagg tcccattggt ttattttgc tcttatttct gttgctttgg gagattgacc    10620
tgagaaaata ttcatgatgt tgatgtcaga gagtattttg ccaatgttct cttccaggag   10680
tttgatggtg tcttgtctta tatttaagtc tttcagccat tttgagttta tttttgtgca   10740
tggtgtgaga gtgtgtacca gtttcgttaa ttttcatgca gctgtccagg tttcccagca   10800
atgcttgctg aatagacttt cttttttccca ttttatgttc ttgcctcctt tgtcaaagat   10860
taattgaacc tttccataga aaagaaaatc atgaatttgg agaataaact tgtggttgcc   10920
aaaggggagg gagagggagt ggtgtggttg aggagcttgg ggttaataga tataaactat   10980
tgcctttgga atggattagc aatgagaccc tgctgtgtag cactgggaac tatgtccagt   11040
cacttatgat ggagcatgat aatgtgcgaa aatagaatgt gtacatgtat gtgtaactgg   11100
gtccccatgc tgtacagtag aaaaaaaatg tgttgagaaa ataactatta caaaaatgag   11160
```

```
aattatgaaa taaataaata aataaacaaa catacatgtc caatatttc ttaccaaata    11220 taacagaatg ccgcctattg cagtgtatcc tacttttgga acctaagtca aaccctcaca    11280
tgagatgact catatcaacc aatatttccc aaggtgtaga aaactgagtt attctgctga    11340
ttcagagatt taattattat ggtccttgta gacaaggaaa ctaggtaata taaattaaaa    11400
tcacttttct tctcaaaaaa aaaaaagatt cagttactta tgtagagcaa aaattattct    11460
gttcccttgt gatatatagc tagcaaagat ggaagggata aactggaatt gcttgacaaa    11520
gaaaccatcc agataaaata ataatcttgg atatttgggc attgtaatta ttaaatatag    11580
gtgtaaaatt ttttggaatt ctgagatatt ctatgatgag actcctattt tctaaatttt    11640
tgtttggata atgcaggatc actaataacc taactttcct tttttttttt ttttttttt    11700 ttgctttta gggccatacc cacagcatat ggaggttctc aggctaggag tcaaatcaga    11760
gctgcagctg gcctaaccac agccacagca acattggaat cagatccgag ctgtgtctgt    11820
gatgtacacc acagctcaca gcaatgctgg atccttaacc cactgagtga gaccagggat    11880
caaacccaca tccccataaa cactagttag ctttgttact ccagagccac tatgggaact    11940 ccaaccaac ctgttagaca ctagagcttt ttctatgcta caccttaagc accaatagga    12000
agaaaatcta tgatagcaag ttacaagaaa aaggatccaa cttttcaga aaagtgtcac    12060 tgttagtctt tttacaaaag aaatgggtat agtttcccca gcaaacagat tctataattc    12120
tattccaaga aaacatcatt tttaatgcta ccatttaaca aacataaatc ttgttcccac    12180
agttcaaatg tagattgagt taaatttta tataattaac tgattataaa aataaaatcc    12240
agaaaatgtt taatgaagaa aagtatatat tttgtttcaa aaattcataa tagttatttt    12300
tagaactacc atgtaatata aatagttcag aaaaattaaa tttatcattc tggatcaaga    12360
caaattaatt ttttttttca gtctttttac acatttttct cagttctcca tcatacccca    12420
atgacaggaa atcatttact tttctgtgat ttttatcaag aaaataacca ttttttttct    12480
tcccagggaa acttggggtc agatgaattt agctattaaa atacacatca ttcttaaata    12540
gcaaatgtta catttacagt attctatttg ttttgtgata ttattatcat attttgattg    12600
cattttgttt tcttttgtt tgttttttaaa ttcttgcatt gttttcaca gaaacctcct    12660 ctcaggcatc aggaacacct tcaggtgagt gctattctct gtgttctaag aactcactaa    12720
ttgtgggact gagcaatgat atattggtca tacatagact ctggtcctac tccacccttc    12780
tctataagac attcagtttc acattcaccg aggaataagg gcttcagttc aagtattaaa    12840
ctggttattg atctagtctc acaaaccta gagagaaggg tatgggact tacataaata    12900 tttaattaat atttaacatg gtttattaa tataatgttg cttcttcca tctcttttgc    12960 atgtacccaa atatatgatt gacaatttgc tctcatttta cacactgaat cttaaattag    13020
atacctccac caagagcctt tacaagagtg attaatcctc cactctgtcc actaattgaa    13080
ttaataccat tttatttatt tttcattctt tacagaacga gccagacagc agagaggtaa    13140
agttctttct ttccctcgac aaatctctcc ttcagttctc catgatgaat gttaaatatc    13200
ttctttgttt caatttttat ttgtctttgg tactcaggta cttggagtac tttctcaatt    13260
ctttgctttc attacactcc ttttcagttc ctcctttgac acctgacgag tattaagagt    13320
atgaacttac taaacctcta ggcttggtaa agaaggaacc aaaaataatg actcctttag    13380
attttaaaat tagattataa aactaaaact aattatctcc taacttacct aagaaatatt    13440
ttggtttgcc taagtaaatg gggaagttgt gttcaaatgg aaaaatattc tccttttctg    13500
aatcatgttt ataattcaca attgaatttc tacaggaact cttcaaagaa agaaagtttc    13560
```

```
tcaggtttcc tgaggtggta agcattatcc acttcttaaa tgacaaatat attttttccgg    13620 aaaaaatcaa tttaattttt tgtttataaa tgtgttttc acttgatttg atcaaacttt      13680
ttcttcattt tccaaagctc ccacaaataa tattgaaatc agatatgcaa atattaggag     13740
ttgctttaaa tattaaagaa ctgctttaaa tattaacttg tgcctctata tctgactctt     13800
tgcaaaacac aaacgctttt ttttaatatc ctatgtagag ttttaaaatg tccatgatta    13860
tgatgatgga atgttctcta tctctaaata ataccctcata tgtgttgtgt tttctataat   13920
tttgtgactg aattgtcaca taggaaaaaa aatagaaatt ttacttcaag accactgttt     13980
agaagatttg atatgaaccc atctttgtct aaatgatttt taacataacc tttctttttt    14040
tttgtagcct ttattaagtc agttcagaca ggtaagaaat tctccaccag atatacagta    14100
gagttaacaa gggaagcaat cttggtttct gtctagtaag tgctgtggtg tgggtgttgt    14160
gccaattctt tattgccttt ttatggaaat aaacactaga cttaactgaa tcaggcagat    14220
gaaatcaaga gaactcagaa ctacgtcata ataaggtga aagataatag caacaacatt     14280
tagtggaaca aaattttaaa tgattttaag tgcacattta catactgata gcttaaacaa    14340
agaaagctca gtgaggcgtc tcagtgcaag aaatgataca gcaataaata ttagtgcatt    14400
cataaaaagc atatttgttt atttattgct ttttagggct gtacccatgg catatggaag    14460
ttcccaggct aggggtcgat cagagctgta gaccccgacc tacaccacag ccacagcaac    14520
tcaggatcca agccacatct gcgacctaca ccacagctca cggcaatgct ggatccccaa    14580
cccactgagc aaggccaggg attgaaccgg caacctcatg gatactagtc ggatttggtt    14640
ctgctgtgcc ataatgggaa ctccaggcct gtttattttc ttaatttgca gcagcacaat    14700
gtaaagtgtt ttctcatagc tatccattca tttatgtccc tctttactaa tgtttatctc    14760 ttcttttta tccttaagga aatcatcaat gaactgaaca gggtaaggaa cattaatgat     14820
atttaaatta ttttaaaatt cattctttca aaaatatatt agctcacactt tttagtttta  14880 acaaagagaa ctcctgagaa aaaaacagta ataaactcaa ggtatcaaaa tctttcttat   14940
gatagtgtgt caaaaagtat attcttgcag ttcaaaagtg ttttgattta gaaaaacagt   15000 attttttcctg tgatatttat accttcactg aactttcaaa atgactaatg aattctactc   15060
ataattctaa atatttatttt tattgattta attttgtatc tatgaataga caaggcatta   15120
atatgaatga atgaatgggt gcaattttgg actaaccaat ttttttgcact tatcaccaaa  15180 actgaaagaa ttcttattat aaggttttat aaaaaaacaa tattatctgc acctagaatg   15240
ttttacataa tcacagttgg ttattctctt tctttacaca tgagtttctg ggccggggat    15300
cagatccaag ctgcacttga gacctaagtc acagctactt caatggagga cccttaaccc   15360
actttgctgg gctgggtatg aacccagcgc ttcctagtgc cacagatccc attgcaccac  15420
aggggaacct ctaacgcata tttttttaaa atctggtctg tcagatttt agtagttttg     15480 gtattgagac aacacaggtg ccactgaaga taaaaaaata tatcttccta actatccttc    15540
atacttgaat gatcatcctt tcttggcagg atgctaggag tgaatcaact gaagtaagat    15600
tctttattgt aaaactatta aatataatgt aaggaaaaga aagaaataaa atcatttcct    15660
ttaaatatcc taatgaaaat gaatgactaa ttcttttagg tcaaaactaa gacagatatc    15720
tctaattcaa agagagaaaa aaaaaaacat acaatgttat catctgtgag ccataattag    15780
ctggataact aaatcaatgg tattatattg agcttaaatt ctatggatca tgtcactact    15840
ccctgtactg ctatggtcat gaaaactgaa cacaacattc tagatgggaga aaatccattt   15900
```

```
tgcttaaata tttatacacc attgaaccaa tgcttcatag actttattt attacataat    15960 ctttaatcca atacttctgc ttaatagcca aaagccaagt aaaggaaaaa aagtaagggt    16020
agttaaagga aaatgtagga ttatttacac tgatttacca caacaaataa gaatccataa    16080
taatttatgt caagggagtt cccgtcatgg cgcagtggtt aacgaatctg actaggaacc    16140
atgaggttga gggttcgatc cctgctcttg ctcagtgggt taaggatccg gtgttgccct    16200
gagctgtggt gtaggtcgca gacgcggctc ggatcctgca ttactgtgac cctggtgtag    16260
gctggcagct acagctctga ttcgacccct agcctgggaa ctttcatatg ccgtgggagc    16320
ggcccaagaa atggcaaaaa gacaaaaaaa acaaacaaac aaacaaacaa aaattttatg    16380
ttaaactcag aaatgcagat tagggaggta aattctttgg ttagcctggt aggtaggctt    16440
ttttctttcc ttatcactgg ctcttaccac atatttctat ttcttttggc atctatttta    16500
tttgataatt attattttac atttgaatat ttgtcataaa aaataaattc tcttttcttt    16560
tctaagaatc atggcatgga aggccatgag gtaagaccct tattgtaata aactctacac    16620
ttacataaca tccatagtat atactctatg ctctatttta agaaaactct cttctcaaat    16680
tgagcaagat tgaacttccc aaacaaggtt attatacccca agaatgtaca atgttgtgcc    16740
agataatgtt aaaattagaa gaggaaatgt gtcttttaat tgataatcag ggaaaatgtt    16800
atttattaaa ataaagggtg taaggcaaaa tgtgcatgag tgtttcaaat gaaatatgag    16860
cctccaaaaa aaagaaaaa aaaacctgtc tctaccacct cagggtataa actcactcct    16920
gtttgtgagg gtagtcttgg ggagaaagaa tctggttgca gtaattactt aggatcaatg    16980
gcctatgcta cttaatccaa aagcatggaa aaaatccact agcccacaat atttggttaa    17040
tcaactttcc caagagatga atcatctgtt gactattaaa atcaatcttt taggtatgta    17100
cttgagaaca aaaattatat ccatatttaa atataaacgt ccgtgagtta gaaaaaaatc    17160
taaatagttc aaagtgtaga tgttttaaaa gctaatgtaa ttttagttcc ataccaaaat    17220
ttgttgttgt attttcatgt ttcaatttat tcccttcaaa gaagccccaa ggatacatga    17280
gaataaatat cccacccggg gttctgggtg cccaagctca gtagggcact tccttccaaa    17340
tttcatatat atttttgcatt ctactcaacc acatatctat gtttgatta ataaaatgtt    17400 gttttttagt gattggttat tacattccca catccaacat attttaaata aaattgacaa    17460
ccccaaaaag gtacgttata ttggccctga atgtttcatt accaattgct ttcattctaa    17520
acaaggagtt agcaacccag tatgaaagtg tggaacaaat ttccttctaa ttctaaaagt    17580
cacagtgttg ggaacactga ttttctctct tttagcaaag gggatctagc agttcatcaa    17640
gtgaggtaaa tcattttgat gttaattcag tatctcagtt agaaaatgtt tatgaaaact    17700
tgttgtgcta tgaatgttac acatcccata aggtctcatg gtacaggctc tatgtctaca    17760
gctctaccct aattttaaca tacaggctat gagcccaaaa gatataataa cgcaaatact    17820
tgtcagatga aattacagaa ttgtttctgc gctaacaatt ctatctggct atccatggtg    17880
ccccattttt tttctctaat tttttgcct ttcctaggtt ttggtagtac taaatatttt    17940
atttaaaatt actataagag ctatgcttct aaatcattaa tagaaacttg gtatttcctg    18000
tgcagacatc tactgattct aggttaactg ggtactggaa tccttactc cttgttaacc    18060 taaagagaa aaagagcagg catagaaggt cctttcgtaa actttgggag aagaaatttt    18120 caaaatataac ccaacccagt tatgcggagt ttctgggaga tcagtaaaag tgcatcgaat    18180
atttcacatc tacctccaac attctgaata acttccctgt tgaaatcagt gagaagagga    18240
aagggaatct tgagtacaac ctgtaccttg aattattcat cttatctcag ttaccaagga    18300
```

```
atgggtgcct aagatcaatt tatcacagtt aagcaacatg gtaactggct aattagtatt    18360
catacctTga gtataaatta ataagtcata aaactaacac tgcatgtttt tattttttaa    18420
ggaagttgtt ggcaatagtg ctgaggtgag atatacttac taaatttaaa atacattcac    18480
gttatccagg atgtgttaaa atttacttgt acttttttt ttcttttta gcagaagcac    18540 gttcaaaaag aagaagatgt gccctcccaa agctatctgg taaaatttta ctaaaagttt    18600
atcaaaggca aatgtaccaa ggaatgagta tgaatgttgt actgatacat tatttctcct    18660
tctcaacctc tgctacacct taatacatag taagccgtct aacagactct agatgtttac    18720
tgatcccctg caaaaataaa gctaacaact tttttatccc agggttttg tttgtttgtt    18780 tgtttgtttt gtcttttgtc tttttagggc cgcacctgca gcacatggag gttcccaggc    18840 tagggggtcta atcagagctg tagctgctgg cctgcatcac agccacagca atgccacatc    18900
caaaccgcat ctgcaaccta caccacagct cccagcaacg ctgggtccct aacccactga    18960
gcaaggccag ggatcaaacc ggaacctcat ggttcctagt cagattcgtt tccactgcgc    19020
catgatggga actcctatcc caggttatta attcatgctt tcatgagatt tgtgttttat    19080
agtctatttt tggatctgaa taacatagta ttttttttat ttttttaatt ttcccactgt    19140
acagcaaggg ggtcaggtta tccttacatg tatacattgc agttacagtt tttccccca    19200 ccctttcttc tgttgcaaca tgagtatcta gacatagttc tcaatgctat tcagcaggat    19260
ctccttgtaa atctattcta ggtgtgtctg ataagcccaa gctcccgatc cctcccactc    19320
cctccccctc ccatcaggca accacaagtc tcttctccaa gtccatgatt ttcttttctg    19380
aggagatgtt catttgtgct ggatattaga ttccagttat aagtgatatc atatggtatt    19440
tgcctttgtc tttctggctc atttcactca ggatgagatt ctctagttcc atccatgttg    19500
ctgcaaatgg cattatgtca tcctttttta tggctgagta gtattccatt gtgtatatat    19560
actacatctt ccgaatccaa tcatctgttg atggacattt ggattgtttc catatcctgg    19620
ctattgtgaa tacggctgca atgaacatgc gggtgcatgt gtctctttta agtagagctt    19680
tgtccggata gatgcccaag agtgggattg cggggtcata tggaagttct atgtatagat    19740
ttctaaggta tgtccaaact gttctccata gtggctgtac cagtttacat tcccaccagc    19800
agtgcaggag ggttcccttt tctccacagc ccctccagca cttgttattt gtggatttat    19860
taatgatggc cattctgact ggtgtgaggt ggtatctcat ggtagttttg atttgcattt    19920
ctctactaat tagggatgtt gagcattttt tcatgtgttt gttggccatc tgaataacat    19980
agtatttaaa tggcaccta cagatttggc cagatttgag ttgaactcta agctctacct    20040
tttactagca tgtgatgtta gttatttatc tgctataagt ctgcaaccta aactctaaaa    20100
tgataatata atgatagcaa tacacagcac aaagcaagca ctcggtaaac gtggcaagtc    20160
tcacgaaact taacatgttt ttgcccactt catctactat tctgatttaa tttggccaaa    20220
gttaaatcct ttgtcagaaa gcaaaaacaa ttttcaattt tcttagcaat tctgacataa    20280
gacacactgc aaataaaaat gaatattcat tcatatttga cagcatggta atttatttca    20340
cattaaaagt aagttatgaa agtagttttt ctagtattaa aatataattg gattagtcca    20400
aattatctgt ggttgaagta acattaaaag aggattacta gttcttcctt ctttgcacct    20460
aggaaaggtc atgttatgat tctagttata ttacttgaaa atgataggat gagactggat    20520
tgtctccaag caatggacaa tattttttt ttccttgaata gggacatctt caaggactga    20580
acaaatacaa actgcgccag ctggtaatat ctttattata ataacacaaa actaaactgt    20640
```

```
gcaaaatcaa aataattaag ttgtaaattg ggtccacctc tgaatatttt tttaagaaat    20700
tatttattct agacttgacc attaataata actgacaaat aatccaaatg attgcctatg    20760
tatttactgt cacagctatt tgtttctatt tatgccgaga gtagtattgt aaatcaggag    20820
gtgttcctgt cgtggcacag tggaaacgaa tctgactagg aaccatgagg ttgcaggttc    20880
aatccctggc ctcgctcaga gggttaagga tctggcattg ctatgagcag tggtgtaggc    20940
cggcagctat agctctgatt agaccactag cctgggaacc tccacaggcc acaggtgcag    21000
gcctgaaagg acaaaagaca aataatcat atccataatt gctaagcagg gagaaatttc     21060 cttttttac taaattcttt atcaaaccct cttagaccct cccacatgat gaattatatt      21120
cagaagttta ttcttttat tgttgttgca aattcagtct tgaaaggtgt tccataaata      21180
tgcctgcttc ttaaagcaca gatatgccaa ataaaccttc catttaagga aagagtgtag    21240
actcaggaga aggaaccagg agtcctaaat attcaacttg cttttgtcaa aattctctaa    21300
gaaagaggag cttttttgct gcaccttggg ttaaggggcc atcattgtca cagctgtggc    21360
tctggttgct gctgtggcac aggtttgatc cctgaactgg gaattttcac atgccatatg    21420
tgtggccaaa aaaaaaaaaa aaaccaaat aaacataaac aaaaagctct aagaggaaag     21480
aattggcaga ttgattgatc taatggtcta tgaatccatt tccttaggtg tgaaatggaa    21540
atacagttat tctcactccc tggtgttatt ttgaatatta aatgagcaat cgcctactca    21600
ggtctcccta agtccagctt gtagcaagtc cagtaaaagc ttcattcctc cttctcctgc    21660
ccccactcca cagcctctag aaaatttgct gcgctcatga gacttctgat aacattatga    21720
aagtctttca tcaggatatg tgtttgaact ataatgtcat aaactcttta tcagcagagg    21780
tatggataga taaaaaacat atcaattagc aagcccttc aattagcaag cccttcttcc     21840
actatttaat tttgatcctt ttgagtatca caatctttca tttggaaggt caaaaaaaat    21900
ttcttagcta tagcaaataa acaacctaat taggacttta gggaaaaaag cttgtcagtt    21960
taggtaaatt acctttttcac attttcttct gttatatatg taagatgaag agagttaata   22020
atgaatttaa tttgcaccte agttttact cttatttcaa tacctgagtt acctgtgttt     22080
ataaagtcca aataaattta aatttatcag tacttcactg gaattcatca ttactgatct    22140
aagaaattac ctgaataatc agttttagga cttagctctg atatgacaag gtcataaccc    22200
ccagaagtgt taggaccagt aaggcattgc tcattatgtt cattgtattt catagatggt    22260
catcagtttt tagcatagtc ctcaagtgca tgaaagtact tagtaaatct ctgttattca    22320
tatgaataaa atcaatatac taaaagaaga tgttctttct ttcttaggaa gctattcatg    22380
accaggtaaa gttatttatt tattaagtgt aaaatatttt agtatttcct tcatgtgtta    22440 tattttata atgtgcattc cttttttttt tataacagaa atatatccca atagagaaat     22500
ttatctccta cccatatctg gtaatatgtt atttaaaatt caccaaagat aatatttaaa    22560
taattgatta atagtcttat atggaaaata tgtattctta gagaaatgat aggttttct    22620 ttttcccagg gtatgagttt tataaattct ttatttccca aactatacta agtctagcct    22680
ttagttgaat attttttct aaagttagaa aataaaaagt gtattgctat tttttttcat     22740
aattttgacc tagaatactg tctatcctaa atttcatgga tgatgatata ctcttggtac    22800
attgtaaaat gaatgtgttg tatcagaaga tatctaagta atttaaaatg tctttccttt    22860
aaataggaac ttcacagaac aaatgaggac aagcataccc aacaggtaat attttgttta   22920
ataaattaca cagttatatt gtaaagttta aatatgtttg ttttaaaata ccctcatact    22980
tttgaggggg tttctttctt aggcagctct ttttattttt ttgcatttg gggccacacc     23040
```

```
caaggcatat ggaagttccc atactagggg ccgaattgaa actgtagctg ctgacctaca   23100
atgacaacgc cggatcctta acccactgag tgaggccacg gatggaacct acatcctcat   23160
ggttgctagt tgggttcgtt actgctgagc cacaagggg actctgcagg cagttatttc    23220
ttattcccag ctttctgaaa taatttatat tgatcaatca gagatgagaa ccatgtgtca   23280
ctcttctttg gaataagatt tgttctatcc ggtctgtctc acctgacgtg gtcagcctat   23340
ttataattct gagcactatc aagaattcat ctccatggtt acattaattt cccctttaag   23400
atattcttta attttgcatt tttgtccata atttgattct taaattcaat ttacatttag   23460
gaaactcaaa ctcaccatta tgctctttta agcaaagaga gtggagattt actaactgac   23520
actttctcaa gcaaccatct ggagccatag taaatgtctg tccaaaaaaa atcttcctga   23580
tcctctgttt tctcctctgt gaagtgagat tatatataat acctaacaga aactgactct   23640
tctcctgccc tcccttccac tgatgcccta gtgctcctgt ggcttctgct ttccttttta   23700
aggcaatgat gagttaccat gaaacatatg ttactctacc agctctgatt cctgtgaata   23760
gctacaccaa ttccaatcat ggaggctccc aatcactatt tgctgtttag ggaatcttat   23820
aaggatggta gagtatgttt catatgtcta agaagaaact tcctttagag aaggcaattg   23880
ggaaaatttt agtatgagtt ctcagatctc taacataaaa agcatttcaa gtaggttgct   23940
tcttacagct ttggttttat ttagccttaa aaaagtaact ttaattctct ttttctttcc   24000
agggagagcc tatgaaagga gtgaatcagg taagagtgag tgtgtgagtg tgtgtgtgtg   24060
tgtgtgtatt aatactgccc cataagctag tgctatgcta gtatttcttg gctattgact   24120
ggtgttggac tctctagagc tggttctaac attgctgtgg aagatctgat agatctgatt   24180
gccaaaggaa atgaatgaat gattctatgg ccatctgtga gtgatgatag cttcaggtca   24240
actttaagtc aggacaatct caaccagcta tttacattgt taaaatttga cctgttatta   24300
atctatagta tcatgtcatg aaaataattt gagttttcaa tcttagatct gacaccttct   24360
aattacagga ccttgagcaa attgtgctat tctctttgag cactgctttt tcatttgtga   24420
aattaatata tggacctatc catttatttc ctccccaaac ttccatatcc tgattttgg    24480 agtgtctttc tatatcttca cttttagaag tagtagctct gcattcaatt cagtttcttc   24540
agtctctctc tctctctctc tctctctcta tatatatata tatatatata tatatatata   24600
tatatatata tatatataca cacacacaga cacacacaca cggcatgcta attaaaaga    24660 atgcaaagta aaccacggag ttttctcaat atgaatgtta ttaggaagaa aaaaatttcc   24720
tcaagattca aaacatagta gtcatcaatc agtttatgt gcatctttac tgtgcatcag    24780
atttactctc aatttcttct gaattctct aatcacttct gagctaaagt aagagaaaag    24840
gcaattactc acttcatttg agatttaaag ggtacactaa cctcaacttt tcatgtaatt   24900
ccaaaaaaaa agagggtgat gattataatc tcaataagaa tatttgatag caataattta   24960
atcatggtat ttaattggat ttaaattaca aaactatttt tcccctctct gttaaggaac   25020
aggcctactt ctattttgag gtaaatttat tttattttat tcttttatcc aaatgattta   25080
taaaggaaaa gtattggtaa acatttataa tatagtaatc tttatgtagg taaccacagc   25140
aaaactggaa atgtttttat tttttattcc atcaaaaagc acatattttc acctaaatat   25200
atagagaatt atgttatgca taaaaacaag taaaacatca tgatagatga acagagtcac   25260
ctatcctgaa atttcagaaa ggaaaatggt ttggcaccaa aactttataa ttaggaaagg   25320
ataatgtgtt aggaattgga gaattctttt ccctttattc ctggcatttc tgagagcaga   25380
```

| | | | | | |
|---|---|---|---|---|---|
| ggtatggacc | ccgagtggga | ggcccttcct | tttgtttgag | ctcagtgtct | tcatggaaaa | 25440 |
| ttaagctaaa | gaacaaaatg | gccaaaaaag | tcctttccag | tccacaagtc | catgaggtta | 25500 |
| taaattttat | aataattaaa | ttcacacccc | tacattcctc | tgggctctgg | taactggact | 25560 |
| ccgattagta | atgcagattc | gtggagttca | atgctgaata | ttgaccttga | agaagttatt | 25620 |
| tcttcattac | tcacaagtct | cccaaaaagc | cctttccaaa | agttcctttg | ccatgatcca | 25680 |
| ctgcatggaa | gaatgtgatt | tctccgtttt | ccttgcagag | tagatatctc | ttgtgatgct | 25740 |
| aatagccatg | tcagaagtga | ataaaatgct | tcttttttc | agagattcta | aagagcaatt | 25800 |
| tcccatatcc | tgttgctatt | tcattctctc | tagcctctcc | accagttcta | ccagcttgat | 25860 |
| gcctatccct | atgctacctg | gtattatcct | ccacaatata | ttgctcaccc | attattcacc | 25920 |
| aacatccctc | aacccactgc | ccctgagaag | ggtggaaaaa | ctgagattat | gcctcagtgg | 25980 |
| tggtaagttc | attttaatga | ctgtatattg | atgttctacc | aaaggaaata | aagaaaact | 26040 |
| tcttaaagaa | cataccataa | aaacagattt | agaataaaca | tgacaaaatc | aatatctaga | 26100 |
| gcgtcatagt | agaattttcc | aaaatgggaa | attggcagga | cgttctgata | tctgcagcta | 26160 |
| atgttaatcc | actactcagg | aacttgtgga | gcagcgctct | ctgttctttg | agattcattc | 26220 |
| tgatgaagtc | aggaaaaagt | tttctatcca | agcaaaaac | acagtaattt | catttatcc | 26280 |
| tccttacaat | tttactaatc | tctaaaggct | tttcttttgg | ttatatatac | ccatgatata | 26340 |
| cattacaatt | cagtgtgggg | aataaagcac | agattttgac | atccaaaagt | cccaaatcca | 26400 |
| aatcctgacc | ttttttgctt | acttaaaata | atgtattaat | gcttattttt | ataattctga | 26460 |
| aggtgattaa | agacaataat | ctgttaagca | tagtgctggg | aagatacata | gcagtcagtt | 26520 |
| tttattgatt | tagtaaaatt | gtactgctga | ctatcttcat | cacatgattt | taagaattt | 26580 |
| tgttttttca | gaagaattaa | gtgaattctc | aggaactcca | caattatggc | ctttggtaag | 26640 |
| ttggaaatca | tttgtggaac | catcgatcct | cttttcgttt | aaagactcat | tacaaagata | 26700 |
| ggactgtaga | ctataaagat | ttttttttcct | gtagttgagc | tccttgtgga | cacattagca | 26760 |
| cttagataat | aattaaattg | gcttggacat | ttgcaaatgt | ttgtttcata | attatactat | 26820 |
| atgtaaatag | caatcaaatt | agataatttt | aatgaatata | atttattata | ttgaacccct | 26880 |
| atacaagtat | aggagcatga | atgctactaa | ttttccatca | agatgtgacc | ttgagatgct | 26940 |
| ggtaaactca | acagtgggat | tctattttt | atgatcacta | caataaaat | ccttagcaag | 27000 |
| tcatgtgata | aaaccaagta | tttgtttctc | aacaagaaaa | cagactttaa | cgtctacaga | 27060 |
| cttgttttaa | ttaacttcat | ccattgtact | ggtgtttccg | attgtatgtc | agtagagggg | 27120 |
| tgtgtgtgtg | tgtgtgtgtg | tgtgtgtgta | tgttttccct | ttctagtggt | ggaaatttcc | 27180 |
| cttccaactg | attgaattaa | ggaaaatgac | aaaacatatg | ggaaaggttt | ttctttgaat | 27240 |
| tccttggcca | tattttctct | gttactgcaa | agaaaatac | tacctagcaa | taaattgtct | 27300 |
| atataactta | aaattatcag | gataaatggg | tacatatgtc | agtcacagga | aagaacaaat | 27360 |
| aactttgtga | gtttcatctt | aaaatgaaga | gaaaatgatt | attcaaatgc | atcataacag | 27420 |
| tgtctcttcc | attcaaaaca | tgtaatataa | ccaaccacat | atttctttt | ctatttacag | 27480 |
| atgtgactga | aaataccatg | cttgaaattt | ctcctctcca | tctaccatgt | agaaccattt | 27540 |
| tatctgaaga | ctttgactgt | tcttttagaa | cagggaaatc | gcaaatcgaa | gtcaatcttc | 27600 |
| cttcttgaat | tctttactct | atattagata | gcatataatc | cttttccttt | ggcaaagttg | 27660 |
| tcctaacagt | ttagtgtcta | aatttcagtt | gtatcatgcc | agtaggaaga | ccactgaatc | 27720 |
| agagggaatt | aaaagtcttt | actaaatttc | aatatggaaa | ttttgtttaa | aaagcctttg | 27780 |

-continued

```
aattgcttct cctgtaagtg ccatcatttc aaataattgt gtgcagtgac tgagatttt    27840
cttccttctt ttcaataaat tacattttaa ggcacaactc ctattttttg tcattattcc   27900
attcagcaga atttgcacaa tcctgttaac agtctttatg cctgtaacat tttattttca   27960
ctaagttttt attacacttt caaccacaat tcaatgaaca aaatggtaaa tcttcatgcc   28020
tagctgatgc tgacaggtta taagctgggt ctaggatctt tcatttgaag tcacctgtct   28080
ataggatatt ctccatgaga acataggtgt ggctgcagag aagaacagtg gtatgacagt   28140
tgcgggtgca ctgggaattt gaaaaacatg gctaagctgt ttatttatgt caccagaacc   28200
tgtttgagcc aaactcattt gattatttga ttattataca cttacttta taattaggta    28260
gattagataa taaacattta ataggttaga ccatggcata cagtaacaca atactcagtg   28320
tcctcccgaa ctccagtgaa gagttatttc tcaaaatgac aatagtcgct tgcattaata   28380
ccctcaaaac cctgctggaa tttactttcc agagtttatt ccagggtccc caacaaaccc   28440
tatctgctgt gactctttaa gaaacttctt tccaccaggt cataaaatac aggtggcaag   28500
gtctcttgta ccacaaccta aacgacctat ttagttagca gttctgtctc ttatcgatta   28560
tatatataat tgatatgcac atatatgcat aacacctaaa cacgtatttt ttgcctataa   28620
cgcttttta ccagttgtca cttggtttgg tgacactagt ctccttccat tttccctgag    28680
gttggaaatg caatttcaat tactttgcac ctctcaccag agttctcagt caattgttta   28740
gcacaaaaga atttcataaa agtttgccct tcaaggaaaa gtttaaagga gaataattta   28800
tcctttgtag acacagggaa gtgcagggcc attagaacta agcatatcta tttatggatg   28860
tttaaatatt tctcttttcaa ttatgattgt caaactgcct tctagagtct cacaaataac   28920
agaagcagaa aaaatacag ttgtgaaaaa acagtgctga cagtgaactg aagaatatgt    28980
gcattcctca ttggctgccc cttccaatgc attgttgctg tgcaggaata cacaggtcaa   29040
atgtaaccaa atttggggac ttctaggtga aactagaaat gtggattggt gtgtaagatc   29100
tcctatttt aaatattggt ctagtgtttt ttaaatataa aatacacagt ctccttctct    29160
ttattggcca gacccaaccc ctctaacact agtctatgta ctatagtgta ctttaagtca   29220
ttaagtaaag gactttctac ttccagtcca atcaaggttg aatcccagtt acagtgaagt   29280
gaaagtgaga agtaggacat tagggtaata attagctaca gtaaacaaag aaatcatgat   29340
tccatcatga caaatacaca gtaagtgtta ggggctacat ggggctcatt gttaaaatgg   29400
ctcatcatgc tgacccatga gactgaccat cttgttcaag cgacatcctg ttttttgccac  29460
tggtgcctat tttcccaaga ctacaagacc agggggggacc acacacctcc agccttctca  29520
agattatgag tgcaccctac cgtgagatac ctctgacttt ctcatgacga tgtgaccacc   29580
agagtccacc tgcaggtgaa agataaacta taaactaacc ttcccccgct tcaggaatca   29640
atttcccctc tgcagagtat aagaaggccc tgctagaagg gcggggggc tgactcttct    29700
caaaggtcag tcagcctctc cttttttcctt ctaataaatt ttcttctctt tgcctgaaca  29760
cccaattcct tctctttttc tccatgctcg ccttacagta agaccttcag gagcacttgg   29820
gagcaggcgg ttctgtaaat tttccatacc ttcccatata ttccactttc aatagttggg   29880
ttcctattgt cctaactttc acaagaacta tccatttttat ggattcatgt catattaatc   29940
actatagatt agattttgca tgccctcccg aattcatatg ttgaagccct aactccccca   30000
tgtgatgcac ttggaggtgg catctttgga ggcaaatagg tcatgtgagt gggatatcta   30060
tgagtgggat tagtgcccct ctaagaaaag ctaggagaga gcttgtctat ctttctgcct   30120
```

```
tgtgaggata cagcagaaag gcaggcacct gcaggccaag agggagcctt caccggacac   30180
aggatctgct ggcacctgga tcttggtaaa tgttatttgt aactgtatgt ctgtgagttg   30240
ctatgggcag gatgtactgg ctggtaaaca ttgtttagta ataagtggat gtggtttaca   30300
ccagatttag gagaatctag gagtggtgag gtaaaatggg gtttggcatt caattgttga   30360
ctcattatat agctaaaata tgcctgcttg atgagcttat tgtaagagat ctcacaagtc   30420
attttgagct tcctagtatt gaggtgcttt gcacaccctc tgttagtggc ctaagaactg   30480
aagataacac atgtcttgtg ctaccaagca gtaggaggat aaatgaagtt tgctcttgag   30540
atctcagtac ctcttt catc tttcaatgca taccc ttctc ctgttgttgt actctgtcct   30600
ctgcctgtaa taaagctgtt ctgttagtgt aaactgtatg ggtctccttt aactatcaaa   30660
aatgttaggt cttgtgtgat taccacctcg ctgtaatata cagcaaaaaa aaaaaaaaa   30720 aaaagggaga attcatctgc aagttctctc tcatctcctg cttctcattc tgaaattttc   30780
acctcagtgg gggctaaaac tatgcatata acagtagcat taaccaacta ttacagtttc   30840
tgaggaaacc cggtcctgtg ctatagtaca caatcccatt caagtccaac agcaaagagg   30900
tgagtctgca ttgatgaggt cccaaccaca gggaaaagga agaagacagg caatatactg   30960
aatgcacaca tcgcaatgaa tcaccacaga tacttacttc caggctaagg gaagaatat   31020 cgctagttcc ccagcacttt ctcacatttt ctgtcaagtt gtaccttccc tcagataacc   31080
aatagtctag cttatcacac aagaatttaa tcgatcatta gattctaata aattccactt   31140
attggattac atattccatt atattttggc ctgattactg tcattcaatg ttatttatat   31200
aaaattcacc cttgtttttt ttgtggcagt aactcattca tttcaactgc agtatgatat   31260
cccattccac tttagaccat gacttattta tacaaaatac atttatacaa aatacaaatt   31320
tatacaaaat aacgtaaatg ttaattcaca tttatgttga ttttagtttg gggtattagc   31380
attgttagga gtattgggta aatgttttta gaatacatat gaaagcatat tatggtttcc   31440
ttttggttgt atacctaaga gaagaaatgt tagttataat ataagcagat gtttattttt   31500
gacaaagact cataatactt tccgagttgc ttgaaccatt ttatatttat tttaacatta   31560
cctagcattt attcagtttg cttattttg taaatacttg gttttaccaa ttcttctcat   31620
ttcagctatt ctggaggttg tgtcatgata tctggtatt ttaacttgca ttttccagag   31680
aaataatggt attgaacatc ttttcatata tttattgaca attaaaataa cctctttggt   31740
gaagtgccca ttcaaagata ttgcttgtgc actattatat tagttgcctt tgttattgaa   31800
atatgcccaa ttaaattttg gacaatttgg ggactggatt cagacaaaaa gttctgctgg   31860
ccatgtcagg tttgagatat taattagata ctccgatgtg gagaagaatg cagttgagca   31920
cttgaatttg gagttcagga aaaataagt ttgaggacat acatgtggaa gcttcaagcc   31980
cacgaatgga cttaaagtca tggaatcaaa caacatcaat catagtaagg ctaatccta   32040 gggtattcca cacattgcat gtttggaaaa ggagaaaatg ccagaagaga cgatgcaaag   32100
aaataactgg tgagttaaga gggaaatcaa gggcttatca ggcttaggat ttcgaataaa   32160
atttgcgata tttcaaaaaa aaaaaaaaa aaaaggaat gaccaactgg accaaatagc   32220
actgatagtt tgggtaaaat aaacatagat tggtaaaatg aatgttgttg gtaatcttga   32280
aaaaagtggt taccataggg gtaaagctca atgggaacag gttgatgaga gaataccatg   32340
tgaaacaata gacacggtag tttggacact tcctttctga tggttaccat agagcagtct   32400
aaagtactgc caaggatgga attttttctt taaagatggg agacattata gcctaagtat   32460
ggcttgcact tgatctgagg taaggaaaac actgaggatg caggaaagat gaaattactg   32520
```

```
ctagaaacaa gtccttgtgt aaacacaagg ggagggaatc aagtttacaa atgtaggagt    32580
tgtgtaacca agcaggaccc tgtgaagcct tcccacagtg gatccacact cttgtcctct    32640
gcctgcattt ttgtctatag aaaaacttta gtcaaagaat cagtttgatc agagaagtga    32700
gaaaatacag agaaaaagga atacagtcaa gcaagacaga gtaataatag tttagccact    32760
cagcaatgtc aaggacttat ggttcttcct catggactat agataatatg ctgagccatg    32820
tccttggaac ggttttgcag gtgctcaaac ccctaccagg cggaagaagt caactgcatg    32880
ctgcccacaa acatgtagac cccagaccag ttggaaacag aaggttgatg atgctgactc    32940
ccaattacct catcaccaaa cagttaggaa aatatccaag ggctgatcat gcccggctcc    33000
ttgaagagta agagtaagag tcctcaccac tcctccaaga ggcacacagt ccccgaagca    33060
ctagcctgct gtgtaccctc tgcctggcaa ttaaagctac ttttgccggt tccacatttt    33120
ctatttggcg tcagtgtata gaggcagccg atacttcggt gatagttggt agacagataa    33180
ttcattgcaa tgaaaaaatt actccacaga cagagacaag ggatatcaga gcttcacata    33240
agtctac                                                              33247

<210> SEQ ID NO 2
<211> LENGTH: 9300
<212> TYPE: DNA
<213> ORGANISM: Sus scrofa
<220> FEATURE:
<221> NAME/KEY: promoter
<222> LOCATION: (1)..(9300)
<223> OTHER INFORMATION: promoter of porcine alpah S1 casein

<400> SEQUENCE: 2
aggattacaa gattgctgtt ggataatgct ggatataaga aattgcatat ctttattctg      60
tagacctcag cagaagtatt gtgaagtttg tctttagcaa tgctgagatg ttctttacta     120
gttcttttta ctctatttct cggggcttaa atctttcatc ttatatgcat gttaggcatt     180
ctccaccagc taggatgtta tttcctccat cacctatccg aagattcgac accttgaata     240
cattgctttt gttgagtaaa agaataagca gtatgatata ttagaaagag cacaggctct     300
gatgttggga gatctgagtc atcatttact cattagctgg tgcaagcatt ttgtatggaa     360
attaatttac ttattaattt tattacttt attttactt ttattttttg ccatttctag       420
ggccgctccc gcagcatatg gaagttccca ggctacgggt ctaattggag ctgtagctgc     480
cagcctatgc cagatcctta gcaacgcagg atccaagtcg cgtctgcaaa ctacaccaca     540
gctcacggca acaccagatc cttaacccat tgaggaaggt cagggattga acctgcaacc     600
tcatggttcc tagttggatt cgttaagcac tgtgccacaa tgggaactcc ttaatttact     660
taatttataa agtttagtt tccttatcta caaaagggaa aataatgact tgtttctcta      720
cattacatga ttcttataag gagtagttgt gaaaataatt ataagaagac tttagaaatt     780
ataaagaaga ttataaattg acaaagaaat gaatctcttt cattctgctg atggatgact     840
tattaatcta tctggtaaac tgtggttctg atggccaata atgcctgtta aatacattgt     900
atcctcataa taatattgtt aaacagggac tgccaatgat tggaccccag gaaagtttat     960
cagtcatgaa aaccacattt tgtcaagtca gaagaactat tactgataag aaaaaaatct    1020
ctttacccac caaattacag tctttcagaa agaaatcact aggtgagatt tagttaacca    1080
agttaaattt tagcccagtt ttcccagatg tcttgagtag gtgaaagctt ccttcatggc    1140
aagatgaatg aattttggt tggaggtaag aggcaggtag tggtcttggc acgacataga     1200
```

```
cagataaact gttacttgtg agatatcata cctacaaaaa gaatataggg ttggataagg    1260
agatgcttta ttgtagacat tgctataaag gtaaacactt tcatggaaat acaattcagc    1320
agttttagca tctttgtttt tgccatatgt gttacatatt tttacaattt tcatatgctt    1380 ttaattttt aaaaggtatt ttacatacaa actttcatta ttgggtattt taaaagagaa     1440
gactgtgtat tacatttca aatctttcag tttctagcta ctcaaagtgt gctgcatggg     1500
tcaccagcag tgacatcacc ttagagctta ttaaaaattc attagctcct ggagttccca    1560
tcgtgatgca gcagaaacaa atttgactag gaaccatgag gttgcaggtt caatccctgc    1620
ctccctcagt gggttaaaaa tccgacatta ctgtgagctg tggtataggt cacagacccg    1680
gctgggatct ggtgttgctg tgactctagc atagtccagc agaaacagct ctgattagac    1740
ctctagcctg gaaaccttca tatgccgctg gtgccctaaa aggacaaaag agaaaaaaaa    1800
aaatacgtta gttcaggaca caccttcagat ttactaaatc tgaatctgaa ttttaacata   1860
atatcctggt gattcataag cacattaaag cattgttgta gttcattgtt ctgtgagaac    1920
atcaaatagt ataggattc atcaataaaa ttcagaagtt ctttctattc ccctctcata     1980
ttccatccca agctttcttc agttgtggtc actaataaaa attttgcctt cacacacaca    2040
cacacacaca cacacacaca cacataaggt ctttttaggg ctgcacccat ggcatatgga    2100
gtttcccagg ctaagggtca aatcagagct gtggccgctg gcctatgtca ctgccacaac    2160
aacaccagat ctgaattgca tctgtaactt acaccacagc tcatggcaat accgatcctt    2220
aacccactga gcaaggccag ggatcaatcc tgcatcttca tgtttactag tcagatttgt    2280
ttctgctgag ccatgacagg aaccctgcct ttacccttt atacatttt aatgcacata     2340 caatatacaa gtatgattca agacttctcg aaagttaaca aatccacaag ataggaaaat    2400
gatttgggca caaataatt agttgaggtt tttttaaaa aaaaaattct aataatgatc      2460
gttttaaatg agcacttact ttgtctcagg ctctcttcta agtgtgtgat ctaattttt     2520 cctctcgatc acacaggaag tggatgtcct taaacagatg tggacactga ggcacagtga    2580
ttttgcaaga ttaccctgct ggtcattgag agccagaaat taaatttaca atttgacctc    2640
aaaatcttgt cttgcaacaa ctacatcatg tgtttcattt aagatcttct gagacctatt    2700
gatacagcac taaaaaggat attgttctaa acacaaacat aaaatcaagc ataagttcca    2760
tatttccagg gatatcacat accacacctt accgaaagaa ctctatttta gttctagatg    2820
ccaagattcc acttgtgcaa tacttaagag taatgattcg ggggggggg atgcactggg     2880 ggtttgggat ggaaatgcta taaaactggg ttgtgatgat aattgtacaa ctataaatgt    2940
aataaattca ttgagaaata tagaaaaaaa taaaataaaa tccccctcc caaaaaaga     3000 attcactgtg gatcctctct tagattccaa acagtatgtg ggtttctaga gagaaacaaa    3060
gatgtctttc atattctcag taaatttcct tctggaagtt tcactgttaa aagacatttt    3120
cctagaagac tcaccagtca taaacccaaa tattcctggg agaatgctga caaactagct    3180
ttgaaattca tgttctgaat tattgactgt ctcatacaga atgagttctc caatgaggtt    3240
taatgtggac cagaatatgt agcaacagta cacaaaactt tgcagagtaa agtttacctc    3300
ctgactcaca gttcccttcc ctccaaactc gaagtctatt gctaatgttt cctctccttt    3360
ttgtgctagt ttttctaaga agtatgaatc taggaaagaa tgtttccaat attgaaactt    3420
gaaacacaag aaagctttca gcttggttgt cccttatctg acctatttcc actttcactg    3480
acttagggat tctgttggat tttcaaaacc gtcgtgatag tactagagta gctttgcctt    3540
tgtgtgccaa agatagtttt ggtttatggc tgtcgttttg ttatgattat tacaaagact    3600
```

```
ctcccatact cataagtgtt ccatgttgaa tgatcagtta tatgttcatc ctacatatga    3660
ctattacatc agaaaatcgc tattcaggta ataatttcat tctttcttta ctcacaggac    3720
aaaggcctgt ttaactacaa atcatctaaa tatgtgtctc aaatgtgaac tgtgattttt    3780
cttttttagt ggtttgaact gaacaatttt tttttaattt attttttttcc cactgtaaag   3840 caaggggatc aagttatcct tacatgtata cattttttatt ccccacccctt tgttctgttg   3900 caatatgagt atctagacat agttctcaat gctactcagt aggatctcct tgtaaatcta    3960
ctctaagttg tgtctgatca gcccaagctc ccaatccctc ccactccctc cctctcccat    4020
caggcagcca caagtctatt ttccaagtcc atgattttct tttctgtgga agggctcatt    4080
tgtgccttat ataagattcc aggtatcagt gatatatcat ttggtatttg tctttctctt    4140
tctgacttac ttcactcagt atgagagtct ctagttccat ccatgttgct gcaaatggca    4200
ttatgccatt cttttatgg ctgagtagta ttccattgtg tgtatatact acatcttccg    4260
gatccaatca tctgttgatg gacatttggg ttgtttccat gtcctggcta ttgtgaatag    4320
agctgcaatg aacatgtggg tgcatgtgtc tctttcaagg taagttttgt ctggatatat    4380
gcccaagagt gggattgcag ggtcacatgg tagttctatg tgtagatttc taaggtatct    4440
ccaaactgtt ctctatagtg gctgtaccag cttacattca caccaacagt gcaggagggt    4500 tccctttct ccacccccc cccagcattt gttattgtg gacttatcaa tgatggccat    4560
tctgactggt gtgaggtggt atctcatggt agttttgttt gcatttctct aataatcagg    4620
gatgttgagc attttttcat gtgcttgttg gccatctgta catcttcctt tgagaaatgt    4680
ctattcaggt cttttgccca tttttccatt gggttggttg gctttttgc tgttgagttg    4740 tataagttgc ttgtatattc tagagattaa gcccttgtcc attgcatcat ttgaagctat    4800
tttctcccat tctgtaagtt gtcttttttgt tttcttttgg gtttccttg ctgtgcaaaa    4860 gcttgtcagt ttgatgaggt cccattggtt tattttttgct cttatttctg ttgctttggg   4920
agattgacct gagaaaatat tcatgatgtt gatgtcagag agtattttgc caatgttctc    4980
ttccaggagt ttgatggtgt cttgtcttat atttaagtct ttcagccatt ttgagtttat    5040
ttttgtgcat ggtgtgagag tgtgtaccag tttcgttaat tttcatgcag ctgtccaggt    5100
ttcccagcaa tgcttgctga atagactttc tttttcccat tttatgttct tgcctccttt    5160
gtcaaagatt aattgaccat agttgtcaaa gtttatttct gggttctcta ttctgttcca    5220
ttggtctgtc tgttttgata gcagtggcat gttgtttga tgactgtggc tttgtaatat    5280
tttttgaagt ctgggaaagt tatgcctcct gcttgatttt tgtttctcag gattgctttg    5340
gcaattctga gtcttttgtg gttccatata aaatttggga ttgtttgttc tagttctgtg    5400
aaaaacgtca tcggtaattt gatagggatt gcattgaatc tgtatattac tttgggtagt    5460
atggccattt ttacattatt gattttttcca atccatgaac acggaatatc tttccatttc    5520
tttacatctt ctttgatttc tttgattata gtttatatg aactgaacaa ctttaagtga    5580
taaaagcaaa aggaaaaata cgaatataaa gcaaattgac ataagctaaa attttgcagg    5640
atttgacgtt gtataaatct acaatgaata tgtttgctcg aattacagtg aacagtcata    5700
ttttacaagt ataagaatga tttatttcaa aatacaaact taattaacta tattctatat    5760
ctaataagca aagtgaagat tgatccttat ccataggtac tagaaaaatc tgtgttttga    5820
gtttatgaga attcctatgg tggatacatg tgttcactaa gagttggctt gtctttaaaa    5880
gttctgattg ttcttctttg atggcaagcc ttattattat caaatctaag actccagtct    5940
```

```
cagttttttg agtctctatt tttggactat caggaatatt aaaattatca gcttttttgta    6000 tgtgaattac ccactatagt atgagactac agattttgtc ttacccaact tttatttccc    6060
ctgtgtcttg tctcatttct tcacctctgt aaataaataa tgtaagaatg agtaaacaaa    6120
tgaggataca gtagctttac acaacttaca gtatgatcct gaattggaaa taaaataagt    6180
cagttatcct ggatgcattc tcaggaaaag acaagagccg ggtattgtaa ggcagtggag    6240
aatacttgtt ctcagcccct tggataaatc agagtaaata gaaaatacta gtgcttttttt  6300 gacattgatg taatgcagtc agcaaggacg atactatcca aagagaagtt taacatggaa   6360
aactatagcc ttgtctatcc ccagtatgga aagcctgagc cactgcgaaa tttcttttaa   6420
ccccaaataa tgttcctacc atatgactgt aaattggctg tgaatatcac tatggattta   6480
ttattttatt tttaaatttt tttggtcttt tttcttttta gggctgcacc catggcatat    6540
ggaggttccc aggctagggg tcgaattgga gttgtagctg ccagcctaca ccacagccac   6600
agcaatgcca gatctgagct gtgtctgcaa cttacaccac agctcatggc aacaccagat   6660
cattgacccc ttgagtgagg ccagggatcg aacctgcaac ctcatggttc ctagtcagat   6720
tcatttcccc tgcgccacaa tgagaattcc agaatttttt taaatatata gtgtgatacc   6780
tttctgtaaa caagcagtca caatcaacaa ttttttaaat ccagctctat gtatagatat    6840
tttattcagc atgcaatttt tttcctaaaa ttaacaatgc cagttaattc taggattata   6900
tttcaggact ggaagaaaag tttttttttc cttttattta cttactttaa aaggtggaaa   6960
attggagtta tggttgattt tttgggggggg gggagtattt aaaaattgta ttcttaaata   7020
aaaattattc ttgaataatt attttttaatt aagaaatcta acaattaaat taatgaatac   7080
tatcacaaca catatacccca aaataaagca agcagaaaat tatttggtgt agttaaaata  7140
ctaccaaagt ttataaggca attgtatttt cttttttggtt aaaaaaaaga tcagatcaca  7200
tataaggtaa cttactccac aaggtaactt acttagaata cttagaataa atacttagaa   7260
gacttagaat aaataatagg gaataaatag agttttaaaa ggtgaaatag atgatgaaat   7320
cttctcatgg tctagtacaa ttataaaaat taaaaatttt tgatgatttt attttgtctc   7380 aagaattttcc cttacaggta ttgacttttt caaaagctgt aaaggaaatt ttattgctat   7440
attaatcttt ccaattatcc atttaactta aaaagcatgt tcttataata accataaata   7500
tggaattttt atgtatctta atttttgaata atgtcattcc atttcctgta taatttggta   7560
tcatagcatg aatcactcct ttgttgaaaa ctctcctcag aatttcttgg gagaaaaatt   7620
ggacagaaaa ttaatttcct cttttgagaga attcttagaa tttaaatgac actattggtt   7680
gaactgaaac cacaaaatta gcattttact aatcactagg tttaaatatt tgtgaaacaa   7740
agagatctgc caccatcttg atcatcagct cagcttgctt cttctttccg gtcttgggtt   7800 caaggtatttt catttacata tagcaaaatg tgatatatta tgatttcaat ctgtctaatt   7860
tttcactcct cactaaaaaa tatgcactgg taacttttct gtgtgattcc aaatattgat   7920
accttttaat gatatactgg tggcttaaaa atgcatttgc aaatgtcgat gccatctatc    7980
tcagagcttt agttgaaaaa taatagtttt ataaagacca aatttttttt gccaaatttt    8040
atgaaaactt attatgtgaa ataatttata atcttttaaa agatcatagt gaggatcatt   8100
tctggtagaa tatttcaaga ccattttttat tccatgtcat taggttaata aaattaattc   8160
tataaaggat atgtcaatga tatacacaga tataaatgac tacttttttaa aagatggtta    8220 gatttggata tttggaaaaa tgcaaatgaa taaaaccagt aaactcattt tggatttata   8280
aatatgtctt ccttacaaat gcagttagat tctacaatat gtagactgaa acagtatgta   8340
```

```
taaaataagc tgattagttt gttggctaat gtataaacaa attgcatgta tattatgact    8400
ttcctttcct aatttctctg gaaaccagtt tcccaggaca taagttctaa gtatctctgg    8460
gttcttgtaa tttgatggaa ctctagaagt cacacatgat aagacatcag aatcttatga    8520
ttctgctcaa tgaagtcgtc tttatgcagt catgtcatgg atatagcaac gtagaaaaac    8580
ataacataat agctagactt taaaaaaaaa ttgatggagg ttaaatgttt ctacataata    8640
tgcaccaaca gtgttttttcc caaagacgct gaaaaagcag gattctctaa catagaccta    8700
gaaaaacacc ttcaaaaaat tgcagatagg gagttcccgt tgtggctcag tggttaacaa    8760
atccgactag gaaccatgag gttgcaggtt caatccctgg ccttgctcag tgggttaaag    8820
gatctggcat tgatgtgagc tgtggtgtag tcgaagacg tggcttggat cccacgttgc     8880
tgtggctctg gtgtaggctg gtggctacag ctctgattca accccctagcc tgggaacctc    8940 cacatgccgt gggagcggcc caaaaaaagg caaaaagacc aaaaaaaaat ttttttttca    9000
gataaaatta aatgccagtt ccctgtgcct tttagtttat tatcaatttt tagcaaatct    9060
gatggtctaa gaggaaatat ttaaaataat taattgtagt attcttaaat ttagtagtat    9120
ttaaatatta atgtttatgt attcctctga caaaaccta ttaccacttc aaggatcaaa     9180
tgttttgttt tagagggtga tactggtgtt tcttatctca tataagcact aagcaagata    9240
atttgaatga taaatttttc ttgtgagtaa attttctgtc agacctaaat ttttattttg    9300

<210> SEQ ID NO 3
<211> LENGTH: 5470
<212> TYPE: DNA
<213> ORGANISM: Sus scrofa
<220> FEATURE:
<221> NAME/KEY: promoter
<222> LOCATION: (1)..(5470)
<223> OTHER INFORMATION: Pig aS1 casein promoter 5.5kb

<400> SEQUENCE: 3
ggctgtcgtt ttgttatgat tattacaaag actctcccat actcataagt gttccatgtt      60
gaatgatcag ttatatgttc atcctacata tgactattac atcagaaaat cgctattcag     120
gtaataattt cattctttct ttactcacag gacaaaggcc tgtttaacta caaatcatct     180
aaatatgtgt ctcaaatgtg aactgtgatt tttctttttt agtggtttga actgaacaat     240
ttttttttaa tttattttttt tcccactgta aagcaagggg atcaagttat ccttacatgt     300
atacattttt attccccacc ctttgttctg ttgcaatatg agtatctaga catagttctc     360
aatgctactc agtaggatct ccttgtaaat ctactctaag ttgtgtctga tcagcccaag     420
ctcccaatcc ctcccactcc ctccctctcc catcaggcag ccacaagtct attttccaag     480
tccatgattt tcttttctgt ggaagggctc atttgtgcct tatataagat tccaggtatc     540
agtgatatat catttggtat ttgtctttct ctttctgact tacttcactc agtatgagag     600
tctctagttc catccatgtt gctgcaaatg gcattatgcc attctttta tggctgagta     660 gtattccatt gtgtgtatat actacatctt ccggatccaa tcatctgttg atggacattt     720
gggttgtttc catgtcctgg ctattgtgaa tagagctgca atgaacatgt gggtgcatgt     780 gtctcttttca aggtaagttt tgtctggata tatgcccaag agtgggattg cagggtcaca    840
tggtagttct atgtgtagat ttctaaggta tctccaaact gttctctata gtggctgtac    900
cagcttacat tcacaccaac agtgcaggag ggttcccttt tctccacccc cccccagca    960 tttgttattt gtggacttat caatgatggc cattctgact ggtgtgaggt ggtatctcat   1020
```

```
ggtagttttg tttgcatttc tctaataatc agggatgttg agcattttttt catgtgcttg    1080 ttggccatct gtacatcttc ctttgagaaa tgtctattca ggtctttttgc ccattttttcc   1140 attgggttgg ttggcttttt tgctgttgag ttgtataagt tgcttgtata ttctagagat    1200
taagcccttg tccattgcat catttgaagc tattttctcc cattctgtaa gttgtctttt    1260
tgttttcttt tgggtttcct ttgctgtgca aaagcttgtc agtttgatga ggtcccattg    1320 gtttatttttt gctcttattt ctgttgcttt gggagattga cctgagaaaa tattcatgat   1380
gttgatgtca gagagtattt tgccaatgtt ctcttccagg agtttgatgg tgtcttgtct   1440
tatatttaag tctttcagcc attttgagtt tattttttgtg catggtgtga gagtgtgtac   1500
cagtttcgtt aattttcatg cagctgtcca ggtttcccag caatgcttgc tgaatagact   1560
ttctttttcc catttttatgt tcttgcctcc tttgtcaaag attaattgac catagttgtc   1620
aaagtttatt tctgggttct ctattctgtt ccattggtct gtctgttttg atagcagtgg   1680
catgttgttt tgatgactgt ggcttttgtaa tatttttttga agtctgggaa agttatgcct  1740
cctgcttgat ttttgtttct caggattgct ttggcaattc tgagtctttt gtggttccat   1800 ataaaattttt ggattgtttg ttctagttct gtgaaaaacg tcatcggtaa tttgataggg  1860
attgcattga atctgtatat tactttgggt agtatggcca ttttttacatt attgattttt   1920 ccaatccatg aacacggaat atctttccat ttctttacat cttctttgat ttctttgatt   1980
atagttttat atgaactgaa caacttttaag tgataaaagc aaaaggaaaa atacgaatat   2040
aaagcaaatt gacataagct aaaattttgc aggatttgac gttgtataaa tctacaatga   2100
atatgtttgc tcgaattaca gtgaacagtc atattttaca agtataagaa tgatttattt   2160
caaaatacaa acttaattaa ctatattcta tatctaataa gcaaagtgaa gattgatcct   2220
tatccatagg tactagaaaa atctgtgttt tgagtttatg agaattccta tggtggatac    2280
atgtgttcac taagagttgg cttgtcttta aaagttctga ttgttcttct ttgatggcaa   2340
gccttattat tatcaaatct aagactccag tctcagtttt ttgagtctct ttttttggac   2400
tatcaggaat attaaaatta tcagcttttt gtatgtgaat tacccactat agtatgagac   2460
tacagatttt gtcttaccca actttttattt cccctgtgtc ttgtctcatt tcttcacctc   2520
tgtaaataaa taatgtaaga atgagtaaac aaatgaggat acagtagctt tacacaactt   2580
acagtatgat cctgaattgg aaataaaata agtcagttat cctggatgca ttctcaggaa   2640
aagacaagag ccgggtattg taaggcagtg gagaatactt gttctcagcc ccttggataa    2700
atcagagtaa atagaaaata ctagtgcttt tttgacattg atgtaatgca gtcagcaagg   2760
acgatactat ccaaagagaa gtttaacatg gaaaactata gccttgtcta tccccagtat    2820
ggaaagcctg agccactgcg aaatttcttt taaccccaaa taatgttcct accatatgac   2880
tgtaaattgg ctgtgaatat cactatggat ttattatttt attttttaaat tttttttggtc 2940 ttttttcttt ttagggctgc acccatggca tatggaggtt cccaggctag ggtcgaatt    3000 ggagttgtag ctgccagcct acaccacagc cacagcaatg ccagatctga gctgtgtctg   3060
caacttacac cacagctcat ggcaacacca gatcattgac cccttgagtg aggccaggga   3120
tcgaacctgc aacctcatgg ttcctagtca gattcatttc ccctgcgcca caatgagaat    3180
tccagaattt ttttaaatat atagtgtgat acctttctgt aaacaagcag tcacaatcaa    3240
caatttttta aatccagctc tatgtataga tattttattc agcatgcaat ttttttccta    3300
aaattaacaa tgccagttaa ttctaggatt atatttcagg actggaaaga aagtttttttt  3360 ttcctttttat ttacttactt taaaaggtgg aaaattggag ttatggttga tttttttggg  3420
```

```
ggggggagta tttaaaaatt gtattcttaa ataaaaatta ttcttgaata attattttta    3480
attaagaaat ctaacaatta aattaatgaa tactatcaca acacatatac ccaaaataaa    3540
gcaagcagaa aattatttgg tgtagttaaa atactaccaa agtttataag gcaattgtat    3600 tttcttttg gttaaaaaaa agatcagatc acatataagg taacttactc cacaaggtaa    3660
cttacttaga atacttagaa taaatactta gaagacttag aataaataat agggaataaa    3720
tagagtttta aaaggtgaaa tagatgatga aatcttctca tggtctagta caattataaa    3780
aattaaaaat ttttgatgat tttattttgt ctcaagaatt tcccttacag gtattgactt    3840
tttcaaaagc tgtaaggaa attttattgc tatattaatc tttccaatta tccatttaac    3900
ttaaaaagca tgttcttata ataaccataa atatggaatt tttatgtatc ttaattttga    3960
ataatgtcat tccatttcct gtaaatttg gtatcatagc atgaatcact cctttgttga    4020
aaactctcct cagaatttct tgggagaaaa attggacaga aaattaattt cctctttgag    4080
agaattctta gaatttaaat gacactattg gttgaactga aaccacaaaa ttagcatttt    4140
actaatcact aggtttaaat atttgtgaaa caaagagatc tgccaccatc ttgatcatca    4200
gctcagcttg cttcttcttt ccggtcttgg gttcaaggta tttcatttac atatagcaaa    4260
atgtgatata ttatgatttc aatctgtcta attttcact cctcactaaa aaatatgcac    4320
tggtaacttt tctgtgtgat tccaaatatt gataccttt aatgatatac tggtggctta    4380
aaaatgcatt tgcaaatgtc gatgccatct atctcagagc tttagttgaa aaataatagt    4440
tttataaaga ccaaaatttt tttgccaaat tttatgaaaa cttattatgt gaaataattt    4500
ataatctttt taaagatcat agtgaggatc atttctggta gaatatttca agaccatttt    4560
tattccatgt cattaggtta ataaaattaa ttctataaag gatatgtcaa tgatatacac    4620
agatataaat gactactttt taaagatgg ttagatttgg atatttggaa aaatgcaaat    4680
gaataaaacc agtaaactca ttttggattt ataaatatgt cttccttaca aatgcagtta    4740
gattctacaa tatgtagact gaaacagtat gtataaaata agctgattag tttgttggct    4800
aatgtataaa caaattgcat gtatattatg actttccttt cctaatttct ctggaaacca    4860
gtttcccagg acataagttc taagtatctc tgggttcttg taatttgatg gaactctaga    4920
agtcacacat gataagacat cagaatctta tgattctgct caatgaagtc gtctttatgc    4980
agtcatgtca tggatatagc aacgtagaaa aacataacat aatagctaga ctttaaaaaa    5040
aaattgatgg aggttaaatg tttctacata atatgcacca acagtgtttt tcccaaagac    5100
gctgaaaaag caggattctc taacatagac ctagaaaaac accttcaaaa aattgcagat    5160
agggagttcc cgttgtggct cagtggttaa caaatccgac taggaaccat gaggttgcag    5220
gttcaatccc tggccttgct cagtgggtta aaggatctgg cattgatgtg agctgtggtg    5280
taggtcgaag acgtggcttg gatcccacgt tgctgtggct ctggtgtagg ctggtggcta    5340
cagctctgat tcaacccta gcctgggaac ctccacatgc cgtgggagcg gcccaaaaaa    5400
aggcaaaaag accaaaaaaa aattttttt tcagataaaa ttaaatgcca gttccctgtg    5460
ccttttagtt                                                          5470
```

<210> SEQ ID NO 4
<211> LENGTH: 4980
<212> TYPE: DNA
<213> ORGANISM: Sus scrofa
<220> FEATURE:
<221> NAME/KEY: promoter
<222> LOCATION: (1)..(4980)

<223> OTHER INFORMATION: Pig aS1 casein promoter 5.0kb

<400> SEQUENCE: 4

```
agctgcaatg aacatgtggg tgcatgtgtc tctttcaagg taagttttgt ctggatatat      60
gcccaagagt gggattgcag ggtcacatgg tagttctatg tgtagatttc taaggtatct     120
ccaaactgtt ctctatagtg gctgtaccag cttacattca caccaacagt gcaggagggt     180
tccctttttct ccaccccccc cccagcattt gttattgtg gacttatcaa tgatggccat     240
tctgactggt gtgaggtggt atctcatggt agttttgttt gcatttctct aataatcagg     300
gatgttgagc attttttcat gtgcttgttg gccatctgta catcttcctt tgagaaatgt     360
ctattcaggt cttttgccca tttttccatt gggttggttg gcttttttgc tgttgagttg     420
tataagttgc ttgtatattc tagagattaa gcccttgtcc attgcatcat ttgaagctat     480
tttctcccat tctgtaagtt gtcttttgt tttcttttgg gtttcctttg ctgtgcaaaa      540
gcttgtcagt ttgatgaggt cccattggtt tattttgct cttatttctg ttgctttggg     600
agattgacct gagaaaatat tcatgatgtt gatgtcagag agtattttgc caatgttctc     660
ttccaggagt ttgatggtgt cttgtcttat atttaagtct ttcagccatt ttgagtttat     720
ttttgtgcat ggtgtgagag tgtgtaccag tttcgttaat tttcatgcag ctgtccaggt     780
ttcccagcaa tgcttgctga atagactttc ttttttccat tttatgttct tgcctccttt     840
gtcaaagatt aattgaccat agttgtcaaa gtttatttct gggttctcta ttctgttcca     900
ttggtctgtc tgttttgata gcagtggcat gttgtttga tgactgtggc tttgtaatat      960
tttttgaagt ctgggaaagt tatgcctcct gcttgatttt tgtttctcag gattgctttg    1020
gcaattctga gtcttttgtg gttccatata aaattttgga ttgtttgttc tagttctgtg    1080
aaaaacgtca tcggtaattt gatagggatt gcattgaatc tgtatattac tttgggtagt    1140
atggccattt ttacattatt gattttttcca atccatgaac acggaatatc tttccatttc    1200
tttacatctt ctttgatttc tttgattata gttttatatg aactgaacaa ctttaagtga    1260
taaaagcaaa aggaaaaata cgaatataaa gcaaattgac ataagctaaa attttgcagg    1320
atttgacgtt gtataaatct acaatgaata tgtttgctcg aattacagtg aacagtcata    1380
ttttacaagt ataagaatga tttatttcaa aatacaaact taattaacta tattctatat    1440
ctaataagca aagtgaagat tgatccttat ccataggtac tagaaaaatc tgtgttttga    1500
gtttatgaga attcctatgg tggatacatg tgttcactaa gagttggctt gtctttaaaa    1560
gttctgattg ttcttctttg atggcaagcc ttattattat caaatctaag actccagtct    1620
cagttttttg agtctctatt tttggactat caggaatatt aaaattatca gctttttgta    1680
tgtgaattac ccactatagt atgagactac agatttgtc ttaccccaact tttatttccc    1740
ctgtgtcttg tctcatttct tcacctctgt aaataaataa tgtaagaatg agtaaacaaa    1800
tgaggataca gtagctttac acaacttaca gtatgatcct gaattgggaa taaaataagt    1860
cagttatcct ggatgcattc tcaggaaaag acaagagccg ggtattgtaa ggcagtggag    1920
aatacttgtt ctcagcccct tggataaatc agagtaaata gaaaatacta gtgctttttt    1980
gacattgatg taatgcagtc agcaaggacg atactatcca aagagaagtt taacatggaa    2040
aactatagcc ttgtctatcc ccagtatgga aagcctgagc cactgcgaaa tttctttaa    2100
cccaaaataa tgttcctacc atatgactgt aaattggctg tgaatatcac tatggattta    2160
ttattttatt tttaaatttt tttggtcttt tttcttttta gggctgcacc catggcatat    2220
ggaggttccc aggctagggg tcgaattgga gttgtagctg ccagcctaca ccacagccac    2280
```

```
agcaatgcca gatctgagct gtgtctgcaa cttacaccac agctcatggc aacaccagat    2340
cattgacccc ttgagtgagg ccagggatcg aacctgcaac ctcatggttc ctagtcagat    2400
tcatttcccc tgcgccacaa tgagaattcc agaattttt taaatatata gtgtgatacc     2460
tttctgtaaa caagcagtca caatcaacaa ttttttaaat ccagctctat gtatagatat    2520
tttattcagc atgcaatttt tttcctaaaa ttaacaatgc cagttaattc taggattata    2580
tttcaggact ggaagaaag ttttttttc cttttattta cttactttaa aaggtggaaa      2640
attggagtta tggttgattt tttgggggg gggagtattt aaaaattgta ttcttaaata     2700
aaaattattc ttgaataatt attttaatt aagaaatcta acaattaaat taatgaatac     2760
tatcacaaca catataccca aaataaagca agcagaaaat tatttggtgt agttaaaata    2820
ctaccaaagt ttataaggca attgtatttt cttttggtt aaaaaaaga tcagatcaca      2880 tataaggtaa cttactccac aaggtaactt actagaata cttagaataa atacttagaa     2940
gacttagaat aaataatagg gaataaatag agttttaaaa ggtgaaatag atgatgaaat    3000
cttctcatgg tctagtacaa ttataaaaat taaaattttt tgatgatttt attttgtctc    3060
aagaatttcc cttacaggta ttgactttt caaaagctgt aaaggaaatt ttattgctat     3120
attaatcttt ccaattatcc atttaactta aaagcatgt tcttataata accataaata     3180
tggaattttt atgtatctta attttgaata atgtcattcc atttcctgta taatttggta    3240
tcatagcatg aatcactcct ttgttgaaaa ctctcctcag aatttcttgg gagaaaaatt    3300
ggacagaaaa ttaatttcct cttttgagaga attcttagaa tttaaatgac actattggtt   3360
gaactgaaac cacaaaatta gcattttact aatcactagg tttaaatatt tgtgaaacaa    3420
agagatctgc caccatcttg atcatcagct cagcttgctt cttctttccg gtcttgggtt    3480
caaggtattt catttacata tagcaaaatg tgatatatta tgatttcaat ctgtctaatt    3540
tttcactcct cactaaaaaa tatgcactgg taacttttct gtgtgattcc aaatattgat    3600
accttttaat gatatactgg tggcttaaaa atgcatttgc aaatgtcgat gccatctatc    3660
tcagagcttt agttgaaaaa taatagttt ataaagacca aattttttt gccaaatttt     3720 atgaaaactt attatgtgaa ataatttata atctttttaa agatcatagt gaggatcatt    3780
tctggtagaa tatttcaaga ccattttat tccatgtcat taggttaata aaattaattc    3840
tataaaggat atgtcaatga tatacacaga tataaatgac tacttttaa aagatggtta     3900 gatttggata tttggaaaaa tgcaaatgaa taaaaccagt aaactcattt tggatttata    3960
aatatgtctt ccttacaaat gcagttagat tctacaatat gtagactgaa acagtatgta    4020
taaaataagc tgattagttt gttggctaat gtataaacaa attgcatgta tattatgact    4080
ttcctttcct aatttctctg gaaccagtt tcccaggaca taagttctaa gtatctctgg     4140
gttcttgtaa tttgatggaa ctctagaagt cacacatgat aagacatcag aatcttatga    4200
ttctgctcaa tgaagtcgtc tttatgcagt catgtcatgg atatagcaac gtagaaaaac    4260
ataacataat agctagactt taaaaaaaaa ttgatggagg ttaaatgttt ctacataata    4320
tgcaccaaca gtgttttcc caagacgct gaaaagcag gattctctaa catagaccta      4380 gaaaacacc ttcaaaaaat tgcagatagg gagttcccgt tgtggctcag tggttaacaa     4440
atccgactag gaaccatgag gttgcaggtt caatccctgg ccttgctcag tgggttaaag    4500
gatctggcat tgatgtgagc tgtggtgtag gtcgaagacg tggcttggat cccacgttgc    4560
tgtggctctg gtgtaggctg gtggctacag ctctgattca accccctagcc tgggaacctc   4620
```

```
cacatgccgt gggagcggcc caaaaaaagg caaaaagacc aaaaaaaaat tttttttttca    4680 gataaaatta aatgccagtt ccctgtgcct tttagtttat tatcaatttt tagcaaatct    4740
gatggtctaa gaggaaatat ttaaaataat taattgtagt attcttaaat ttagtagtat    4800
ttaaatatta atgtttatgt attcctctga caaaaccccta ttaccacttc aaggatcaaa    4860
tgttttgttt tagagggtga tactggtgtt tcttatctca tataagcact aagcaagata    4920
atttgaatga taaattttttc ttgtgagtaa attttctgtc agacctaaat ttttatttg     4980
```

<210> SEQ ID NO 5
<211> LENGTH: 4276
<212> TYPE: DNA
<213> ORGANISM: Artificial Sequence
<220> FEATURE:
<223> OTHER INFORMATION: 3'arm 4.3kb

<400> SEQUENCE: 5

```
ttacaattca gtgtggggaa taaagcacag attttgacat ccaaaagtcc caaatccaaa      60
tcctgacctt ttttgcttac ttaaaataat gtattaatgc ttattttttat aattctgaag    120 gtgattaaag acaataatct gttaagcata gtgctgggaa gatacatagc agtcagtttt    180
tattgattta gtaaaattgt actgctgact atcttcatca catgatttta agaattttttg   240 ttttttcaga agaattaagt gaattctcag gaactccaca attatggcct ttggtaagtt    300
ggaaatcatt tgtggaacca tcgatcctct tttcgtttaa agactcatta caaagatagg    360
actgtagact ataaagattt ttttttcctgt agttgagctc cttgtggaca cattagcact    420
tagataataa ttaaattggc ttggacattt gcaaatgttt gtttcataat tatactatat    480
gtaaatagca atcaaattag ataatttttaa tgaatataat ttattatatt gaaccccctat  540 acaagtatag gagcatgaat gctactaatt ttccatcaag atgtgacctt gagatgctgg    600
taaactcaac agtgggattc tatttttttat gatcactaca ataaaaatcc ttagcaagtc   660
atgtgataaa accaagtatt tgtttctcaa caagaaaaca gactttaacg tctacagact    720
tgttttaatt aacttcatcc attgtactgg tgtttccgat tgtatgtcag tagaggggtg    780
tgtgtgtgtg tgtgtgtgtg tgtgtgtatg ttttcccttt ctagtggtgg aaatttccct    840
tccaactgat tgaattaagg aaaatgacaa acatatggg aaaggttttt ctttgaattc     900
cttggccata ttttctctgt tactgcaaaa gaaaatacta cctagcaata aattgtctat    960
ataacttaaa attatcagga taaatgggta catatgtcag tcacaggaaa gaacaaataa   1020
ctttgtgagt tcatcttaa aatgaagaga aaatgattat tcaaatgcat cataacagtg    1080
tctcttccat tcaaaacatg taatataacc aaccacatat ttcttttttct atttacagat  1140 gtgactgaaa ataccatgct tgaaatttct cctctccatc taccatgtag aaccatttta   1200
tctgaagact ttgactgttc ttttagaaca gggaaatcgc aaatcgaagt caatcttcct   1260
tcttgaattc tttactctat attagatagc atataatcct tttcctttgg caaagttgtc   1320
ctaacagttt agtgtctaaa tttcagttgt atcatgccag taggaagacc actgaatcag   1380
agggaattaa aagtctttac taaatttcaa tatggaaatt ttgttaaaaa gcctttgaa    1440 ttgcttctcc tgtaagtgcc atcatttcaa ataattgtgt gcagtgactg agatttttct   1500
tccttctttt caataaatta catttttaagg cacaactcct attttttgtc attattccat   1560
tcagcagaat ttgcacaatc ctgttaacag tctttatgcc tgtaacattt tatttttcact  1620 aagttttttat tacactttca accacaattc aatgaacaaa atggtaaatc ttcatgccta   1680
gctgatgctg acaggttata agctgggtct aggatctttc atttgaagtc acctgtctat   1740
```

```
aggatattct ccatgagaac ataggtgtgg ctgcagagaa gaacagtggt atgacagttg    1800
cgggtgcact gggaatttga aaaacatggc taagctgttt atttatgtca ccagaacctg    1860
tttgagccaa actcatttga ttatttgatt attatacact tacttttata attaggtaga    1920
ttagataata aacattttaat aggttagacc atggcataca gtaacacaat actcagtgtc    1980
ctcccgaact ccagtgaaga gttattctc aaaatgacaa tagtcgcttg cattaatacc    2040
ctcaaaaccc tgctggaatt tactttccag agtttattcc agggtcccca acaaacccta    2100
tctgctgtga ctctttaaga aacttctttc caccaggtca taaaatacag gtggcaaggt    2160
ctcttgtacc acaacctaaa cgacctattt agttagcagt tctgtctctt atcgattata    2220
tatataattg atatgcacat atatgcataa cacctaaaca cgtatttttt gcctataacg    2280
cttttttacc agttgtcact tggtttggtg acactagtct ccttccattt tccctgaggt    2340
tggaaatgca atttcaatta ctttgcacct ctcaccagag ttctcagtca attgtttagc    2400 acaaagaat tcataaaag tttgcccttc aaggaaaagt ttaaggaga ataatttatc    2460 cttgtagac acagggaagt gcagggccat tagaactaag catatctatt tatggatgtt    2520
taaatatttc tctttcaatt atgattgtca aactgccttc tagagtctca caaataacag    2580
aagcagaaaa aaatacagtt gtgaaaaaac agtgctgaca gtgaactgaa gaatatgtgc    2640
attcctcatt ggctgcccct tccaatgcat tgttgctgtg caggaataca caggtcaaat    2700
gtaaccaaat ttggggactt ctaggtgaaa ctagaaatgt ggattggtgt gtaagatctc    2760 ctattttaa atattggtct agtgtttttt aaatataaaa tacacagtct ccttctcttt    2820
attggccaga cccaacccct ctaacactag tctatgtact atagtgtact ttaagtcatt    2880
aagtaaagga ctttctactt ccagtccaat caaggttgaa tcccagttac agtgaagtga    2940
aagtgagaag taggacatta gggtaataat tagctacagt aaacaaagaa atcatgattc    3000
catcatgaca aatacacagt aagtgttagg ggctacatgg ggctcattgt taaaatggct    3060
catcatgctg acccatgaga ctgaccatct tgttcaagcg acatcctgtt tttgccactg    3120
gtgcctattt tcccaagact acaagaccag ggggaccac acacctccag ccttctcaag    3180
attatgagtg caccctaccg tgagatacct ctgactttct catgacgatg tgaccaccag    3240
agtccacctg caggtgaaag ataaactata actaaccctt cccccgcttc aggaatcaat    3300
ttcccctctg cagagtataa gaaggccctg ctagaagggc ggggggggctg actcttctca    3360 aaggtcagtc agcctctcct ttttccttct aataaatttt cttctctttg cctgaacacc    3420
caattccttc tctttttctc catgctcgcc ttacagtaag accttcagga gcacttggga    3480
gcaggcggtt ctgtaaattt tccatacctt cccatatatt ccactttcaa tagttgggtt    3540
cctattgtcc taactttcac aagaactatc cattttatgg attcatgtca tattaatcac    3600
tatagattag attttgcatg ccctcccgaa ttcatatgtt gaagccctaa ctcccccatg    3660
tgatgcactt ggaggtggca tctttggagg caaataggtc atgtgagtgg gatatctatg    3720
agtgggatta gtgcccctct aagaaaagct aggagagagc ttgtctatct ttctgccttg    3780
tgaggataca gcagaaaggc aggcacctgc aggccaagag ggagccttca ccggacacag    3840
gatctgctgg cacctggatc ttggtaaatg ttatttgtaa ctgtatgtct gtgagttgct    3900
atgggcagga tgtactggct ggtaaacatt gtttagtaat aagtggatgt ggtttacacc    3960
agatttagga gaatctagga gtggtgaggt aaaatggggt ттggсатттса атттgттgacт    4020 cattatatag ctaaaatatg cctgcttgat gagcttattg taagagatct cacaagtcat    4080
```

| | | | | |
|---|---|---|---|---|
| tttgagcttc | ctagtattga | ggtgctttgc | acaccctctg | ttagtggcct | aagaactgaa | 4140 |
| gataacacat | gtcttgtgct | accaagcagt | aggaggataa | atgaagtttg | ctcttgagat | 4200 |
| ctcagtacct | ctttcatctt | tcaatgcata | cccttctcct | gttgttgtac | tctgtcctct | 4260 |
| gcctgtaata | aagctg | | | | | 4276 |

<210> SEQ ID NO 6
<211> LENGTH: 4955
<212> TYPE: DNA
<213> ORGANISM: Artificial Sequence
<220> FEATURE:
<223> OTHER INFORMATION: 3'arm 4.9kb

<400> SEQUENCE: 6

| | | | | | | |
|---|---|---|---|---|---|---|
| catggcatat | ggaagttccc | aggctagggg | tcgatcagag | ctgtagaccc | cgacctacac | 60 |
| cacagccaca | gcaactcagg | atccaagcca | catctgcgac | ctacaccaca | gctcacggca | 120 |
| atgctggatc | cccaacccac | tgagcaaggc | cagggattga | accggcaacc | tcatggatac | 180 |
| tagtcggatt | tggttctgct | gtgccataat | gggaactcca | ggcctgttta | ttttcttaat | 240 |
| ttgcagcagc | acaatgtaaa | gtgttttctc | atagctatcc | attcatttat | gtccctcttt | 300 |
| actaatgttt | atctcttctt | ttttatcctt | aaggaaatca | tcaatgaact | gaacagggta | 360 |
| aggaacatta | atgatattta | aattatttta | aaattcattc | tttcaaaaat | atattagcta | 420 |
| cacttttag | ttttaacaaa | gagaactcct | gagaaaaaaa | cagtaataaa | ctcaaggtat | 480 |
| caaaatcttt | cttatgatag | tgtgtcaaaa | agtatattct | tgcagttcaa | aagtgttttg | 540 |
| atttagaaaa | acagtatttt | tcctgtgata | tttataccctt | cactgaactt | tcaaaatgac | 600 |
| taatgaattc | tactcataat | tctaaatatt | tattttattg | atttaatttt | gtatctatga | 660 |
| atagacaagg | cattaatatg | aatgaatgaa | tgggtgcaat | tttggactaa | ccaattttt | 720 |
| gcacttatca | ccaaaactga | agaattctt | tattaaaggt | tttataaaaa | aacaatatta | 780 |
| tctgcaccta | gaatgtttta | cataatcaca | gttggtttatt | ctctttcttt | acacatgagt | 840 |
| ttctgggccg | gggatcagat | ccaagctgca | cttgagacct | aagtcacagc | tacttcaatg | 900 |
| gaggaccctt | aacccacttt | gctgggctgg | gtatgaaccc | agcgcttcct | agtgccacag | 960 |
| atcccattgc | accacagggg | aacctctaac | gcatattttt | ttaaaatctg | gtctgtcaga | 1020 |
| ttttagtag | ttttggtatt | gagacaacac | aggtgccact | gaagataaaa | aaatatatct | 1080 |
| tcctaactat | ccttcatact | tgaatgatca | tccttttcttg | gcaggatgct | aggagtgaat | 1140 |
| caactgaagt | aagattcttt | attgtaaaac | tattaaatat | aatgtaagga | aaagaaagaa | 1200 |
| ataaaatcat | ttccttttaaa | tatcctaatg | aaaatgaatg | actaattctt | ttaggtcaaa | 1260 |
| actaagacag | atatctctaa | ttcaaagaga | gaaaaaaaa | aacatacaat | gttatcatct | 1320 |
| gtgagccata | attagctgga | taactaaatc | aatggtatta | tattgagctt | aaattctatg | 1380 |
| gatcatgtca | ctactccctg | tactgctatg | gtcatgaaaa | ctgaacacaa | cattctagat | 1440 |
| ggagaaaatc | cattttgctt | aaatatttat | acaccattga | accaatgctt | catagacttt | 1500 |
| tatttattac | ataatctta | atccaatact | tctgcttaat | agccaaaagc | caagtaaagg | 1560 |
| aaaaaagta | agggtagtta | aaggaaaatg | taggattatt | tacactgatt | taccacaaca | 1620 |
| aataagaatc | cataataatt | tatgtcaagg | gagttcccgt | catggcgcag | tggttaacga | 1680 |
| atctgactag | gaaccatgag | gttgagggtt | cgatccctgc | tcttgctcag | tgggttaagg | 1740 |
| atccggtgtt | gccctgagct | gtggtgtagg | tcgcagacgc | ggctcggatc | ctgcattact | 1800 |
| gtgaccctgg | tgtaggctgg | cagctacagc | tctgattcga | cccctagcct | gggaactttc | 1860 |

```
atatgccgtg ggagcggccc aagaaatggc aaaaagacaa aaaaaacaaa caaacaaaca    1920
aacaaaaatt ttatgttaaa ctcagaaatg cagattaggg aggtaaattc tttggttagc    1980
ctggtaggta ggcttttttc tttccttatc actggctctt accacatatt tctatttctt    2040
ttggcatcta ttttatttga taattattat tttacatttg aatatttgtc ataaaaaata    2100
aattctcttt tcttttctaa gaatcatggc atggaaggcc atgaggtaag acccttattg    2160
taataaactc tacacttaca taacatccat agtatatact ctatgctcta ttttaagaaa    2220
actctcttct caaattgagc aagattgaac ttcccaaaca aggttattat acccaagaat    2280
gtacaatgtt gtgccagata atgttaaaat tagaagagga aatgtgtctt ttaattgata    2340
atcagggaaa atgttattta ttaaaataaa gggtgtaagg caaaatgtgc atgagtgttt    2400
caaatgaaat atgagcctcc aaaaaaaaag aaaaaaaaac ctgtctctac cacctcaggg    2460
tataaactca ctcctgtttg tgagggtagt cttggggaga agaatctgg ttgcagtaat     2520 tacttaggat caatggccta tgctacttaa tccaaaagca tggaaaaaat ccactagccc    2580
acaatatttg gttaatcaac tttcccaaga gatgaatcat ctgttgacta ttaaaatcaa    2640
tcttttaggt atgtacttga gaacaaaaat tatatccata tttaaatata aacgtccgtg    2700
agttagaaaa aaatctaaat agttcaaagt gtagatgttt taaaagctaa tgtaatttta    2760
gttccatacc aaaatttgtt gttgtatttt catgtttcaa tttattccct tcaaagaagc    2820
cccaaggata catgagaata aatatcccac ccgggggttct gggtgcccaa gctcagtagg   2880
gcacttcctt ccaaatttca tatatatttt gcattctact caaccacata tctatgtttg    2940
atttaataaa atgttgtttt ttagtgattg gttattacat tcccacatcc aacatatttt    3000
aaataaaatt gacaacccca aaaaggtacg ttatattggc cctgaatgtt tcattaccaa    3060
ttgctttcat tctaaacaag gagttagcaa cccagtatga aagtgtggaa caaatttcct    3120
tctaattcta aaagtcacag tgttgggaac actgattttc tctctttag caaagggaat     3180 ctagcagttc atcaagtgag gtaaatcatt ttgatgttaa ttcagtatct cagttagaaa    3240
atgtttatga aaacttgttg tgctatgaat gttacacatc ccataaggtc tcatggtaca    3300
ggctctatgt ctacagctct accctaattt taacatacag gctatgagcc caaagatat     3360 aataacgcaa atacttgtca gatgaaatta cagaattgtt tctgcgctaa caattctatc    3420
tggctatcca tggtgcccca ttttttttct ctaattttt tgccttcct aggttttggt      3480 agtactaaat attttatta aaattactat aagagctatg cttctaaatc attaatagaa     3540
acttggtatt tcctgtgcag acatctactg attctaggtt aactgggtac tggaatcctt    3600
tactccttgt taacctaaaa gagaaaaga gcaggcatag aaggtccttt cgtaaacttt      3660
gggagaagaa aatttcaaaa taaacccaac ccagttatgc ggagtttctg ggagatcagt    3720
aaaagtgcat cgaatatttc acatctacct ccaacattct gaataacttc cctgttgaaa    3780
tcagtgagaa gaggaaaggg aatcttgagt acaacctgta ccttgaatta ttcatccttat   3840 ctcagttacc aaggaatggg tgcctaagat caatttatca cagttaagca acatggtaac    3900
tggctaatta gtattcatac cttgagtata aattaataag tcataaaact aacactgcat    3960 gttttttattt tttaaggaag ttgttggcaa tagtgctgag gtgagatata cttactaaat   4020
ttaaaataca ttcacgttat ccaggatgtg ttaaaattta cttgtacttt ttttttttctt   4080 ttttagcaga agcacgttca aaagaagaa gatgtgccct cccaaagcta tctggtaaaa    4140
ttttactaaa agtttatcaa aggcaaatgt accaaggaat gagtatgaat gttgtactga    4200
```

```
tacattattt ctccttctca acctctgcta caccttaata catagtaagc cgtctaacag    4260
actctagatg tttactgatc ccctgcaaaa ataaagctaa caactttttt atcccagggt    4320
ttttgtttgt ttgtttgttt gttttgtctt ttgtcttttt agggccgcac ctgcagcaca    4380
tggaggttcc caggctaggg gtctaatcag agctgtagct gctggcctgc atcacagcca    4440
cagcaatgcc acatccaaac cgcatctgca acctacacca cagctcccag caacgctggg    4500
tccctaaccc actgagcaag gccagggatc aaaccggaac ctcatggttc ctagtcagat    4560
tcgtttccac tgcgccatga tgggaactcc tatcccaggt tattaattca tgctttcatg    4620
agatttgtgt tttatagtct attttttggat ctgaataaca tagtatttt tttatttttt    4680 taattttccc actgtacagc aaggggtca ggttatcctt acatgtatac attgcagtta    4740
cagttttttc ccccacccct tcttctgttg caacatgagt atctagacat agttctcaat    4800
gctattcagc aggatctcct tgtaaatcta ttctaggtgt gtctgataag cccaagctcc    4860
cgatccctcc cactccctcc ccctcccatc aggcaaccac aagtctcttc tccaagtcca    4920
tgattttctt ttctgaggag atgttcattt gtgct                               4955
```

<210> SEQ ID NO 7
<211> LENGTH: 206
<212> TYPE: PRT
<213> ORGANISM: Sus scrofa
<220> FEATURE:
<221> NAME/KEY: PEPTIDE
<222> LOCATION: (1)..(206)
<223> OTHER INFORMATION: amino acid of porcine alpah S1 casein

<400> SEQUENCE: 7

Met Lys Leu Leu Ile Phe Ile Cys Leu Ala Ala Val Ala Leu Ala Arg
 1               5                  10                  15

Pro Lys Pro Pro Leu Arg His Gln Glu His Leu Gln Asn Glu Pro Asp
            20                  25                  30

Ser Arg Glu Glu Leu Phe Lys Glu Arg Lys Phe Leu Arg Phe Pro Glu
        35                  40                  45

Val Pro Leu Leu Ser Gln Phe Arg Gln Glu Ile Ile Asn Glu Leu Asn
    50                  55                  60

Arg Asn His Gly Met Glu Gly His Glu Gln Arg Gly Ser Ser Ser Ser
65                  70                  75                  80

Ser Ser Glu Glu Val Val Gly Asn Ser Ala Glu Gln Lys His Val Gln
                85                  90                  95

Lys Glu Glu Asp Val Pro Ser Gln Ser Tyr Leu Gly His Leu Gln Gly
            100                 105                 110

Leu Asn Lys Tyr Lys Leu Arg Gln Leu Glu Ala Ile His Asp Gln Glu
        115                 120                 125

Leu His Arg Thr Asn Glu Asp Lys His Thr Gln Gln Gly Glu Pro Met
    130                 135                 140

Lys Gly Val Asn Gln Glu Gln Ala Tyr Phe Tyr Phe Glu Pro Leu His
145                 150                 155                 160

Gln Phe Tyr Gln Leu Asp Ala Tyr Pro Tyr Ala Thr Trp Tyr Tyr Pro
                165                 170                 175

Pro Gln Tyr Ile Ala His Pro Leu Phe Thr Asn Ile Pro Gln Pro Thr
            180                 185                 190

Ala Pro Glu Lys Gly Gly Lys Thr Glu Ile Met Pro Gln Trp
        195                 200                 205

<210> SEQ ID NO 8

```
<211> LENGTH: 22
<212> TYPE: DNA
<213> ORGANISM: Artificial Sequence
<220> FEATURE:
<223> OTHER INFORMATION: 5' UTR forward primer

<400> SEQUENCE: 8
tgacaaccat gaaacttctc at                                              22

<210> SEQ ID NO 9
<211> LENGTH: 20
<212> TYPE: DNA
<213> ORGANISM: Artificial Sequence
<220> FEATURE:
<223> OTHER INFORMATION: 5' UTR reverse primer

<400> SEQUENCE: 9
gttcctgatg cctgagagga                                                 20

<210> SEQ ID NO 10
<211> LENGTH: 23
<212> TYPE: DNA
<213> ORGANISM: Artificial Sequence
<220> FEATURE:
<223> OTHER INFORMATION: 3' UTR forward primer

<400> SEQUENCE: 10
aaccatttta tctgaagact ttg                                             23

<210> SEQ ID NO 11
<211> LENGTH: 21
<212> TYPE: DNA
<213> ORGANISM: Artificial Sequence
<220> FEATURE:
<223> OTHER INFORMATION: 3' UTR reverse primer

<400> SEQUENCE: 11
tctcagtcac tgcacacaat t                                               21

<210> SEQ ID NO 12
<211> LENGTH: 3360
<212> TYPE: DNA
<213> ORGANISM: Artificial Sequence
<220> FEATURE:
<223> OTHER INFORMATION: 5' UTR sequence

<400> SEQUENCE: 12
tgacaaccat gaaacttctc atctttatct gtcttgcagc tgttgccctt gccaggcctg     60
tgagtatggt agagaattta gaagcttcta gattcttgat tgaaattacc tgatatcaaa    120
cacaagaaac tgaggataat aatcttaaaa gtattgaatg atctctaatt accttttgaa    180
gccttgatat taaaactgta gaaatccttc acatcttgat cattattaca tagttcattc    240
aaagtcatca ctccaaataa aatctgagtt gaaatataaa tgcctcacag taaaaaaata    300
aaaacaaaaa atgaaaagaa aagaaaaagg aataatgtat ttaacaacat agtaaataga    360
atcaatgagt gttattacgc tctttgcctg ggtccaataa agaattagca tatatttaaa    420
catacaagtc catgattttt tctgtggaag ggctcatttg tgccttatat aagattccag    480
gtatcagtga tatatcattt ggtatttgtc tttctctttc tgacttactt cactcagtat    540
gagagtctta gttccatcca tgttgctgca aatggcatta tgccattctt tttatggctg    600
agtagtattc cattgtgtgt atatactaca tcttccgaat ccaatcatct gttgatggac    660
atttgggttg tttccatgtc ctggctattg tgaatagagc tgcaatgaac atgtgggtgc    720
```

```
atgtgtctct ttcaaggtaa gttttgtctg gatatatgcc caagagtggg attgcagggt    780
cacatggtag ttctatgtgt agatttctaa ggtatctcca aactgttctc tatagtggct    840
gtaccagctt acattcacac caacagtgca ggagggttcc cttttctcca cccccccca    900 gcatttgtta tttgtggact tatcaatgat ggccattctg actggtgtga ggtggtatct    960
tgtggtagtt ttgatttgca tttctctaat aatcagggat gttgagcatt ttttcatgtg    1020
cttgttggcc atctgtacat cttcctttga gaaagtctat tcaggtcttt tgcccatttt    1080
tccattgggg tgttggcttt tttgctgttg agttgtataa gttgtttgta tattttagag    1140 attaagcccct tgtcagttgc atcgtttgaa actattttct cccattctgt aagttgtctt    1200
tttgttttct tttgggtttc ctttgctgtg caaaagcttg tcagtttgat gaggtcccat    1260
tggtttattt ctgctcttat ttctgttgct tgggagatt gacctgagaa atattcatg    1320 atgttgatgt cagagagtat tttgccaatg ttctcttcca ggagtttgat ggtgtcttgt    1380
cttatattta agtcttttcag ccattttgag tttattttttg tgcatggtgt gagagtgtgt    1440
accagtttcg ttaattttca tgcagctgtc caggtttccc agcaatgctt gctgaataga    1500 cttcttttt cccactttat gttcttgcct cctttgtcaa agattaattg aacctttcca    1560
tagaaaagaa aatcatgaat ttggagaata aacttgtggt tgccaaaggg gagggagagg    1620
gagtggtgtg gttgaggagc ttggggttaa tagatataaa ctattgcctt tggaatggat    1680
tagcaatgag accctgctgt gtagcactgg gaactatgtc cagtcactta tgatggagca    1740
tgataatgtg cgaaaataga atgtgtacat gtatgtgtaa ctgggtcccc atgctgtaca    1800
gtagaaaaaa aatgtgttga gaaaataact attacaaaaa tgagaattat gaaataaata    1860
aataaataaa caaacataca tgtccaatat tttcttacca aatataacag aatgccgcct    1920
attgcagtgt atcctacttt tggaacctaa gtcaaaccct cacatgagat gactcatatc    1980
aaccaatatt tcccaaggtg tagaaaactg agttattctg ctgattcaga gatttaatta    2040
ttatggtcct tgtagacaag gaaactaggt aatataaatt aaaatcactt ttcttctcaa    2100
aaaaaaaaaa gattcagtta cttatgtaga gcaaaaatta ttctgttccc ttgtgatata    2160
tagctagcaa agatggaagg gataaactgg aattgcttga caaagaaacc atccagataa    2220
aataataatc ttggatattt gggcattgta attattaaat ataggtgtaa aatttttttgg    2280 aattctgaga tattctatga tgagactcct atttcctaaa ttttttgtttg gataatgcag    2340 gatcactaat aacctaactt tccttttttt tttttttttt tttttttgctt tttagggcca    2400 tacccacagc atatggaggt tctcaggcta ggagtcaaat cagagctgcc ggtggcctaa    2460
ccacagccac agcaactttg gaatcaaatc tgagctgtgt ctgggatgta ccccacagct    2520
cacagcagtg gtggatcctt aacccactga gtgaggccag ggatcaaacc cacctcccca    2580
taaacactat ttagctttgt taccccagac cccctatggg aactccaaac caacctgtta    2640
gacactagag cttttctat gctacacctt aagcaccaat aggaagaaaa tctatgatag    2700
caagttacaa gaaaaaggat ccaacttttt cagaaaagtg tcactgttag tcttttttaca    2760 aaagaaatgg gtatagtttc cccagcaaac agattctata attctattcc aagaaaacat    2820 cattttttaat gctaccattt aacaaacata atcttgttc ccacagttca aatgtagatt    2880
gagttaaatt tttatataat taactgatta taaaaataaa atccagaaaa tgtttaatga    2940
agaaaagtat atattttgtt tcaaaaattc ataaatagtta ttttttagaac taccatgtaa    3000 tataaatagt tcagaaaaat taaatttatc attttggatc aagacaaatt aatttttttt    3060
```

```
ttcagtctttt ttacacatttt ttctcagttc tccatcatac cccaatgaca ggaaatcatt    3120
tacttttctg tgattttat caagaaaata accatttttt ttcttcccag ggaaacttgg       3180
ggtcagatga atttagctat taaaatacac atcattttta aatagcaaat gttacattta     3240
cagtattcta tttgttttgt gatattatta tcatattttg attgcatttt gttttctttt     3300
tgtttgtttt taaattcttg cattgttttt cacagaaacc tcctctcagg catcaggaac    3360
```

```
<210> SEQ ID NO 13
<211> LENGTH: 303
<212> TYPE: DNA
<213> ORGANISM: Artificial Sequence
<220> FEATURE:
<223> OTHER INFORMATION: 3' UTR sequence

<400> SEQUENCE: 13 aaccattttta tctgaagact tgactgttc ttttagaaca gggaaatcgc aaatcgaagt      60
caatcttcct tcttgaattc tttactctat attagatagc atataatcct tttcctttgg   120
caaagttgtc ctaacagttt agtgtctaaa tttcagttgt atcatgccag taggaagacc   180
actgaatcag agggaattaa aagtcttac taaatttcaa tatggaaatt ttgtttaaaa    240
agcctttgaa ttgcttctcc tgtaagtgcc atcatttcaa ataattgtgt gcagtgactg   300
aga                                                                 303
```

```
<210> SEQ ID NO 14
<211> LENGTH: 22
<212> TYPE: DNA
<213> ORGANISM: Artificial Sequence
<220> FEATURE:
<223> OTHER INFORMATION: 5' UTR probe forward primer

<400> SEQUENCE: 14
tgacaaccat gaaacttctc at                                              22
```

```
<210> SEQ ID NO 15
<211> LENGTH: 21
<212> TYPE: DNA
<213> ORGANISM: Artificial Sequence
<220> FEATURE:
<223> OTHER INFORMATION: 5' UTR probe reverse primer

<400> SEQUENCE: 15
ctaagactct catactgagt g                                               21
```

```
<210> SEQ ID NO 16
<211> LENGTH: 551
<212> TYPE: DNA
<213> ORGANISM: Artificial Sequence
<220> FEATURE:
<223> OTHER INFORMATION: 5' UTR probe sequence

<400> SEQUENCE: 16
tgacaaccat gaaacttctc atctttatct gtcttgcagc tgttgccctt gccaggcctg      60
tgagtatggt agagaattta gaggcttcta gattcttgat tgaaattacc tgatatcaaa   120
cacaagaaac tgaggataat aatcttaaaa gtattgaatg atctctaatt accttttgaa   180
gccttgatat taaaactgta gaaatccttc acatcttgat cattattaca tagttcattc   240
aaagtcatca ctccaaataa aatctgagtt gaaatataaa tgcctcacag taaaaaaata   300
aaaacaaaaa atgaaaagaa aagaaaaagg aataatgtat ttaacaacat agtaaataga   360
atcaatgagt gttattacgc tctttgcctg ggtccaataa agaattagca tatatttaaa   420
```

```
catacaagtc catgattttt tctgtggaag ggctcatttg tgccttatat aagattccag      480
gtatcagtga tatatcattt ggtatttgtc tttctctttc tgacttactt cactcagtat      540
gagagtctta g                                                           551
```

<210> SEQ ID NO 17
<211> LENGTH: 3735
<212> TYPE: DNA
<213> ORGANISM: Artificial Sequence
<220> FEATURE:
<223> OTHER INFORMATION: 5' UTR sequence

<400> SEQUENCE: 17

```
aggtgacact atagaagagc tcgaggatcc tgaattggaa ataaaataag tcagttatcc       60
tggatgcatt ctcaggaaaa gacaagagcc gggtattgta aggcagtgga gaatacttgt      120
tctcagcccc ttggataaat cagagtaaat agaaaatact agtactttttt tgacattgat     180 gtaatgcagt cagcaaggac gatactatcc aaagaggagt ttaacatgga aaactatagc      240
cttgtctatc cccagtatgg aaagcctgag ccactgcgaa atttctttta accccaaata      300
atgttcctac catatgactg taaattggct gtgaatatca ctatggattt attatttat      360 ttttaaattt ttttggtctt ttttcttttt agggctgcac ccatggcata tggaggttcc      420
caggctaggg gtcgaattgg agttgtagct gccagcctac accacagcca cagcaatgcc      480
agatctgagc tgtgtctgca acttacacca cagctcatgg caacaccaga tcattgaccc      540
cttgagtgag gccagggatc gaacctgcaa cctcatggtt cctagtcaga ttcatttccc      600
ctgcgccaca atgagaattc cagaatttttt ttaaatatat agtgtgatac ctttctgtaa     660
acaagcagtc acaatcaaca attttttaaa tccagctcta tgtatagata ttttattcag      720
catgcaattt ttttcctaaa attaacaatg ccagttaatt ctaggattat atttcagact      780
ggaaagaaag tttttttttc cttttattta cttactttaa aaggtggaaa attggagtta      840
tggttgattt ttgggggggg ggagtattta aaaattgtat tcttaaataa aaattattct      900
tgaataatta ttttttaatta agaaatctaa caattaaatt aatgaatact atcacaacac      960
atatacccaa aataaagcaa gcagaaaatt atttggtgta gttaaaatac taccaaagtt     1020
tataaggcaa ttgtatttc ttttttggtta aaaaaaagat cagatcacat ataaggtaac     1080
ttactccaca agtaactta cttagaatac ttagaataaa tacttagaag acttagaata      1140
aataataggg aataaataga gttttaaaag gtgaaataga tgatgaaatc ttctcatggt     1200
ctagtacaat tataaaaatt aaaaattttt gatgatttta tttttgtctca agaatttccc    1260 ttacaggtat tgactttttc aaaagctgta aaggaaattt tattgctata ttaatctttc    1320
caattatcca tttaacttaa aaagcatgtt cttataataa ccataaatat ggaatttta      1380 tgtatcttaa ttttgaataa tgtcattcca tttcctgtat aatttggtgt catagcatga     1440
atcactcctt tgttgaaaac tctcctcaga atttcttggg agaaaattgg acagaaaatt     1500
aatttcctct tgagagaat tcttagaatt taaatgacac tattggttga actgaaacca      1560
caaaattagc attttactaa tcactaggtt taaatatttg tgaaacaaag agatctgcca     1620
ccatcttgat catcagctca gcttgcttct tctttccggt cttgggttca aggtatttca     1680
tttacatata gcaaaatgtg atatattatg atttcaatct gtctaatttt tcactcctca     1740
ctaaaaaata tgcactggta acttttctgt gtgattccaa atattgatac cttttaatga     1800
tatactggtg gcttaaaaat gcatttgcaa atgtcgatgc catctatctc agagctttag     1860
```

| | |
|---|---|
| ttgaaaaata atagttttat aaagaccaaa ttttttttgcc aaattttatg aaaacttatt | 1920 |
| atgtgaaata atttataatc tttttaaaga tcatagtgag gatcatttct ggtagaatat | 1980 |
| ttcaagacca ttttttattcc atgtcattag gttaataaaa ttaattctat aaaggatatg | 2040 |
| ccaatgatat acacagatat aaatgactac ttttaaaag atggttagat ttggatattt | 2100 |
| ggaaaaatgc aaatgaataa aaccagtaaa ctcattttgg atttataaat atgtcttcct | 2160 |
| tacaaatgca gttagattct acaatatgta gactgaaaca gtatgtataa ataagctga | 2220 |
| ttagtttgtt ggctaatgta taaacaaatt gcatgtatat tatgactttc ttttcctaat | 2280 |
| ttctctggaa accagtttcc ccaggacata agttctaagt atctctgggt tcttgtaatt | 2340 |
| tgatggaact ctagaagtca cacatgataa gacatcagaa tcttatgatt ctgctcaatg | 2400 |
| aagtcgtctt tatgcagtca tgtcatggat atagcaacgt agaaaaacat aacataatag | 2460 |
| ctagacttta aaaaaaaatt gatggaggtt aaatgtttct acataatatg caccaacagt | 2520 |
| gttttttccca aagacgctga aaaagcagga ttctctaaca tagacctaga aaacacctt | 2580 |
| caaaaaattg cagatggga gttcccgttg tggctcagtg gttaacaaat ccgactagga | 2640 |
| accatgaggt tgcaggttca atccctggcc ttgctcagtg ggttaaagga tctggcattg | 2700 |
| atgtgagctg tggtgtaggt cgaagacgtg gcttggatcc cacgttgctg tggctctggt | 2760 |
| gtaggctggt ggctacagct ctgattcaac ccctagcctg ggaacctcca catgccgtgg | 2820 |
| gagcggccca aaaaaaggca aaaagaccaa aaaaaatttt ttttcagat aaaattaaat | 2880 |
| gccagttccc tgtgcctttt agtttattat caattttag caaatctgat ggtctaagag | 2940 |
| gaaatattta aaataattaa ttgtagtatt cttaaattta gtagtattta atattaatg | 3000 |
| tttatgtatt cctctgacaa aaccctatta ccacttcaag gatcaaatgt tttgttttag | 3060 |
| agggtgatac tggtgtttct tatctcatat aagcactaag caagataatt tgaatgataa | 3120 |
| attttcttg tgagtaaatt ttctgtcaga cctaaatttt tattttgttt tcttatatag | 3180 |
| gtgttgacaa ccatgaaact tctcatcttt atctgtcttg cagctgttgc ccttgccagg | 3240 |
| cctgtgagta tggtagagaa tttagaagct tctagattct tgattgaaat tacctgatat | 3300 |
| caaacacaag aaactgagga taataatctt aaaagtattg aatgatctct aattaccttt | 3360 |
| tgaagccttg atattaaaac tgtagaaatc cttcacatct tgatcattat tacatagttc | 3420 |
| attcaaagtc atcactccaa ataaaatctg agttgaaata taaatgcctc acagtaaaaa | 3480 |
| aataaaaaca aaaaatgaaa agaaaagaaa aaggaataat gtatttaaca acatagtaaa | 3540 |
| tagaatcaat gagtgttatt acgctctttg cctgggtcca ataaagaatt agcatatatt | 3600 |
| taaacataca agtccatgat ttttttctgtg gaagggctca tttgtgcctt atataagatt | 3660 |
| ccaggtatca gtgatatatc atttggtatt tgtcttttctc tttctgactt acttcactca | 3720 |
| gtatgagagt cttag | 3735 |

<210> SEQ ID NO 18
<211> LENGTH: 2179
<212> TYPE: DNA
<213> ORGANISM: Artificial Sequence
<220> FEATURE:
<223> OTHER INFORMATION: 3' UTR sequence

<400> SEQUENCE: 18

| | |
|---|---|
| aatacgactc actatagggc gtcgactcga tccactgcat ggaagaatgt gatttctcca | 60 |
| tttttccttgc agagtagata tctcttgtga tgctaatagc catgtcagaa gtgaatagaa | 120 |
| tgcttctttt tttcagagat tctaaagagc aatttcccat atcctgttgc tatttcattc | 180 |

```
tctctagcct ctccaccagt tctaccagct tgatgcctat ccctatgcta cctggtatta     240
tcctccacaa tatattgctc acccattatt caccaacatc cctcaaccca ctgcccctga     300
gaagggtgga aaaactgaga ttatgcctca gtggtggtaa gttcatttta atgactgtat     360
attgatgttc taccaaagga aataaaagaa aacttcttaa agaacatacc ataaaaacag     420
atttagaata aacatgacaa aatcaatatc tagagcgtcg tagtagaatt ttccaaaatg     480
ggaaattggc aggacgttct gatatctgca gctaatgtta atccactact caggaacttg     540
tggagcagcg ctctctgttc tttgagattc attctgatga agtcaggaaa aagttttcta     600
tccaaagcaa aaacacagta atttcacttt atcctcctta caattttact aatctctaaa     660
ggcttttctt ttggttatat atacccatga tatacattac aattcagtgt ggggaataaa     720
gcacagattt tggcatccaa aagtcccaaa tccaaatcct gaccttttt gcttacttaa     780 aataatgcat taatgcttat ttttataatt ctgaaggtga ttaaagacaa taatctgtta     840
agcatagtgc tgggaagata catagcagtc agttttatt gatttagtaa aattgtactg     900
ctgactacct tcatcacatg attttaagaa ttttgtttt ttcagaagaa ttaagtgaat     960
tctcaggaac tccacaatta tggcctttgg taagttggaa atcatttgtg gaaccattga    1020
tcctcttttc gtttaaagac tcattacaaa gataggactg tagactataa agattttttt    1080
tcctgtagtt gagctccttg tggacacatt agcacttaga taataattaa attggcttgg    1140
acatttgcaa atgtttgttt cataattata ctatatgtaa atagcaatca aattagataa    1200
ttttaatgaa tataatttat tatattgaac ccctatacaa gtataggagc atgaatgcta    1260
ctaattttcc atcaagatgt gaccttgaga tgctggtaaa ctcaacagtg ggattctatt    1320
ttttatgatc actacaataa aaatccttag caagtcatgt gataaaacca agtatttgtt    1380
tctcaacaag aaaacagact ttaacgtcta cagacttgtt ttaattaact tcatccattg    1440
tactggtgtt tccgattgta tgtcagtaga ggtgtgtgtg tgtgtgtgtg tgtgtgtttt    1500 cccttctag tggtggaaat ttcccttcca actgattgaa ttaaggaaaa tgacaaaaca    1560
tatgggaaag gtttttcttt gaattccttg gccatatttt ctctgttact gcaaaagaaa    1620
atactaccta gcaataaatt gtctatataa cttaaaatta tcaggataaa tgggtacata    1680
tgtcagtcac aggaaagaac aaataacttt gtgagtttca tcttaaaatg aagagaaaat    1740
gattattcaa atgcatcata acagtgtctc ttccattcaa aacatgtaat ataaccaacc    1800
acatatttct ttttctattt acagatgtga ctgaaaatac catgcttgaa atttctcctc    1860
tccatctacc atgtagaacc attttatctg aagactttga ctgttctttt agaacaggga    1920
aatcgcaaat cgaagtcaat cttccttctt gaattcttta ctctatatta gatagcatat    1980
aatccttttc ccttggcaaa gttgtcctaa cagtttagtg tctaaatttc agttgtatca    2040
tgccagtagg aagaccactg aatcagaggg aattaaaagt ctttactaaa tttcaatatg    2100
gaaattttgt ttaaaaagcc tttgaattgc ttctcctgta agtgccatca tttcaaataa    2160
ttgtgtgcag tgactgaga                                                2179
```

<210> SEQ ID NO 19
<211> LENGTH: 6357
<212> TYPE: DNA
<213> ORGANISM: Artificial Sequence
<220> FEATURE:
<223> OTHER INFORMATION: 3' UTR sequence

<400> SEQUENCE: 19

```
aaccatttta tctgaagact tgactgttc ttttagaaca gggaaatcgc aaatcgaagt      60
caatcttcct tcttgaattc tttactctat attagatagc atataatcct tttcccttgg    120
caaagttgtc ctaacagttt agtgtctaaa tttcagttgt atcatgccag taggaagacc    180
actgaatcag agggaattaa aagtctttac taaatttcaa tatggaaatt ttgtttaaaa    240
agcctttgaa ttgcttctcc tgtaagtgcc atcatttcaa ataattgtgt gcagtgactg    300 agattttct  tccttctttt caataaatta cattttaagg cacaactcct atttttgtc     360 attattccat tcagcagaat ttgcacaatc ctgttaacag tctttatgcc tgtaacattt    420
tattttcact aaattttat  tacactttca accacaattc aatgaacaaa atggtaaatc    480
ttcatgccta gctgatgctg acaggttata agctgggtct aggatctttc atttgaagtc    540
acctgtctat aggatattct ccatgagaac ataggtgtgg ctgcagagaa gaacagtggt    600
atgacagttg cgggtgcact gggaatttga aaaacatggc taagctgttt atttatgtca    660
ccagaacctg tttgagccaa actcatttga ttatttgatt attatacact tacttttata    720
attaggtaga ttagataata aacatttaat aggttagacc atggcataca gtaacacaat    780
actcagtgtc ctcccgaact ccaatgaaga gttattctc  aaaatgacaa tagtcgcttg    840
cattaatacc ctcaaaaccc tgctggaatt tactttccag agtttattcc agggtcccca    900 acaaaccta  tctgctgtga ctcttttaaga aacttctttc caccaggtca taaaatacag    960
gtggcaaggt ctcttgtacc acaacctaaa cgacctattt agttagcagt tctgtctctt   1020
atcgattata tatataattg atatgcacat atatgcataa cacctaaaca tgtattttt    1080 gcctataacg cttttttacc agttgtcact tggtttggtg acactagtct ccttccattt   1140
tccctgaggt tggaaatgca atttcaatta ctttgcacct ctcaccagag ttctcagtca   1200
attgtttagc acaaaagaat ttcataaaag tttacccttc aaggaaaagt ttaaaggaga   1260
ataatttatc ctttgtagac acagggaagt gcagggccat tagaactaag catatctatt   1320 tatgatgtt  taaatatttc tctttcaatt atgattgtca aactgccttc tagagtctta   1380
caaataacag aagcagaaaa aaatacagtt gtgaaaaaac agtgctgaca gtgaactgaa   1440
gaatatgtgc attcctcatt ggctgcccct tccaatgcat tgttgctgtg caggaataca   1500
caggtcaaat gtaaccaaat ttggggactt ctaggtgaac tagaaatgtg gattgtgtgt   1560
aagatctcct attttaaat  attggtctag tgttttttaa atataaaata cacagtctcc   1620
ttctctttat tggccagacc caacccctct aacactagtc tatgtactat agtgtacttt   1680
aagtcattaa gtaaaggact ttctacttcc agtccaatca aggttgaatc ccagttacag   1740
tgaagtgaaa gtgagaagta ggacattagg gtaataatta gctacagtaa acaaagaaat   1800
catgattcca tcatgacaaa tacacagtaa gtgttagggg ttacatgggg ctcattgtta   1860
aaatggctca tcatgctgac ccatgagact gaccatcttg ttcaagcgac atcctgtttt   1920
tgccactggt gcctatttc  ccaagactac aagaccaggg gggaccacac acctccagct   1980
ttctcaagat tatgagtgca ccctaccgtg agatacctct gactttctca tgacgatgtg   2040
accaccagag tccacctgca ggtgaaagat aaactataaa ctaaccttcc cccgcttcag   2100
gaatcaattt cccctctgca gagtataaga aggccctgct agaagggcgg ggggctgac   2160 tcttctcaaa ggtcagtcag cctctccttt ttccttctaa taaattttct tctctttgcc   2220
tgaacaccca attccttctc ttttttctcca tgctccccctt acagtaagac cttcaggagc   2280
acttgggagc aggcggttct gtaaattttc catacctttcc catatattcc actttcaata   2340
gttgggttcc tattgtccta actttcacaa gaactatcca ttttatggat tcatgtcata   2400
```

-continued

```
ttaatcacta tagattagat tttgcatgcc ctcccgaatt catatgttga agccctaact    2460
cccccatgtg atgcacttgg aggtggcatc tttggaggca ataggtcat gtgagtggga     2520 tatctatgag tgggattagt gcccctctaa gaaaagctag gagagagctt gtctatcttt    2580
ctgccttgtg aggatacagc agaaaggcag gcacctgcag gccaagaggg agccttcacc    2640
ggacacagga tctgctggca cctggatctt ggtaaatgtt atttgtaact gtatgtctgt    2700
gagttgctat gggcaggatg tactggctgg taaacattgt ttagtaataa gtggatgtgg    2760
tttacaccag atttaggaga atctaggagt ggtgaagtaa aatggggttt ggcattcaat    2820
tgttgactca ttatatagct aaaatatgcc tgcttgatga gcttattgta agagatctca    2880
caagtcattt tgagcttcct agtattgagg tgctttgcac accctctgtt agtggcctaa    2940
gaactgaaga taacacatgt cttgtgctac caagcagtag gaggataaat gaagtttgct    3000
cttgagatct cagtacctct ttcatctttc aatgcatacc cttctcctgt tgttgtactc    3060
tgtcctctgc ctgtaataaa gctgttctgt tagtgtaaac tgtatgggtc tcctttaact    3120
atcaaaaatg ttaggtcttg tgtgattacc acctcgctgt aatatacagc aaaaaaaaaa    3180
aaaaaaaaaa aaaggagaat tcatctgcaa gttctctctc atctcctgct tctcattctg    3240
aaattttcac ctcagtgggg gctaaaacta tgcatataac agtagcatta accaactatt    3300
acagtttctg aggaaacccg gtcctgtgct atagtacaca atcccattca agtccaacag    3360
caaagaggtg agtctgcatt gatgaggtcc caaccacagg gaaaaggaag aagacaggca    3420
atatactgaa tgcacacatc acaatgaatc accacagata cttacttcca ggctaaggga    3480
aagaatatcg ctagttcccc agcactttct cacattttct gtcaagttgt accttccctc    3540
agataaccaa tagtctagct tatcacacaa gaatttaatc gatcattaga ttctaataaa    3600
ttccacttat tggattacat attccattat attttggcct gattactgtc attcaatgtt    3660
atttatataa aattcaccct tgtttttttg tggcagtaac tcattcattt caactgcagt    3720
atgatatccc attccacttt agaccatgac ttatttatac aaaatacatt tatacaaaat    3780
acaaatttat acaaaataac gtaaatgtta attcacattt atgttgattt tagtttaggg    3840
tattagcatt gttaggagta ttgggtaaat gttttagaa tacatgaa agcatattat        3900 ggtttccttt tggttgtata cctaagagaa gaaatgttag ttataatata agcagatgtt    3960 tattttgac aaagactcat aatacttcc gagttgcttg aaccatttta tatttatttt       4020
aacattacct agcatttatt cagtttgctt attttgtaa atacttggtt ttaccaattc      4080
ttctcattca gctattctgg aggttgtgtc atgatatctg gtattttaa cttgcatttt      4140 ccagagaaat aatggtattg aacatctttt catatattta ttgacaatta aaataacctc    4200
tttggtgaag tgcccattca aagatattgc ttgtgcacta ttatattagt tgcctttgtt   4260
attgaaatat gcccaattaa attttggaca atttggggac tggattcaga caaaaagttc    4320
tgctggccat gtcaggtttg agatattaat tagatactcc gatgtggaga agaatgcagt    4380
tgagcacttg aatttggagt tcaggaaaaa ataagtttga ggacatacat gtggaagctt    4440
caagcccatg aatggactta agtcatgga atcaaacaac atcaatcata gtaaggctaa      4500
tccctagggt attccacaca ttgcatgttt ggaaaaggag aaaatgccag aagagacgat    4560
gcaaagaaat aactggtgag ttaagaggga atcaagggc ttatcaggct taggatttca     4620
aataaaattt gcgatatttc aaaaaaaaaa aaaaaaaaa ggaatgatca actgaccaa       4680 atagcactga tagtttgggt aaaataaaca tagattggta aaatgaatgt tgttggtaat    4740
```

```
cttgaaaaaa gtggttacca taggggtaaa gctcaatggg aacaggttga tgagagaata    4800
ccatgtgaaa caatagacac agtagtttgg acacttcctt tctgatggtt accatagagc    4860
agtctaaagt actgccaagg atggaatttt ttctttaaag atgggagata ttatagccta    4920
agtatggctt gcacttgatc ctgaggtaag gaaaacactg aggatgcagg aaagatgaaa    4980
ttactgctag aaacaagtcc ttgtgtaaac acaaggggag ggaatcaagt ttacaaatgt    5040
aggagttgtg taaccaagca ggaccctgtg aagccttccc acagtggatc cacactcttg    5100
tcctctgcct gcattttgt ctatagaaaa actttagtca aagaatcagt ttgatcagag     5160
aagtgagaaa atacagagaa aaaggaatac agtcaagcaa gacagagtaa taatagttta    5220
gccactcagc aatgtcaagg acttatggtt cttcctcatg gactatagat aatatgctga    5280
gccatgtcct tggaacggtt ttgcaggtgc tcaaacccct accaggcgga agaagtcaac    5340
tgcatgctgc ccacaaacat gtagacccca gaccagttgg aaacagaagg ttgatgatgc    5400
tgactcccaa ttacctcatc accaaacagt taggaaaata tccaagggct gatcatgccc    5460
ggctccttga agagtaagag taagagtcct caccactcct ccaagaggca cacagtcctc    5520
gaagcactag cctgctgtgt accctctgcc tggcaattaa agctacttt gccggtttcc     5580 acatttctat ttggcgtcag tgtatagagg cagccgatac ttcggtgata gttggtagac    5640
agataattca ttgcaatgaa aaaattactc cacagacaga gacaagggat atcagagctt    5700
cacataagtc tactctcttg ggcattagtg gctaaaacaa catccttcag ctcattctca    5760
ttgtgacact ggcactggct gctctagtgt aagtgaggaa tgtggagcca cacggacacc    5820
catcctgcac tgtgtggggt gctattcaca ttaaaacttc aataaaaccc tttcaactga    5880
ctgtgttata gatgcaaaaa ctgaatcttt gaaagcctaa cttatacagc accatttagc    5940
caccatgtta cagagccgtg attcagattt tacattggaa gccttcttat ctaggaggat    6000
cataaaattt aacatccaat gcagatactt ttgagagtga aaggcacaag tataatagtt    6060
cagctgagat aagaggtata aaccaagact ttctagagta tattcagcat tagatcaccc    6120
tgccttttcc tccattttg atataattta gtactcaagt caaagcattc tactcaattt     6180
caatttttcc gtggctattt ttaacattaa taataacttt aagttaacta ataaagaggc    6240
cagttaggtt tggaaaatta taataaaaac aggaaaactt aaatatgcct aaggattaat    6300
ttattgaaat gactggttag gaaattataa ttccataaat tattttata catattt        6357
```

<210> SEQ ID NO 20
<211> LENGTH: 21
<212> TYPE: DNA
<213> ORGANISM: Artificial Sequence
<220> FEATURE:
<223> OTHER INFORMATION: sequencing primer

<400> SEQUENCE: 20

```
taacgaatcc aactaggaac c                                                21
```

<210> SEQ ID NO 21
<211> LENGTH: 21
<212> TYPE: DNA
<213> ORGANISM: Artificial Sequence
<220> FEATURE:
<223> OTHER INFORMATION: sequencing primer

<400> SEQUENCE: 21

```
tccttctcca accctatatt c                                                21
```

```
<210> SEQ ID NO 22
<211> LENGTH: 21
<212> TYPE: DNA
<213> ORGANISM: Artificial Sequence
<220> FEATURE:
<223> OTHER INFORMATION: sequencing primer

<400> SEQUENCE: 22
tgagagggga atagaaagaa c                                             21

<210> SEQ ID NO 23
<211> LENGTH: 22
<212> TYPE: DNA
<213> ORGANISM: Artificial Sequence
<220> FEATURE:
<223> OTHER INFORMATION: sequencing primer

<400> SEQUENCE: 23
tatcaatagg tctcagaaga tc                                            22

<210> SEQ ID NO 24
<211> LENGTH: 20
<212> TYPE: DNA
<213> ORGANISM: Artificial Sequence
<220> FEATURE:
<223> OTHER INFORMATION: sequencing primer

<400> SEQUENCE: 24
tagacttcga gtttggaggg                                               20

<210> SEQ ID NO 25
<211> LENGTH: 22
<212> TYPE: DNA
<213> ORGANISM: Artificial Sequence
<220> FEATURE:
<223> OTHER INFORMATION: sequencing primer

<400> SEQUENCE: 25
tataaggcac aaatgagccc tt                                            22

<210> SEQ ID NO 26
<211> LENGTH: 22
<212> TYPE: DNA
<213> ORGANISM: Artificial Sequence
<220> FEATURE:
<223> OTHER INFORMATION: sequencing primer

<400> SEQUENCE: 26
aaatgctcaa catccctgat ta                                            22

<210> SEQ ID NO 27
<211> LENGTH: 21
<212> TYPE: DNA
<213> ORGANISM: Artificial Sequence
<220> FEATURE:
<223> OTHER INFORMATION: sequencing primer

<400> SEQUENCE: 27
tattccgtgt tcatggattg g                                             21

<210> SEQ ID NO 28
<211> LENGTH: 21
<212> TYPE: DNA
<213> ORGANISM: Artificial Sequence
<220> FEATURE:
<223> OTHER INFORMATION: sequencing primer
```

-continued

```
<400> SEQUENCE: 28
aagtattctc cactgcctta c                                              21

<210> SEQ ID NO 29
<211> LENGTH: 21
<212> TYPE: DNA
<213> ORGANISM: Artificial Sequence
<220> FEATURE:
<223> OTHER INFORMATION: sequencing primer

<400> SEQUENCE: 29
tgtgagtatg gtagagaatt t                                              21

<210> SEQ ID NO 30
<211> LENGTH: 22
<212> TYPE: DNA
<213> ORGANISM: Artificial Sequence
<220> FEATURE:
<223> OTHER INFORMATION: sequencing primer

<400> SEQUENCE: 30
ctattgtgaa tagagctgca at                                             22

<210> SEQ ID NO 31
<211> LENGTH: 21
<212> TYPE: DNA
<213> ORGANISM: Artificial Sequence
<220> FEATURE:
<223> OTHER INFORMATION: sequencing primer

<400> SEQUENCE: 31
gtgtgagagt gtgtaccagt t                                              21

<210> SEQ ID NO 32
<211> LENGTH: 21
<212> TYPE: DNA
<213> ORGANISM: Artificial Sequence
<220> FEATURE:
<223> OTHER INFORMATION: sequencing primer

<400> SEQUENCE: 32
tgttcccttg tgatatatag c                                              21

<210> SEQ ID NO 33
<211> LENGTH: 21
<212> TYPE: DNA
<213> ORGANISM: Artificial Sequence
<220> FEATURE:
<223> OTHER INFORMATION: sequencing primer

<400> SEQUENCE: 33
cttgttccca cagttcaaat g                                              21

<210> SEQ ID NO 34
<211> LENGTH: 20
<212> TYPE: DNA
<213> ORGANISM: Artificial Sequence
<220> FEATURE:
<223> OTHER INFORMATION: sequencing primer

<400> SEQUENCE: 34
tagatacctc caccaagagc                                                20

<210> SEQ ID NO 35
<211> LENGTH: 20
```

```
<212> TYPE: DNA
<213> ORGANISM: Artificial Sequence
<220> FEATURE:
<223> OTHER INFORMATION: sequencing primer

<400> SEQUENCE: 35
ttctcaggtt tcctgaggtg                                              20

<210> SEQ ID NO 36
<211> LENGTH: 22
<212> TYPE: DNA
<213> ORGANISM: Artificial Sequence
<220> FEATURE:
<223> OTHER INFORMATION: sequencing primer

<400> SEQUENCE: 36
gtgcacattt acatactgat ag                                           22

<210> SEQ ID NO 37
<211> LENGTH: 23
<212> TYPE: DNA
<213> ORGANISM: Artificial Sequence
<220> FEATURE:
<223> OTHER INFORMATION: sequencing primer

<400> SEQUENCE: 37
atcatcaatg aactgaacag ggt                                          23

<210> SEQ ID NO 38
<211> LENGTH: 21
<212> TYPE: DNA
<213> ORGANISM: Artificial Sequence
<220> FEATURE:
<223> OTHER INFORMATION: sequencing primer

<400> SEQUENCE: 38
ttgagaccta agtcacagct a                                            21

<210> SEQ ID NO 39
<211> LENGTH: 23
<212> TYPE: DNA
<213> ORGANISM: Artificial Sequence
<220> FEATURE:
<223> OTHER INFORMATION: sequencing primer

<400> SEQUENCE: 39
tccataataa tttatgtcaa ggg                                          23

<210> SEQ ID NO 40
<211> LENGTH: 22
<212> TYPE: DNA
<213> ORGANISM: Artificial Sequence
<220> FEATURE:
<223> OTHER INFORMATION: sequencing primer

<400> SEQUENCE: 40
taaggcaaaa tgtgcatgag tg                                           22

<210> SEQ ID NO 41
<211> LENGTH: 34071
<212> TYPE: DNA
<213> ORGANISM: Sus scrofa
<220> FEATURE:
<221> NAME/KEY: gene
<222> LOCATION: (1)..(34071)
<223> OTHER INFORMATION: pig aS1 casein DNA sequence
```

<400> SEQUENCE: 41

```
ttactgaaag agcttcnctt acttcttagt tancctctat gtcatagaaa gaaattntat      60
tttaaactttt accaatgtaa aatttccctc tctgctctca tattgcttta aggcacttca    120
gactttctaa gagtagcaaa cattcttttg agctattaaa agttagttaa tcaatgaaga    180
cattattatt attattattg atattatagt agttacttta aggaaaaagg attacaagat    240
tgctgttgga taatgctgga tataagaaat tgcatatctt tattctgtag acctcagcag    300
aagtattgtg aagtttgtct ttagcaatgc tgagatgttc tttactagtt cttttactc     360
tatttctcgg ggcttaaatc tttcatctta tatgcatgtt aggcattctc caccagctag    420
gatgttattt cctccatcac ctatccgaag attcgacacc ttgaatacat tgcttttgtt    480
gagtaaaaga ataagcagta tgatatatta gaaagagcac aggctctgat gttgggagat    540
ctgagtcatc atttactcat tagctggtgc aagcattttg tatggaaatt aatttactta    600
ttaattttat tacttttatt ttttacttta ttttttgcca tttctagggc cgctcccgca    660
gcatatggaa gttcccaggc tacgggtcta attggagctg tagctgccag cctatgccag    720
atccttagca acgcaggatc caagtcgcgt ctgcaaacta caccacagct cacggcaaca    780
ccagatcctt aacccattga ggaaggtcag ggattgaacc tgcaacctca tggttcctag    840
ttggattcgt taagcactgt gccacaatgg gaactcctta atttacttaa tttataaaag    900
tttagtttcc ttatctacaa aagggaaaat aatgacttgt ttctctacat tacatgattc    960
ttataaggag tagttgtgaa ataattata agaagacttt agaaattata aagaagatta   1020
taaattgaca aagaaatgaa tctatttcat tctgctgatg gatgacttat taatctatct   1080
ggtaaactgt ggttctgatg gccaataatg cctgttaaat acattgtatc ctcataataa   1140
tattgttaaa cagggactgc caatgattgg acccccaggaa agtttatcag tcatgaaaac  1200
cacattttgt caagtcagaa gaactattac tgataagaaa aaatctctt tacccaccaa    1260
attacagtct ttcagaaaga aatcactagg tgagatttag ttaaccaagt taaattttag   1320
cccagttttc ccagatgtct tgagtaggtg aaagcttcct tcatggcaag atgaatgaat   1380
ttttggttgg aggtaagagg caggtagtgg tcttggcacg acatagacag ataaactgtt   1440
acttgtgaga tatcatacct acaaaaagaa tatagggttg gataaggaga tgctttattg   1500
tagacattgc tataaaggta aacactttca tggaaataca attcagcagt tttagcatct   1560
ttgttttgc catatgtgtt acatattttt acaattttca tatgctttta attttttaaa   1620
aggtatttta catacaaact ttcattattg ggtatttta aagagaagac tgtgtattac   1680
atttcaaat ctttcagttt ctagctactc aaagtgtgct gcatgggtca ccagcagtga    1740
catcacttag agcttattaa aaattcatta gctcctggag ttcccatcgt gatgcagcag   1800
aaacaaattt gactaggaac catgaggtgc aggttcaatc cctgcctccc tcagtgggtt   1860
aaaaatccga cattactgtg agctgtggta taggtcgcag acccggctgg gatctggtgt   1920
tgctgtgact ctagcatagt ccagcagaaa cagctctgat tagacctcta gcctggaaac   1980
cttcatatgc cgctggtgcc ctaaaaggac aaaagagaaa aaaaaaaata cgttagttca   2040
ggacacacct cagattttact aaatctgaat ctgaattttta acataatatc ctggtgattc  2100
ataagcacat taaagcattg ttgtagttca ttgttctgtg agaacatcaa atagtatagg   2160
atttcatcaa taaaattcag aagttctttc tattcccctc tcatattcca tcccaagctt   2220
tcttcagttg tggtcactaa taaaaatttt gccttcacac acacacacac acacacacac   2280
acacacacat aaggtctttt tagggctgca cccatggcat atggagtttc ccaggctaag   2340
```

```
ggtcaaatca gagctgtggc cgctggccta tgtcactgcc acaacaacac cagatctgaa   2400
ttgcatctgt aacttacacc acagctcatg gcaataccga tccttaaccc actgagcaag   2460
gccagggatc aatcctgcat cttcatgttt actagtcaga ttcgtttctg ctgagccatg   2520
acaggaaacc ctgcctttac cttttataca tttttaatgc acatacaata tacaagtatg   2580
attcaagact tctcgaaagt taacaaatcc acaagatagg aaaatgattt gggcacaaaa   2640
taattagttg aggttttttt taaaaaaaaa aattctaata atgatcgttt taaatgagca   2700
cttactttgt ctcaggctct cttctaagtg tgtgatctaa ttttttcctc tcgatcacac   2760
aggaagtgga tgttcttaaa cagatgtgga cactgaggca cagtgatttt gcaagattac   2820
cctgctggtc attgagagcc agaaattaaa tttacaattt gacctcaaaa tcttgtcttg   2880
caacaactac atcatgtgtt tcatttaaga tcttctgaga cctattgata cagcactaaa   2940
aaggatattg ttctaaacac aaacataaaa tcaagcataa gttccatatt ccagggata    3000 tcacatacca caccttaccg aaagaactct attttagttc tagatgccaa gattccactt   3060
gtgcaatact aagagtaat gattcgggg ggggggatg cactggggt ttgggatgga       3120 aatgctataa aactgggttg tgatgataat tgtacaacta taaatgtaat aaattcattg   3180
agaaatatag aaaaaaataa aataaaatcc cccctcccaa aaaagaatt cactgtggat    3240 cctctcttag attccaaaca gtatgtgggt ttctagagaa aaacaaagat gtctttcata   3300
ttctcagtaa atttccttct ggaagtttca ctgttaaaag acatttttcct agaagactca  3360 ccagtcataa acccaaatat tcctgggaga atgctgacag actagctttg aaattcatgt   3420
tgtgaattat tgactgtctc atacagaatg agttctccaa tgaggtttaa tgtggaccag   3480
aatatgtagc aacagtacac aaaacttgca gagtaaagtt tacctcctga ctcacagttc   3540
ccttccctcc aaactcgaag tctattgcta atgtttcctc tccttattgt gctagttttt   3600
ctaagaagta tgaatctagg aaagaatgtt tccaatattg aaacttgaaa cacaagaaag   3660 cttcagctt ggttgtccct tatctgacct atttccactt tcactgactt agggattctg    3720
ttggattttc aaaaccgtcg tgatagtact agagtagctt tgcctttgtg tgccaaagat   3780
agttttggtt tatggctgtc gttttgttat gattattaca aagactctcc cattctcata   3840
agtgttccat gttgaatgat cagttatatg ttcatcctac atatgactat tacatcagaa   3900
aatcgctatt caggtaataa tttcattctt tctttactca caggacaaag gcctgttaac   3960
tacaaatcat ctaaatagtg tctcaaatgt gaactgtgat tttcttttt agtgttgaac    4020 tgaacaattt ttttaatt attttttcca ctgtaaagca agggatcaag ttatccttac     4080
atgtatacat tttattcccc acccttttgtc tgttgcaata tgagtatcta gacatagttc  4140
tcaatgctac tcagtaggat ctccttgtaa atctactcta agttgtgtct gatcagccca   4200
agctcccaat ccctcccact ccctccctct cccatcaggc agccacaagt ctattttcca   4260
agtccatgat tttcttttct gtggaagggc tcatttgtgc cttatataag attccaggta   4320
tcagtgatat atcatttggt atttgtcttt ctctttctga cttacttcac tcagtatgag   4380
agtctctagt tccatccatg ttgctgcaaa tggcattatg ccattctttt tatggctgag   4440
tagtattcca ttgtgtgtat atactacatc ttccgaatcc aatcatctgt tgatggacat   4500
ttgggttgtt tccatgtcct ggctattgtg aatagagctg caatgaacat gtgggtgcat   4560
gtgtctcttt caaggtaagt tttgtctgga tatatgccca agagtgggat tgcagggtca   4620
catggtagtt ctatgtgtag atttctaagg tatctccaaa ctgttctcta tagtggctgt   4680
```

```
accagcttac attcacacca acagtgcagg agggttccct tttctccacc ccccccccag    4740
catttgttat ttgtggactt atcaatgatg gccattctga ctggtgtgag gtggtatctc    4800
atggtagttt tgtttgcatt tctctaataa tcagggatgt tgagcatttt ttcatgtgct    4860
tgttggccat ctgtacatct ccttgagaaa tgtctattca ggtctttgcc cattttccat    4920
tgggttgatt ggcttttttg ctgttgagct gtataagtgc ttgtatattc tagagattaa    4980
gcccttgtcc attgcatcat ttgaagctat tttctcccat tctgtaagtt gtcttttgt     5040 tttcttttgg gtttcctttg ctgtgcaaaa gcttgtcagt ttgatgaggt cccattggtt    5100
tatttttgct cttatttctg ttgctttggg agattgacct gagaaaatat tcatgatgtt    5160
gatgtcagag agtattttgc caatgttctc ttccaggagt ttgatggtgt cttgtcttat    5220
atttaagtct ttcagccatt ttgagtttat ttttgtgcat ggtgtgagag tgtgtaccag    5280
tttcgttaat tttcatgcag ctgtccaggt ttcccagcaa tgcttgctga atagactttc    5340
tttttcccat tttatgttct tgcctccttt gtcaaagatt aattgaccat agttgtcaaa    5400
gtttatttct gggttctcta ttctgttcca ttggtctgtc tgttttgata gcagtggcat    5460
gttgttttga tgactgtggc tttgtaatat ttttgaagt ctgggaaagt tatgcctcct     5520
gcttgatttt tgtttctcag gattgctttg gcaattctga gtcttttgtg gttccatata    5580
aaattttgga ttgtttgttc tagttctgtg aaaacgtca tcggtaattt gatagggatt     5640
gcattgaatc tgtatattac tttgggtagt atggccattt ttacattatt gattttccca    5700
atccatgaac acggaatatc tttccatttc tttacatctt ctttgatttc tttgattata    5760
gttttatatg aactgaacaa ctttaagtga taaaagcaaa aggaaaaata ctaatataaa    5820
gcaaattgac ataagctaaa attttgcagg attttgacgtt gtataaatct acaatgaata    5880
tgtttgctcg aattacagtg aacagtcata ttttacaagt ataagaatga tttatttcaa    5940
aatacaaact taattaacta tattctatat ctaataagca aagtgaagat tgatccttat    6000
ccataggtac tagaaaaatc tgtgttttga gtttatgaga attcctatgg tggatacatg    6060
tgttcactaa gagttggctt gtctttaaaa gttctgattg ttcttctttg atggcaagcc    6120
ttattttatc aaatctaaga ctccagtctc agttttttga gtctctaatt ttggactatc    6180
aggaatatta aaattatcag ctttttgtat gtgaattacc cactatagta tgagactaca    6240
gatttgtctt actcaacttt tatttcccct gtgtcttgtc tcatttcttc acctctgtaa    6300
ataaataatg taagaatgag taaacaaatg aggatacagt agctttacac aacttacagt    6360
atgatcctga attggaaata aaataagtca gttatcctgg atgcattctc aggaaaagac    6420
aagagccggg tattgtaagg cagtggagaa tacttgttct cagccccttg gataaatcag    6480
agtaaataga aaatactagt actttttga cattgatgta atgcagtcag caaggacgat     6540
actatccaaa gaggagttta acatggaaaa ctatagcctt gtctatcccc agtatggaaa    6600
gcctgagcca ctgcgaaatt tcttttaacc ccaaataatg ttcctaccat atgactgtaa    6660
attggctgtg aatatcacta tggatttatt attttatttt taaatttttt tggtcttttt    6720
tcttttaggg gctgcaccca tggcatatgg aggttcccag gctagggtc gaattggagt      6780 tgtagctgcc agcctacacc acagccacag caatgccaga tctgagctgt gtctgcaact    6840
tacaccacag ctcatggcaa caccagatca ttgacccctt gagtgaggcc agggatcgaa    6900
cctgcaacct catggttcct agtcagattc atttccctg cgccacaatg agaattccag     6960
aattttttta aatatatagt gtgataccct tctgtaaaca agcagtcaca atcaacaatt    7020 tttttaaatcc agctctatgt atagatattt tattcagcat gcaattttttt tcctaaaatt   7080
```

```
aacaatgcca gttaattcta ggattatatt tcagactgga agaaaagttt ttttttcctt    7140
ttatttactt actttaaaag gtggaaaatt ggagttatgg ttgatttttt ggggggggga    7200
gtatttaaaa attgtattct taaataaaaa ttattcttga ataattattt ttaattaaga    7260
aatctaacaa ttaaattaat gaatactatc acaacacata tacccaaaat aaagcaagca    7320
gaaaattatt tggtgtagtt aaaatactac caaagtttat aaggcaattg tattttcttt    7380
ttggttaaaa aaaagatcag atcacatata aggtaactta ctccacaagg taacttactt    7440
agaatactta gaataaatac ttagaagact tagaataaat aatagggaat aaatagagtt    7500
ttaaaaggtg aaatagatga tgaaatcttc tcatggtcta gtacaattat aaaaattaaa    7560 aattttgat gatttattt tgtctcaaga atttcccta caggtattga cttttcaaa     7620 agctgtaaag gaaattttat tgctatatta atctttccaa ttatccattt aacttaaaaa    7680
gcatgttctt ataataacca taaatatgga attttatgt atcttaattt tgaataatgt     7740
cattccattt cctgtataat ttggtgtcat agcatgaatc actcctttgt tgaaaactct    7800
cctcagaatt tcttgggaga aaattggaca gaaaattaat ttcctctttg agagaattct    7860
tagaatttaa atgacactat tggttgaact gaaaccacaa aattagcatt ttactaatca    7920
ctaggtttaa atatttgtga aacaaagaga tctgccacca tcttgatcat cagctcagct    7980
tgcttcttct ttccggtctt gggttcaagg tatttcattt acatatagca aaatgtgata    8040
tattatgatt tcaatctgtc taattttca ctcctcacta aaaaatatgc actggtaact     8100
tttctgtgtg attccaaata ttgataccct ttaatgatat actggtggct taaaaatgca    8160
tttgcaaatg tcgatgccat ctatctcaga gctttagttg aaaaataata gttttataaa    8220
gaccaaattt ttttgccaaa ttttatgaaa acttattatg tgaaataatt tataatcttt    8280
ttaaagatca tagtgaggat catttctggt agaatatttc aagaccattt ttattccatg    8340
tcattaggtt aataaaatta attctataaa ggatatgcca atgatataca cagatataaa    8400
tgactacttt ttaaaagatg gttagatttg gatatttgga aaaatgcaaa tgaataaaac    8460
cagtaaactc attttggatt tataaatatg tcttccttac aaatgcagtt agattctaca    8520
atatgtagac tgaaacagta tgtataaaat aagctgatta gtttgttggc taatgtataa    8580
acaaattgca tgtatattat gactttcttt tcctaatttc tctggaaacc agtttcccca    8640
ggacataagt tctaagtatc tctgggttct tgtaatttga tggaactcta gaagtcacac    8700
atgataagac atcagaatct tatgattctg ctcaatgaag tcgtctttat gcagtcatgt    8760
catggatata gcaacgtaga aaacataac ataatagcta gactttaaaa aaaaattgat     8820
ggaggttaaa tgtttctaca taatatgcac caacagtgtt tttcccaaag acgctgaaaa    8880
agcaggattc tctaacatag acctagaaaa acaccttcaa aaaattgcag atagggagtt    8940
cccgttgtgg ctcagtggtt aacaaatccg actaggaacc atgaggttgc aggttcaatc    9000
cctggccttg ctcagtgggt taaggatct ggcattgatg tgagctgtgg tgtaggtcga     9060
agacgtggct tggatcccac gttgctgtgg ctctggtgta ggctggtggc tacagctctg    9120
attcaacccc tagcctggga acctccacat gccgtgggag cggccaaaa aaaggcaaaa     9180 agaccaaaaa aaaatttttt ttcagataaa attaaatgcc agttccctgt gccttttagt    9240
ttattatcaa tttttagcaa atctgatggt ctaagaggaa atatttaaaa taattaattg    9300
tagtattctt aaatttagta gtatttaaat attaatgttt atgtattcct ctgacaaaac    9360
cctattacca cttcaaggat caaatgtttt gtttagagg gtgatactgg tgtttcttat     9420
```

```
ctcatataag cactaagcaa gataatttga atgataaatt tttcttgtga gtaaattttc    9480
tgtcagacct aaattttat tttgttttct tatataggtg ttgacaacca tgaaacttct     9540
catctttatc tgtcttgcag ctgttgccct tgccaggcct gtgagtatgg tagagaattt    9600
agaagcttct agattcttga ttgaaattac ctgatatcaa acacaagaaa ctgaggataa    9660
taatcttaaa agtattgaat gatctctaat tacctttga  agccttgata ttaaaactgt    9720
agaaatcctt cacatcttga tcattattac atagttcatt caaagtcatc actccaaata   9780
aaatctgagt tgaaatataa atgcctcaca gtaaaaaaat aaaacaaaa  aatgaaaaga    9840 aaagaaaaag gaataatgta tttaacaaca tagtaaatag aatcaatgag tgttattacg    9900
ctctttgcct gggtccaata aagaattagc atatatttaa acatacaagt ccatgatttt    9960
ttctgtggaa gggctcattt gtgccttata aagattccca ggtatcagtg atatatcatt   10020
tggtatttgt cttctctt   ctgacttact tcactcagta tgagagtctt agttccatcc   10080
atgttgctgc aaatggcatt atgccattct ttttatggct gagtagtatt ccattgtgtg   10140
tatatactac atcttccgaa tccaatcatc tgttgatgga catttgggtt gtttccatgt   10200
cctggctatt gtgaatagag ctgcaatgaa catgtgggtg catgtgtctc tttcaaggta   10260
agttttgtct ggatatatgc ccaagagtgg gattgcaggg tcacatggta gttctatgtg   10320
tagatttcta aggtatctcc aaactgttct ctatagtggc tgtaccagct tacattcaca   10380
ccaacagtgc aggagggttc ccttttctcc accccccccc agcatttgtt atttgtggac   10440
ttatcaatga tggccattct gactggtgtg aggtggtatc ttgtggtagt tttgatttgc   10500
atttctctaa taatcaggga tgttgagcat tttttcatgt gcttgttggc catctgtaca   10560
tcttcctttg agaaagtcta ttcaggtctt ttgcccattt ttccattggg gtgttggctt   10620
ttttgctgtt gagttgtata agttgtttgt atattttaga gattaagccc ttgtcagttg   10680
catcgtttga aactatttc  tcccattctg taagttgtct ttttgttttc tttgggttt    10740 cctttgctgt gcaaaagctt gtcagtttga tgaggtccca ttggtttatt tctgctctta   10800
tttctgttgc tttgggagat tgacctgaga aaatattcat gatgttgatg tcagagagta   10860
ttttgccaat gttctcttcc aggagtttga tggtgtcttg tcttatattt aagtcttttca  10920 gccatttga  gtttattttt gtgcatggtg tgagagtgtg taccagtttc gttaattttc    10980
atgcagctgt ccaggtttcc cagcaatgct tgctgaatag acttttcttt tcccacttta   11040
tgttcttgcc tcctttgtca aagattaatt gaacctttcc atagaaaaga aaatcatgaa   11100
tttggagaat aaacttgtgg ttgccaaagg ggagggagag ggagtggtgt ggttgaggag   11160
cttggggtta atagatataa actattgcct ttggaatgga ttagcaatga gaccctgctg   11220
tgtagcactg ggaactatgt ccagtcactt atgatggagc atgataatgt gcgaaaatag   11280
aatgtgtaca tgtatgtgta actgggtccc catgctgtac agtagaaaaa aaatgtgttg   11340
agaaaataac tattacaaaa atgagaatta tgaaataaat aaataaataa acaaacatac   11400
atgtccaata ttttcttacc aaatataaca gaatgccgcc tattgcagtg tatcctactt   11460
ttggaaccta agtcaaaccc tcacatgaga tgactcatat caaccaatat ttcccaaggt   11520
gtagaaaact gagttattct gctgattcag agatttaatt attatggtcc ttgtagacaa   11580
ggaaactagg taatataaat taaaatcact tttcttctca aaaaaaaaaa agattcagtt   11640
acttatgtag agcaaaaatt attctgttcc cttgtgatat atagctagca aagatggaag   11700
ggataaactg gaattgcttg acaaagaaac catccagata aaataataat cttggatatt   11760
tgggcattgt aattattaaa tataggtgta aaattttttg gaattctgag atattctatg   11820
```

```
atgagactcc tatttcctaa attttgttt ggataatgca ggatcactaa taacctaact  11880
ttcctttttt tttttttttt tttttttgct ttttagggcc atacccacag catatggagg  11940
ttctcaggct aggagtcaaa tcagagctgc cggtggccta accacagcca cagcaacttt  12000
ggaatcaaat ctgagctgtg tctgggatgt accccacagc tcacagcagt ggtggatcct  12060
taacccactg agtgaggcca gggatcaaac ccacctcccc ataaacacta tttagctttg  12120
ttaccccaga ccccctatgg gaactccaaa ccaacctgtt agacactaga gcttttctta  12180
tgctacacct taagcaccaa taggaagaaa atctatgata gcaagttaca agaaaaagga  12240
tccaactttt tcagaaaagt gtcactgtta gtcttttac aaaagaaatg ggtatagttt  12300
ccccagcaaa cagattctat aattctattc caagaaaaca tcattttaa tgctaccatt  12360
taacaaacat aaatcttgtt cccacagttc aaatgtagat tgagttaaat ttttatataa  12420
ttaactgatt ataaaaataa aatccagaaa atgtttaatg aagaaaagta tatattttgt  12480
ttcaaaaatt cataatagtt attttagaa ctaccatgta atataaatag ttcagaaaaa  12540
ttaaatttat cattttggat caagacaaat taatttttt tttcagtctt tttacacatt  12600
tttctcagtt ctccatcata ccccaatgac aggaaatcat ttacttttct gtgattttta  12660
tcaagaaaat aaccatttt tttcttccca gggaaacttg gggtcagatg aatttagcta  12720
ttaaaataca catcattttt aaatagcaaa tgttacattt acagtattct atttgttttg  12780
tgatattatt atcatatttt gattgcattt tgttttcttt ttgtttgttt ttaaattctt  12840
gcattgtttt tcacagaaac ctcctctcag gcatcaggaa caccttcaag gtgagtgcta  12900
ttttctgtgt tctaagaact cactaattgt gggactgagc aatgatatat tggtcataca  12960
tagactctgg tcctactcca cccttctcta taagacattc agtttcacat tcaccgagga  13020
ataagggctt cagttcaagt attaaactgg ttattgatct agtctcacaa accttagaga  13080
gaagggtata gggacttaca taaatattta attaatattt aacatggttt atttaatata  13140
atgttgcttc tttccatctc ttttgcatgt acccaaatat atgattgaca atttgctctc  13200
attttacaca ctgaatctta aattagatac ctccaccaag agcctttaca agagtgatta  13260
atcctccact ctgtccacta attgaattaa taccatttta tttattttc attctttaca  13320
gaatcgagcc agacagcaga gaggtaaagt tctttctttc cctcgacaaa tctctccttc  13380
agttctccat gatgaatgtt aaatatcttc tttgtttcaa ttttatttg tctttggtac  13440
tcagtacttg gagtactttc tcattctttg ctttcattac actccttttc agttcctcct  13500
ttgacacctg acgagtatta agagtatgaa cttactaaac ctctaggctt ggtaagaag  13560
gaaccaaaaa taatgactcc tttagatttt aaaattagat tataaaacta aaactaatta  13620
tctcctaact tacctaagaa atattttggt ttgcctaagt aaatggggaa gttgtgttca  13680
aatggaaaaa tattctcctt ttctgaatca tgtttataat tcacaattga atttctacag  13740
gaactcttca agaaagaaa gtttctcagg tttcctgagg tggtaagcat tatccacttc  13800
ttaaatgaca aatatatttt tccggaaaaa atcaatttaa tttttgtttt ataaatgtgt  13860
ttttcacttg atttgatcaa acttttctt cattttccaa agctcccaca aataatattg  13920
aaatcagata tgcaaatatt aggagttgct ttaaatatta agaactgct ttaaatatta  13980
acttgtgcct ctatatctga ctctttgcaa aacacaaacg cttttttta atatcctatg  14040
tagagtttta aaatgtccat gattatgatg atggaatgtt ctctatctct aaataatacc  14100
tcatatgtgt tgtgttttct ataattttgt gactgaattg tcacatagga aaaaaatag  14160
```

```
aaatttttact tcaagaccac tgtttagaag atttgatatg aacccatctt tgtctaaatg    14220 attttttaaca taacctttct ttttttttgt agcctttatt aagtcagttc agacaggtaa    14280
gaaattctcc accagatata cagtagagtt aacaagggaa gcaatcttgg tttctgtcta    14340
gtaagtgctg tggtgtgggt gttgtgccaa ttctttattg ccttttatg gaaataaaca     14400 ctagacttaa ctgaatcagg cagatgaaat caagagaact cagaactacg tcataaataa    14460
ggtgaaagat aatagcaaca acatttagtg gaacaaaatt ttaaatgatt ttaagtgcac    14520
atttacatac tgatagctta aacaaagaaa gctcagtgag gcgtctcagt gcaagaaatg    14580
atacagcaat aaatattagt gcattcataa aaagcatatt tgtttattta ttgcttttta    14640
gggctgtacc catggcatat ggaagttccc aggctagggg tcgatcagag ctgtagaccc    14700
cgacctacac cacagccaca gcaactcagg atccaagcca catctgcgac ctacaccaca    14760
gctcacggca atgctggatc cccaacccac tgagcaaggc cagggattga accggcaacc    14820
tcatggatac tagtcggatt tggttctgct gtgccataat gggaactcca ggcctgttta    14880 ttttttaat ttgcagcagc acaatgtaaa gtgttttctc atagctatcc attcatttat     14940
gtccctcttt actaatgttt atctcttctt ttttatcctt aaggaaatca tcaatgaact    15000
gaacagggta aggaacatta atgatattta aattattta aaattcattc tttcaaaaat     15060
atattagcta cacttttag ttttaacaaa gagaactcct gagaaaaaaa cagtaataaa     15120
ctcaaggtat caaaatcttt cttatgatag tgtgtcaaaa agtatattct tgcagttcaa    15180
aagtgttttg atttagaaaa acagtatttt tcctgtgata tttataccttt cactgaactt   15240 tcaaaatgac taatgaattc tactcataat tctaaatatt tattttattg atttaatttt    15300
gtatctatga atagacaagg cattaatatg aatgaatgaa tgggtgcaat tttggactaa    15360 ccaattttt gcacttatca ccaaaactga aagaattctt tattaaaggt tttataaaaa     15420
aacaatatta tctgcaccta gaatgtttta cataatcaca gttggttatt ctctttcttt    15480
acacatgagt ttctgggccg gggatcagat ccaagctgca cttgagacct aagtcacagc    15540
tacttcaatg gaggacccct aacccacttt gctgggctgg gtatgaaccc agcgcttcct    15600
agtgccacag atcccattgc accacagggg aacctctaac gcatattttt ttaaaatctg    15660
gtctgtcaga tttttagtag ttttggtatt gagacaacac aggtgccact gaagataaaa    15720
aaatatatct tcctaactat ccttcatact tgaatgatca tcctttcttg gcaggatgct    15780
aggagtgaat caactgaagt aagattcttt attgtaaaac tattaaatat aatgtaagga    15840
aaagaaagaa ataaaatcat ttcctttaaa tatcctaatg aaaatgaatg actaattctt    15900
ttaggtcaaa actaagacag atatctctaa ttcaaagaga gaaaaaaaa aacatacaat     15960 gttatcatct gtgagccata attagctgga taactaaatc aatggtatta tattgagctt    16020
aaattctatg gatcatgtca ctactccctg tactgctatg gtcatgaaaa ctgaacacaa    16080
cattctagat ggagaaaatc cattttgctt aaatatttat acaccattga accaatgctt    16140
catagacttt tatttattac ataatcttta atccaatact tctgcttaat agccaaaagc    16200
caagtaaagg aaaaaaagta agggtagtta aaggaaaatg taggattatt tacactgatt    16260
taccacaaca aataagaatc cataataatt tatgtcaagg gagttcccgt catggcgcag    16320
tggttaacga atctgactag gaaccatgag gttgagggtt cgatccctgc tcttgctcag    16380
tgggttaagg atccggtgtt gccctgagct gtggtgtagg tcgcagacgc ggctcggatc    16440
ctgcattact gtgaccctgg tgtaggctgg cagctacagc tctgattcga cccctagcct    16500
gggaactttc atatgccgtg ggagcggccc aagaaatggc aaaaagacaa aaaaaacaaa    16560
```

```
caaacaaaca aacaaaaatt ttatgttaaa ctcagaaatg cagattaggg aggtaaattc   16620
tttggttagc ctggtaggta ggcttttttc tttccttatc actggctctt accacatatt   16680
tctatttctt ttggcatcta ttttatttga taattattat tttacatttg aatatttgtc   16740
ataaaaaata aattctcttt tcttttctaa gaatcatggc atggaaggcc atgaggtaag   16800
acccttattg taataaactc tacacttaca taacatccat agtatatact ctatgctcta   16860
ttttaagaaa actctcttct caaattgagc aagattgaac ttcccaaaca aggttattat   16920
acccaagaat gtacaatgtt gtgccagata atgttaaaat tagaagagga aatgtgtctt   16980
ttaattgata atcagggaaa atgttattta ttaaaataaa gggtgtaagg caaaatgtgc   17040
atgagtgttt caaatgaaat atgagcctcc aaaaaaaaag aaaaaaaaac ctgtctctac   17100
cacctcaggg tataaactca ctcctgtttg tgagggtagt cttggggaga aagaatctgg   17160
ttgcagtaat tacttaggat caatggccta tgctacttaa tccaaaagca tggaaaaaat   17220
ccactagccc acaatatttg gttaatcaac tttcccaaga gatgaatcat ctgttgacta   17280
ttaaaatcaa tcttttaggt atgtacttga gaacaaaaat tatatccata tttaaatata   17340
aacgtccgtg agttagaaaa aaatctaaat agttcaaagt gtagatgttt taaaagctaa   17400 tgtaattta gttccatacc aaaatttgtt gttgtatttt catgtttcaa tttattccct   17460
tcaaagaagc cccaaggata catgagaata aatatcccac ccggggttct gggtgcccaa   17520
gctcagtagg gcacttcctt ccaaatttca tatatatttt gcattctact caaccacata   17580
tctatgtttg atttaataaa atgttgtttt ttagtgattg gttattacat tcccacatcc   17640
aacatatttt aaataaaatt gacaaccccca aaaaggtacg ttatattggc cctgaatgtt   17700
tcattaccaa ttgctttcat tctaaacaag gagttagcaa cccagtatga aagtgtggaa   17760
caaatttcct tctaattcta aaagtcacag tgttgggaac actgattttc tctcttttag   17820
caaaggggat ctagcagttc atcaagtgag gtaaatcatt ttgatgttaa ttcagtatct   17880
cagttagaaa atgtttatga aaacttgttg tgctatgaat gttacacatc ccataaggtc   17940
tcatggtaca ggctctatgt ctacagctct accctaattt taacatacag gctatgagcc   18000
caaaagatat aataacgcaa atacttgtca gatgaaatta cagaattgtt tctgcgctaa   18060
caattctatc tggctatcca tggtgcccca ttttttttct ctaattttttt tgcctttcct   18120 aggttttggt agtactaaat attttatta aaattactat aagagctatg cttctaaatc   18180
attaatagaa acttggtatt tcctgtgcag acatctactg attctaggtt aactgggtac   18240
tggaatcctt tactccttgt taacctaaaa gagaaaaga gcaggcatag aaggtccttt   18300
cgtaaacttt gggagaagaa aatttcaaaa taaacccaac ccagttatgc ggagtttctg   18360
ggagatcagt aaaagtgcat cgaatatttc acatctacct ccaacattct gaataacttc   18420
cctgttgaaa tcagtgagaa gaggaaaggg aatcttgagt acaacctgta ccttgaatta   18480
ttcatcttat ctcagttacc aaggaatggg tgcctaagat caatttatca cagttaagca   18540
acatggtaac tggctaatta gtattcatac cttgagtata aattaataag tcataaaact   18600
aacactgcat gttttttattt tttaaggaag ttgttggcaa tagtgctgag gtgagatata   18660
cttactaaat ttaaaataca ttcacgttat ccaggatgtg ttaaaattta cttgtacttt   18720
ttttttcttt ttttagcaga agcacgttca aaagaagaa gatgtgccct cccaaagcta   18780
tctggtaaaa ttttactaaa agtttatcaa aggcaaatgt accaaggaat gagtatgaat   18840
gttgtactga tacattattt ctccttctca acctctgcta caccttaata catagtaagc   18900
```

```
cgtctaacag actctagatg tttactgatc ccctgcaaaa ataaagctaa caacttttttt   18960 atcccagggt ttttgtttgt ttgtttgttt gttttgtctt ttgtcttttt agggccgcac   19020
ctgcagcaca tggaggttcc caggctaggg gtctaatcag agctgtagct gctggcctgc   19080
atcacagcca cagcaatgcc acatccaaac cgcatctgca acctacacca cagctcccag   19140
caacgctggg tccctaaccc actgagcaag gccagggatc aaaccggaac ctcatggttc   19200
ctagtcagat tcgtttccac tgcgccatga tgggaactcc tatcccaggt tattaattca   19260
tgctttcatg agatttgtgt tttatagtct attttttggat ctgaataaca tagtattttt   19320 tttattttttt taattttccc actgtacagc aaggggtca ggttatcctt acatgtatac   19380
attgcagtta cagtttttc ccccacccttt tcttctgttg caacatgagt atctagacat   19440
agttctcaat gctattcagc aggatctcct tgtaaatcta ttctaggtgt gtctgataag   19500
cccaagctcc cgatccctcc cactccctcc cctcccatc aggcaaccac aagtctcttc   19560
tccaagtcca tgattttctt ttctgaggag atgttcattt gtgctggata ttagattcca   19620
gttataagtg atatcatatg gtatttgcct ttgtctttct ggctcatttc actcaggatg   19680
agattctcta gttccatcca tgttgctgca aatggcatta tgtcatcctt ttttatggct   19740
gagtagtatt ccattgtgta tatatactac atcttccgaa tccaatcatc tgttgatgga   19800
catttggatt gtttccatat cctggctatt gtgaatacgg ctgcaatgaa catgcgggtg   19860
catgtgtctc ttttaagtag agctttgtcc ggatagatgc ccaagagtgg gattgcgggg   19920
tcatatggaa gttctatgta tagatttcta aggtatgtcc aaactgttct ccatagtggc   19980
tgtaccagtt tacattccca ccagcagtgc aggagggttc ccttttctcc acagcccctc   20040
cagcacttgt tatttgtgga tttattaatg atggccattc tgactggtgt gaggtggtat   20100
ctcatggtag ttttgatttg catttctcta ctaattaggg atgttgagca ttttttcatg   20160
tgtttgttgg ccatctgaat aacatagtat ttaaatggca ccctacagat ttggccagat   20220
ttgagttgaa ctctaagctc taccttttac tagcatgtga tgttagttat ttatctgcta   20280
taagtctgca acctaaactc taaaatgata atataatgat agcaatacac agcacaaagc   20340
aagcactcgg taaacgtggc aagtctcacg aaacttaaca tgttttttgcc cacttcatct   20400 actattctga tttaatttgg ccaaagttaa atcctttgtc agaaagcaaa acaattttc    20460 aattttctta gcaattctga cataagacac actgcaaata aaaatgaata ttcattcata   20520
tttgacagca tggtaattta tttcacatta aaagtaagtt atgaaagtag ttttttctagt  20580 attaaaatat aattggatta gtccaaatta tctgtggttg aagtaacatt aaaagaggat   20640
tactagttct tccttctttg cacctaggaa aggtcatgtt atgattctag ttatattact   20700
tgaaaatgat aggatgagac tggattgtct ccaagcaatg gacaaatattt ttttttttctt 20760 gaatagggac atcttcaagg actgaacaaa tacaaactgc gccagctggt aatatcttta   20820
ttataataac acaaaactaa actgtgcaaa atcaaaataa ttaagttgta aatttgggtcc  20880 acctctgaat atttttttaa gaaattattt attctagact tgaccattaa taataactga   20940
caaataatcc aaatgattgc ctatgtattt actgtcacag ctatttgttt ctatttatgc   21000
cgagagtagt attgtaaatc aggaggtgtt cctgtcgtgg cacagtggaa acgaatctga   21060
ctaggaacca tgaggttgca ggttcaatcc ctggcctcgc tcagagggtt aaggatctgg   21120
cattgctatg agcagtggtg taggccggca gctatagctc tgattagacc actagcctgg   21180
gaacctccac aggccacagg tgcaggcctg aaaggacaaa agacaaaata atcatatcca   21240
taattgctaa gcagggagaa atttcctttt tttactaaat tctttatcaa accctcttag   21300
```

```
accctcccac atgatgaatt atattcagaa gtttattctt tttattgttg ttgcaaattc    21360
agtcttgaaa ggtgttccat aaatatgcct gcttcttaaa gcacagatat gccaaataaa    21420
ccttccattt aaggaaagag tgtagactca ggagaaggaa ccaggagtcc taaatattca    21480
acttgctttt gtcaaaattc tctaagaaag aggagctttt ttgctgcacc ttgggttaag    21540
gggccatcat tgtcacagct gtggctctgg ttgctgctgt ggcacaggtt tgatccctga    21600
actgggaatt ttcacatgcc atatgtgtgg ccaaaaaaaa aaaaaaaaaa ccaaataaac    21660
ataaacaaaa agctctaaga ggaaagaatt ggcagattga ttgatctaat ggtctatgaa    21720
tccatttcct taggtgtgaa atggaaatac agttattctc actccctggt gttattttga    21780
atattaaatg agcaatcgcc tactcaggtc tccctaagtc cagcttgtag caagtccagt    21840
aaaagcttca ttcctccttc tcctgccccc actccacagc ctctagaaaa tttgctgcgc    21900
tcatgagact tctgataaca ttatgaaagt cttttcatcag gatatgtgtt tgaactataa    21960
tgtcataaac tctttatcag cagaggtatg gatagataaa aaacatatca attagcaagc    22020
ccttcttcca ctatttaatt ttgatccttt tgagtatcac aatctttcat ttggaaggtc    22080
aaaaaaaatt tcttagctat agcaaataaa caacctaatt aggactttag ggaaaaaagc    22140
ttgtcagttt aggtaaaatta ccttttcaca ttttcttctg ttatatatgt aagatgaaga    22200
gagttaataa tgaatttaat ttgcacctca gttttttactc ttatttcaat acctgagtta    22260
cctgtgttta taaagtccaa ataaatttaa atttatcagt acttcactgg aattcatcat    22320
tactgatcta agaaattacc tgaataatca gttttaggac ttagctctga tatgacaagg    22380
tcataacccc cagaagtgtt aggaccagta aggcattgct cattatgttc attgtatttc    22440
atagatggtc atcagttttt agcatagtcc tcaagtgcat gaaagtactt agtaaatctc    22500
tgttattcac atatgaataa aatcaatata ctaaaagaag atgttctttc tttcttagga    22560
agctattcat gaccaggtaa agttatttat ttattaagtg taaaatattt tagtatttcc    22620
ttcatgtgtt atatttttat aatgtgcatt ccttttttt ttataacaga aatatatccc    22680
aatagagaaa tttatctcct acccatatct ggtaatatgt tatttaaaat tcaccaaaga    22740
taatatttaa ataattgatt aatagtctta tatggaaaat atgtattctt agagaaatga    22800
taggtttttc tttttcccag ggtatgagtt ttataaattc tttatttttcc aaactatact    22860 aagtctagcc tttagttgaa tatttttttc taaagttaga aaataaaaag tgtattgcta    22920
ttttttttca taattttgac ctagaatact gtctatccta aatttcatgg atgatgatat    22980
actcttggta cattgtaaaa tgaatgtgtt gtatcagaag atatctaagt aatttaaaat    23040
gtctttcctt taaataggaa cttcacagaa caaatgagga caagcatacc caacaggtaa    23100
tattttgttt aataaattac acagttatat tgtaaagttt aaatatgttt gttttaaat     23160 accctcatac ttttgagggg gtttctttct taggcagctc ttttttatttt tttgcatttt   23220 ggggccacac ccaaggcata tggaagttcc catactaggg gccgaattga aactgtagct    23280
gctgacctac aatgacaacg ccggatcctt aacccactga gtgaggccac ggatggaacc    23340
tacatcctca tggttgctag ttgggttcgt tactgctgag ccacaagggg gactctgcag    23400
gcagttattt cttattccca gctttctgaa ataatttata ttgatcaatc agagatgaga    23460
accatgtgtc actcttcttt ggaataagat ttgttctatc cggtctgtct cacctgacgt    23520
ggtcagccta tttataattc tgagcactat caagaattca tctccatggt tacattaatt    23580 tccccttttaa gatattcttt aattttgcat ttttgtccat aatttgattc ttaaattcaa   23640
```

```
tttacattta ggaaactcaa actcaccatt atgctctttt aagcaaagag agtggagatt    23700
tactaactga cactttctca agcaaccatc tggagccata gtaaatgtct gtccaaaaaa    23760
aatcttcctg atcctctgtt ttctcctctg tgaagtgaga ttatatataa tacctaacag    23820
aaactgactc ttctcctgcc ctcccttcca ctgatgccct agtgctcctg tggcttctgc    23880
tttccttttt aaggcaatga tgagttacca tgaaacatat gttactctac cagctctgat    23940
tcctgtgaat agctacacca attccaatca tggaggctcc caatcactat ttgctgttta    24000
gggaatctta taaggatggt agagtatgtt tcatatgtct aagaagaaac ttccttttaga   24060 gaaggcaatt gggaaaattt tagtatgagt tctcagatct ctaacataaa aagcatttca    24120
agtaggttgc ttcttacagc tttggtttta tttagcctta aaaaagtaac tttaattctc    24180
tttttctttc cagggagagc ctatgaaagg agtgaatcag gtaagagtga gtgtgtgagt    24240
gtgtgtgtgt gtgtgtgtat taatactgcc ccataagcta gtgctatgct agtatttctt    24300
ggctattgac tggtgttgga ctctctagag ctggttctaa cattgctgtg gaagatctga    24360
tagatctgat tgccaaagga aatgaatgaa tgattctatg ccatctgtg agtgatgata     24420 gcttcaggtc aactttaagt caggacaatc tcaaccagct atttacattg ttaaaatttg    24480
acctgttatt aatctatagt atcatgtcat gaaaataatt tgagttttca atcttagatc    24540
tgacaccttc taattacagg accttgagca aattgtgcta ttctcttga gcactgcttt      24600 ttcatttgtg aaattaatat atggacctat ccatttattt cctccccaaa cttccatatc    24660 ctgattttg gagtgtcttt ctatatcttc acttttagaa gtagtagctc tgcattcaat     24720
tcagtttctt cagtctctct ctctctctct ctctctctct atatatatat atatatatat    24780
atatatatat atatatatat atatatatac acacacacag acacacacac acggcatgct    24840
aattaaaaag aatgcaaagt aaaccacgga gttttctcaa tatgaatgtt attaggaaga    24900
aaaaaatttc ctcaagattc aaaacatagt agtcatcaat cagttttatg tgcatcttta    24960
ctgtgcatca gatttactct caatttcttc tgaaattctc taatcacttc tgagctaaag    25020
taagagaaaa ggcaattact cacttcattt gagatttaaa gggtacacta acctcaactt    25080
ttcatgtaat tccaaaaaaa aaagagggtg atgattataa tctcaataag aatatttgat    25140
agcaataatt taatcatggt atttaattgg atttaaatta caaaactatt ttcccctct    25200 ctgttaagga acaggcctac ttctattttg aggtaaattt attttatttt attctttat    25260 ccaaatgatt tataaaggaa aagtattggt aaacatttat aatatagtaa tctttatgta    25320
ggtaaccaca gcaaaactgg aaatgttttt atttttttatt ccatcaaaaa gcacatattt    25380
tcacctaaat atatagagaa ttatgttatg cataaaaaca agtaaaacat catgatagat    25440
gaacagagtc acctatcctg aaatttcaga aaggaaaatg gtttggcacc aaaactttat    25500
aattaggaaa ggataatgtg ttaggaattg gagaattctt ttccctttat tcctggcatt    25560
tctgagagca gaggtatgga ccccgagtgg gaggcccttc cttttgtttg agctcagtgt    25620
cttcatggaa aattaagcta agaacaaaa tggccaaaaa agtcctttcc agtccacaag     25680
tccatgaggt tataaatttt ataataatta aattcacacc cctacattcc tctgggctct    25740
ggtaactgga ctccgattag taatgcagat tcgtggggtt caatgctgaa tattgacctt    25800
gaagaagtta tttcttcatt actcacaagt ctcccaaaaa gcccttccca aaagttcctt    25860
tgccatgatc cactgcatgg aagaatgtga tttctccatt ttccttgcag agtagatatc    25920
tcttgtgatg ctaatagcca tgtcagaagt gaatagaatg cttctttttt tcagagattc    25980
taaagagcaa tttcccatat cctgttgcta tttcattctc tctagcctct ccaccagttc    26040
```

```
taccagcttg atgcctatcc ctatgctacc tggtattatc ctccacaata tattgctcac   26100
ccattattca ccaacatccc tcaacccact gcccctgaga agggtggaaa aactgagatt   26160
atgcctcagt ggtggtaagt tcattttaat gactgtatat tgatgttcta ccaaaggaaa   26220
taaaagaaaa cttcttaaag aacataccat aaaaacagat ttagaataaa catgacaaaa   26280
tcaatatcta gagcgtcgta gtagaatttt ccaaaatggg aaattggcag gacgttctga   26340
tatctgcagc taatgttaat ccactactca ggaacttgtg gagcagcgct ctctgttctt   26400
tgagattcat tctgatgaag tcaggaaaaa gttttctatc caaagcaaaa acacagtaat   26460
ttcactttat cctccttaca attttactaa tctctaaagg cttttctttt ggttatatat   26520
acccatgata tacattacaa ttcagtgtgg ggaataaagc acagattttg gcatccaaaa   26580
gtcccaaatc caaatcctga cctttttttgc ttacttaaaa taatgcatta atgcttattt   26640
ttataattct gaaggtgatt aaagacaata atctgttaag catagtgctg ggaagataca   26700
tagcagtcag ttttttattga tttagtaaaa ttgtactgct gactaccttc atcacatgat   26760
tttaagaatt tttgttttttt cagaagaatt aagtgaattc tcaggaactc cacaattatg   26820
gcctttggta agttggaaat catttgtgga accattgatc ctcttttcgt ttaaagactc   26880
attacaaaga taggactgta gactataaag attttttttc ctgtagttga gctccttgtg   26940
gacacattag cacttagata ataattaaat tggcttggac atttgcaaat gtttgtttca   27000
taattatact atatgtaaat agcaatcaaa ttagataatt ttaatgaata taatttatta   27060
tattgaaccc ctatacaagt ataggagcat gaatgctact aattttccat caagatgtga   27120
ccttgagatg ctggtaaact caacagtggg attctatttt ttatgatcac tacaataaaa   27180
atccttagca agtcatgtga taaaaccaag tatttgtttc tcaacaagaa acagacttt    27240 aacgtctaca gacttgtttt aattaacttc atccattgta ctggtgtttc cgattgtatg   27300
tcagtagagg tgtgtgtgtg tgtgtgtgtg tgtgttttcc ctttctagtg gtggaaattt   27360
cccttccaac tgattgaatt aaggaaaatg acaaaacata tgggaaaggt ttttctttga   27420
attccttggc catatttctt ctgttactgc aaaagaaaat actacctagc aataaattgt   27480
ctatataact taaaattatc aggataaatg ggtacatatg tcagtcacag gaaagaacaa   27540
ataactttgt gagtttcatc ttaaaatgaa gagaaaatga ttattcaaat gcatcataac   27600
agtgtctctt ccattcaaaa catgtaatat aaccaaccac atatctcttt ttctatttac   27660
agatgtgact gaaaatacca tgcttgaaat ttctcctctc catctaccat gtagaaccat   27720
tttatctgaa gactttgact gttctttttag aacagggaaa tcgcaaatcg aagtcaatct   27780
tccttcttga attctttact ctatattaga tagcatataa tccttttcct ttggcaaagt   27840
tgtcctaaca gtttagtgtc taaatttcag ttgtatcatg ccagtaggaa gaccactgaa   27900
tcagagggaa ttaaaagtct ttactaaatt tcaatatgga aattttgttt aaaaagcctt   27960
tgaattgctt ctcctgtaag tgccatcatt tcaaataatt gtgtgcagtg actgagattt   28020
ttcttccttc ttttcaataa attacatttt aaggcacaac tcctattttt tgtcattatt   28080
ccattcagca gaatttgcac aatcctgtta acagtcttta tgcctgtaac atttttatttt   28140 cactaaattt ttattacact ttcaaccaca attcaatgaa caaaatggta aatcttcatg   28200
cctagctgat gctgacaggt tataagctgg gtctaggatc tttcatttga agtcacctgt   28260
ctataggata ttctccatga gaacataggt gtggctgcag agaagaacag tggtatgaca   28320
gttgcgggtg cactgggaat ttgaaaaaca tggctaagct gtttatttat gtcaccagaa   28380
```

```
cctgtttgag ccaaactcat ttgattattt gattattata cacttacttt tataattagg    28440
tagattagat aataaacatt taataggtta gaccatggca tacagtaaca caatactcag    28500
tgtcctcccg aactccaatg aagagttatt tctcaaaatg acaatagtcg cttgcattaa    28560
taccctcaaa accctgctgg aatttacttt ccagagttta ttccagggtc cccaacaaac    28620
cctatctgct gtgactcttt aagaaacttc tttccaccag gtcataaaat acaggtggca    28680
aggtctcttg taccacaacc taaacgacct atttagttag cagttctgtc tcttatcgat    28740
tatatatata attgatatgc acatatatgc ataacaccta aacatgtatt ttttgcctat    28800 aacgctttt taccagttgt cacttggttt ggtgacacta gtctccttcc attttccctg    28860
aggttggaaa tgcaatttca attactttgc acctctcacc agagttctca gtcaattgtt    28920
tagcacaaaa gaatttcata aaagtttacc cttcaaggaa aagtttaaag gagaataatt    28980
tatcctttgt agacacaggg aagtgcaggg ccattagaac taagcatatc tatttatgga    29040
tgtttaaata tttctctttc aattatgatt gtcaaactgc cttctagagt cttacaaata    29100
acagaagcag aaaaaaatac agttgtgaaa aaacagtgct gacagtgaac tgaagaatat    29160
gtgcattcct cattggctgc cccttccaat gcattgttgc tgtgcaggaa tacacaggtc    29220
aaatgtaacc aaatttgggg acttctaggt gaactagaaa tgtggattgt gtgtaagatc    29280
tcctattttt aaatattggt ctagtgtttt ttaaatataa aatacacagt ctccttctct    29340
ttattggcca gacccaaccc ctctaacact agtctatgta ctatagtgta ctttaagtca    29400
ttaagtaaag gactttctac ttccagtcca atcaaggttg aatcccagtt acagtgaagt    29460
gaaagtgaga agtaggacat tagggtaata attagctaca gtaaacaaag aaatcatgat    29520
tccatcatga caaatacaca gtaagtgtta ggggttacat ggggctcatt gttaaaatgg    29580
ctcatcatgc tgacccatga gactgaccat cttgttcaag cgacatcctg tttttgccac    29640
tggtgcctat tttcccaaga ctacaagacc agggggggacc acacacctcc agctttctca    29700
agattatgag tgcaccctac cgtgagatac ctctgacttt ctcatgacga tgtgaccacc    29760
agagtccacc tgcaggtgaa agataaacta taaactaacc ttccccgct tcaggaatca    29820 atttcccctc tgcagagtat aagaaggccc tgctagaagg gcgggggggc tgactcttct    29880
caaaggtcag tcagcctctc cttttttcctt ctaataaatt ttcttctctt tgcctgaaca    29940
cccaattcct tctcttttc tccatgctcc ccttacagta agaccttcag gagcacttgg    30000
gagcaggcgg ttctgtaaat tttccatacc ttcccatata ttccactttc aatagttggg    30060
ttcctattgt cctaactttc acaagaacta tccattttat ggattcatgt catattaatc    30120
actatagatt agattttgca tgccctcccg aattcatatg ttgaagccct aactccccca    30180
tgtgatgcac ttggaggtgg catctttgga ggcaaatagg tcatgtgagt gggatatcta    30240
tgagtgggat tagtgcccct ctaagaaaag ctaggagaga gcttgtctat ctttctgcct    30300
tgtgaggata cagcagaaag gcaggcacct gcaggccaag agggagcctt caccggacac    30360
aggatctgct ggcacctgga tcttggtaaa tgttatttgt aactgtatgt ctgtgagttg    30420
ctatgggcag gatgtactgg ctggtaaaca ttgtttagta ataagtggat gtggtttaca    30480
ccagatttag gagaatctag gagtggtgaa gtaaatggg gtttggcatt caattgttga    30540
ctcattatat agctaaaata tgcctgcttg atgagcttat tgtaagagat ctcacaagtc    30600
attttgagct tcctagtatt gaggtgcttt gcacaccctc tgttagtggc ctaagaactg    30660
aagataacac atgtcttgtg ctaccaagca gtaggaggat aaatgaagtt tgctcttgag    30720
atctcagtac ctctttcatc tttcaatgca taccccttctc ctgttgttgt actctgtcct    30780
```

```
ctgcctgtaa taaagctgtt ctgttagtgt aaactgtatg ggtctccttt aactatcaaa    30840
aatgttaggt cttgtgtgat taccacctcg ctgtaatata cagcaaaaaa aaaaaaaaaa    30900
aaaaaaagga gaattcatct gcaagttctc tctcatctcc tgcttctcat tctgaaattt    30960
tcacctcagt gggggctaaa actatgcata taacagtagc attaaccaac tattacagtt    31020
tctgaggaaa cccggtcctg tgctatagta cacaatccca ttcaagtcca acagcaaaga    31080
ggtgagtctg cattgatgag gtcccaacca cagggaaaag gaagaagaca ggcaatatac    31140
tgaatgcaca catcacaatg aatcaccaca gatacttact tccaggctaa gggaaagaat    31200
atcgctagtt ccccagcact ttctcacatt ttctgtcaag ttgtaccttc cctcagataa    31260
ccaatagtct agcttatcac acaagaattt aatcgatcat tagattctaa taaattccac    31320
ttattggatt acatattcca ttatattttg gcctgattac tgtcattcaa tgttatttat    31380
ataaaattca cccttgtttt tttgtggcag taactcattc atttcaactg cagtatgata    31440
tcccattcca ctttagacca tgacttattt atacaaaata catttataca aaatacaaat    31500
ttatacaaaa taacgtaaat gttaattcac atttatgttg atttttagttt agggtattag   31560 cattgttagg agtattgggt aaatgttttt agaatacata tgaaagcata ttatggtttc    31620
cttttggttg tatacctaag agaagaaatg ttagttataa tataagcaga tgtttatttt    31680
tgacaaagac tcataatact ttccgagttg cttgaaccat tttatattta ttttaacatt    31740
acctagcatt tattcagttt gcttattttt gtaaatactt ggttttacca attcttctca    31800
ttcagctatt ctggaggttg tgtcatgata tctggtattt ttaacttgca ttttccagag    31860
aaataatggt attgaacatc ttttcatata tttattgaca attaaaataa cctctttggt    31920
gaagtgccca ttcaaagata ttgcttgtgc actattatat tagttgcctt tgttattgaa    31980
atatgcccaa ttaaattttg gacaatttgg ggactggatt cagacaaaaa gttctgctgg    32040
ccatgtcagg tttgagatat taattagata ctccgatgtg gagaagaatg cagttgagca    32100
cttgaatttg gagttcagga aaaataagt ttgaggacat acatgtggaa gcttcaagcc    32160
catgaatgga cttaaagtca tggaatcaaa caacatcaat catagtaagg ctaatcccta    32220
gggtattcca cacattgcat gtttggaaaa ggagaaaatg ccagaagaga cgatgcaaag    32280
aaataactgg tgagttaaga gggaaatcaa gggcttatca ggcttaggat ttcaaataaa    32340
atttgcgata tttcaaaaaa aaaaaaaaaa aaaggaatga tcaactgga ccaaatagca    32400 ctgatagttt gggtaaaata aacatagatt ggtaaaatga atgttgttgg taatcttgaa    32460
aaaagtggtt accataggg taaagctcaa tgggaacagg ttgatgagag aataccatgt    32520
gaaacaatag acacagtagt ttggacactt cctttctgat ggttaccata gagcagtcta    32580
aagtactgcc aaggatggaa ttttttcttt aaagatggga gatattatag cctaagtatg    32640
gcttgcactt gatcctgagg taaggaaaac actgaggatg caggaaagat gaaattactg    32700
ctagaaacaa gtccttgtgt aaacacaagg ggagggaatc aagttacaa atgtaggagt    32760 tgtgtaacca agcaggaccc tgtgaagcct tcccacagtg gatccacact cttgtcctct    32820
gcctgcattt ttgtctatag aaaaacttta gtcaaagaat cagtttgatc agagaagtga    32880
gaaaatacag agaaaaagga atacagtcaa gcaagacaga gtaataatag tttagccact    32940
cagcaatgtc aaggacttat ggttcttcct catggactat agataatatg ctgagccatg    33000
tccttggaac ggttttgcag gtgctcaaac ccctaccagg cggaagaagt caactgcatg    33060
ctgcccacaa acatgtagac cccagaccag ttggaaacag aaggttgatg atgctgactc    33120
```

-continued

```
ccaattaccct catcaccaaa cagttaggaa aatatccaag ggctgatcat gcccggctcc    33180
ttgaagagta agagtaagag tcctcaccac tcctccaaga ggcacacagt cctcgaagca    33240
ctagcctgct gtgtaccctc tgcctggcaa ttaaagctac ttttgccggt ttccacattt    33300
ctatttggcg tcagtgtata gaggcagccg atacttcggt gatagttggt agacagataa    33360
ttcattgcaa tgaaaaaatt actccacaga cagagacaag ggatatcaga gcttcacata    33420
agtctactct cttgggcatt agtggctaaa acaacatcct tcagctcatt ctcattgtga    33480
cactggcact ggctgctcta gtgtaagtga ggaatgtgga gccacacgga cacccatcct    33540
gcactgtgtg gggtgctatt cacattaaaa cttcaataaa acccctttcaa ctgactgtgt    33600 tatagatgca aaaactgaat ctttgaaagc ctaacttata cagcaccatt tagccaccat    33660
gttacagagc cgtgattcag attttacatt ggaagccttc ttatctagga ggatcataaa    33720
atttaacatc caatgcagat acttttgaga gtgaaaggca caagtataat agttcagctg    33780
agataagagg tataaaccaa gactttctag agtatattca gcattagatc accctgcctt    33840
ttcctccatt tttgatataa tttagtactc aagtcaaagc attctactca atttcaattt    33900
ttccgtggct attttaaca ttaataataa ctttaagtta actaataaag aggccagtta    33960
ggtttggaaa attataataa aaacaggaaa acttaaatat gcctaaggat taatttattg    34020
aaatgactgg ttaggaaatt ataattccat aaattatttt tatacatatt t             34071
```

```
<210> SEQ ID NO 42
<211> LENGTH: 23
<212> TYPE: DNA
<213> ORGANISM: Artificial Sequence
<220> FEATURE:
<223> OTHER INFORMATION: pig aS1 4.6kb forward primer

<400> SEQUENCE: 42
aggattacaa gattgctgtt gga                                              23

<210> SEQ ID NO 43
<211> LENGTH: 23
<212> TYPE: DNA
<213> ORGANISM: Artificial Sequence
<220> FEATURE:
<223> OTHER INFORMATION: pig aS1 4.6kb reverse primer

<400> SEQUENCE: 43
aaaatcgtca actaccctga tta                                              23

<210> SEQ ID NO 44
<211> LENGTH: 22
<212> TYPE: DNA
<213> ORGANISM: Artificial Sequence
<220> FEATURE:
<223> OTHER INFORMATION: pig aS1 5.7kb forward primer

<400> SEQUENCE: 44
agctgcaatg aacatgtggg tg                                               22

<210> SEQ ID NO 45
<211> LENGTH: 22
<212> TYPE: DNA
<213> ORGANISM: Artificial Sequence
<220> FEATURE:
<223> OTHER INFORMATION: pig aS1 5.7kb reverse primer

<400> SEQUENCE: 45
cacccacatg ttcattgcag ct                                               22
```

<210> SEQ ID NO 46
<211> LENGTH: 21
<212> TYPE: DNA
<213> ORGANISM: Artificial Sequence
<220> FEATURE:
<223> OTHER INFORMATION: pig aS1 4.9kb forward primer

<400> SEQUENCE: 46
cactcagtat gagagtctta g                                              21

<210> SEQ ID NO 47
<211> LENGTH: 23
<212> TYPE: DNA
<213> ORGANISM: Artificial Sequence
<220> FEATURE:
<223> OTHER INFORMATION: pig aS1 4.9kb reverse primer

<400> SEQUENCE: 47
ctgttcagtt cattgatgat ttc                                            23

<210> SEQ ID NO 48
<211> LENGTH: 21
<212> TYPE: DNA
<213> ORGANISM: Artificial Sequence
<220> FEATURE:
<223> OTHER INFORMATION: pig aS1 5.4kb forward primer

<400> SEQUENCE: 48
tttggttctg ctgtgccata a                                              21

<210> SEQ ID NO 49
<211> LENGTH: 21
<212> TYPE: DNA
<213> ORGANISM: Artificial Sequence
<220> FEATURE:
<223> OTHER INFORMATION: pig aS1 5.4kb reverse primer

<400> SEQUENCE: 49
gtagagctta gagttcaact c                                              21

<210> SEQ ID NO 50
<211> LENGTH: 21
<212> TYPE: DNA
<213> ORGANISM: Artificial Sequence
<220> FEATURE:
<223> OTHER INFORMATION: pig aS1 5.3kb forward primer

<400> SEQUENCE: 50
cactcaggat gagattctct a                                              21

<210> SEQ ID NO 51
<211> LENGTH: 23
<212> TYPE: DNA
<213> ORGANISM: Artificial Sequence
<220> FEATURE:
<223> OTHER INFORMATION: pig aS1 5.3kb reverse primer

<400> SEQUENCE: 51
aactgattga tgactactat gtt                                            23

<210> SEQ ID NO 52
<211> LENGTH: 22
<212> TYPE: DNA
<213> ORGANISM: Artificial Sequence
<220> FEATURE:

<223> OTHER INFORMATION: pig aS1 4.7kb forward primer

<400> SEQUENCE: 52
agatctgaca ccttctaatt ac                                                22

<210> SEQ ID NO 53
<211> LENGTH: 20
<212> TYPE: DNA
<213> ORGANISM: Artificial Sequence
<220> FEATURE:
<223> OTHER INFORMATION: pig aS1 4.7kb reverse primer

<400> SEQUENCE: 53
gtgtattcct gcacagcaac                                                   20

<210> SEQ ID NO 54
<211> LENGTH: 21
<212> TYPE: DNA
<213> ORGANISM: Artificial Sequence
<220> FEATURE:
<223> OTHER INFORMATION: pig aS1 4.4kb forward primer

<400> SEQUENCE: 54
gtcaaactgc cttctagagt c                                                 21

<210> SEQ ID NO 55
<211> LENGTH: 21
<212> TYPE: DNA
<213> ORGANISM: Artificial Sequence
<220> FEATURE:
<223> OTHER INFORMATION: pig aS1 4.4kb reverse primer

<400> SEQUENCE: 55
gtagacttat gtgaagctct g                                                 21

<210> SEQ ID NO 56
<211> LENGTH: 27
<212> TYPE: DNA
<213> ORGANISM: Artificial Sequence
<220> FEATURE:
<223> OTHER INFORMATION: pig aS1 promoter 5.5kb forward primer

<400> SEQUENCE: 56
ggatccggct gtcgttttgt tatgatt                                           27

<210> SEQ ID NO 57
<211> LENGTH: 27
<212> TYPE: DNA
<213> ORGANISM: Artificial Sequence
<220> FEATURE:
<223> OTHER INFORMATION: pig aS1 promoter 5.5kb reverse primer

<400> SEQUENCE: 57
ctcgagaact aaaaggcaca gggaact                                           27

<210> SEQ ID NO 58
<211> LENGTH: 27
<212> TYPE: DNA
<213> ORGANISM: Artificial Sequence
<220> FEATURE:
<223> OTHER INFORMATION: pig aS1 3' arm 4.3kb forward primer

<400> SEQUENCE: 58
ctcgagttac aattcagtgt ggggaat                                           27

```
<210> SEQ ID NO 59
<211> LENGTH: 29
<212> TYPE: DNA
<213> ORGANISM: Artificial Sequence
<220> FEATURE:
<223> OTHER INFORMATION: pig aS1 3' arm 4.3kb reverse primer

<400> SEQUENCE: 59
gcggccgcca gctttattac aggcagagg                                    29

<210> SEQ ID NO 60
<211> LENGTH: 39
<212> TYPE: DNA
<213> ORGANISM: Artificial Sequence
<220> FEATURE:
<223> OTHER INFORMATION: forward primer for first point mutation

<400> SEQUENCE: 60
tatatactac atcttccggg tccaatcatc tgttgatgg                          39

<210> SEQ ID NO 61
<211> LENGTH: 39
<212> TYPE: DNA
<213> ORGANISM: Artificial Sequence
<220> FEATURE:
<223> OTHER INFORMATION: reverse primer for first point mutation

<400> SEQUENCE: 61
ccatcaacag atgattggac ccggaagatg tagtatata                          39

<210> SEQ ID NO 62
<211> LENGTH: 29
<212> TYPE: DNA
<213> ORGANISM: Artificial Sequence
<220> FEATURE:
<223> OTHER INFORMATION: forward primer for second point mutation

<400> SEQUENCE: 62
aagacgtggc ttgggtccca cgttgctgt                                    29

<210> SEQ ID NO 63
<211> LENGTH: 29
<212> TYPE: DNA
<213> ORGANISM: Artificial Sequence
<220> FEATURE:
<223> OTHER INFORMATION: reverse primer for second point mutation

<400> SEQUENCE: 63
acagcaacgt gggacccaag ccacgtctt                                    29

<210> SEQ ID NO 64
<211> LENGTH: 24
<212> TYPE: DNA
<213> ORGANISM: Artificial Sequence
<220> FEATURE:
<223> OTHER INFORMATION: forward primer for hEPO

<400> SEQUENCE: 64
ggatcctgtg gtcacccggc gcgc                                         24

<210> SEQ ID NO 65
<211> LENGTH: 26
<212> TYPE: DNA
<213> ORGANISM: Artificial Sequence
<220> FEATURE:
<223> OTHER INFORMATION: reverse primer for hEPO
```

```
<400> SEQUENCE: 65
gatatcccat gggacaggct ggcgct                                         26

<210> SEQ ID NO 66
<211> LENGTH: 28
<212> TYPE: DNA
<213> ORGANISM: Artificial Sequence
<220> FEATURE:
<223> OTHER INFORMATION: forward primer for WPRE

<400> SEQUENCE: 66
gatatctctg ttcctgttaa tcaacctc                                       28

<210> SEQ ID NO 67
<211> LENGTH: 26
<212> TYPE: DNA
<213> ORGANISM: Artificial Sequence
<220> FEATURE:
<223> OTHER INFORMATION: reverse primer for WPRE

<400> SEQUENCE: 67
gcggccgcga gcccgaggcg aaacag                                         26

<210> SEQ ID NO 68
<211> LENGTH: 2331
<212> TYPE: DNA
<213> ORGANISM: Homo sapiens
<220> FEATURE:
<221> NAME/KEY: gene
<222> LOCATION: (1)..(2331)
<223> OTHER INFORMATION: DNA of hEPO

<400> SEQUENCE: 68
tgtggtcacc cggcgcgccc caggtcgctg agggaccccg gccaggcgcg gagatggggg     60
tgcacggtga gtactcgcgg gctgggcgct cccgcccgcc cgggtccctg tttgagcggg    120
gatttagcgc cccggctatt ggccaggagg tggctgggtt caaggaccgg cgacttgtca    180
aggaccccgg aaggggagg ggggtggggc agcctccacg tgccagcggg gacttggggg    240
agtccttggg gatggcaaaa acctgacctg tgaaggggac acagtttggg ggttgagggg    300
aagaaggttt ggggggttct gctgtgccag tggagaggaa gctgataagc tgataacctg    360
ggcgctggag ccaccactta tctgccagag gggaagcctc tgtcacacca ggattgaagt    420
ttggccggag aagtggatgc tggtagcctg ggggtggggt gtgcacacgg cagcaggatt    480
gaatgaaggc cagggaggca gcacctgagt gcttgcatgg ttggggacag aaggacgag    540 ctggggcaga gacgtgggga tgaaggaagc tgtccttcca gccacccct tctcccctccc    600 cgcctgactc tcagcctggc tatctgttct agaatgtcct gctggctgt ggcttctcct    660 gtccctgctg tcgctccctc tgggcctccc agtcctgggc gcccaccac gcctcatctg    720 tgacagccga gtcctggaga ggtacctctt ggaggccaag gaggccgaga atatcacggt    780
gagacccctt cccagcaca ttccacagaa ctcacgctca gggcttcagg gaactcctcc    840
cagatccagg aacctggcac ttggtttggg gtggagttgg aagctagac actgccccc    900 tacataagaa taagtctggt ggccccaaac catacctgga aactaggcaa ggagcaaagc    960
cagcagatcc tacgcctgtg gccagggcca gagccttcag ggaccttga ctccccgggc   1020 tgtgtgcatt tcagacgggc tgtgctgaac actgcagctt gaatgagaat atcactgtcc   1080
cagacaccaa agttaatttc tatgcctgga agaggatgga ggtgagttcc ttttttttt   1140 tttttccttt cttttggaga atctcatttg cgagcctgat tttggatgaa agggagaatg   1200
```

```
atcgagggaa aggtaaaatg gagcagcaga gatgaggctg cctgggcgca gaggctcacg    1260
tctataatcc caggctgaga tggccgagat gggagaattg cttgagccct ggagtttcag    1320
accaacctag gcagcatagt gagatccccc atctctacaa acatttaaaa aaattagtca    1380
ggtgaagtgg tgcatggtgg tagtcccaga tatttggaag gctgaggcgg gaggatcgct    1440
tgagcccagg aatttgaggc tgcagtgagc tgtgatcaca ccactgcact ccagcctcag    1500
tgacagagtg aggccctgtc tcaaaaaaga aagaaaaaa gaaaaataat gagggctgta    1560
tggaatacgt tcattattca ttcactcact cactcactca ttcattcatt cattcattca    1620
acaagtctta ttgcatacct tctgtttgct cagcttggtg cttggggctg ctgaggggca    1680
ggagggagag ggtgacatgg gtcagctgac tcccagagtc cactccctgt aggtcgggca    1740
gcaggccgta gaagtctggc agggcctggc cctgctgtcg gaagctgtcc tgcggggcca    1800
ggccctgttg gtcaactctt cccagccgtg ggagcccctg cagctgcatg tggataaagc    1860
cgtcagtggc cttcgcagcc tcaccactct gcttcgggct ctgggagccc aggtgagtag    1920
gagcggacac ttctgcttgc cctttctgta agaagggggag aagggtcttg ctaaggagta    1980
caggaactgt ccgtattcct tccctttctg tggcactgca gcgacctcct gttttctcct    2040
tggcagaagg aagccatctc ccctccagat gcggcctcag ctgctccact ccgaacaatc    2100
actgctgaca ctttccgcaa actcttccga gtctactcca atttcctccg gggaaagctg    2160
aagctgtaca caggggaggc ctgcaggaca ggggacagat gaccaggtgt gtccacctgg    2220
gcatatccac cacctccctc accaacattg cttgtgccac accctccccc gccactcctg    2280
aaccccgtcg aggggctctc agctcagcgc cagcctgtcc catggctcga g            2331
```

<210> SEQ ID NO 69
<211> LENGTH: 619
<212> TYPE: DNA
<213> ORGANISM: Woodchuck hepatitis B virus
<220> FEATURE:
<221> NAME/KEY: misc_signal
<222> LOCATION: (1)..(619)
<223> OTHER INFORMATION: DNA of WPRE

<400> SEQUENCE: 69

```
tctgttcctg ttaatcaacc tctggattac aaaatttgtg aaagattgac tggtattctt     60
aactatgttg ctccttttac gctatgtgga tacgctgctt taatgccttt gtatcatgct    120
attgcttccc gtatggcttt cattttctcc tccttgtata atcctggtt gctgtctctt    180 tatgaggagt tgtggcccgt tgtcaggcaa cgtggcgtgg tgtgcactgt gtttgctgac    240 gcaacccca ctggttgggg cattgccacc acctgtcagc tcctttccgg gactttcgct    300
ttccccctcc ctattgccac ggcggaactc atcgccgcct gccttgcccg ctgctggaca    360
ggggctcggc tgttgggcac tgacaattcc gtggtgttgt cggggaagct gacgtccttt    420
ccatggctgc tcgcctgtgt tgccacctgg attctgcgcg gacgtccttt ctgctacgtc    480
ccttcggccc tcaatccagc ggaccttcct tcccgcggcc tgctgccggc tctgcggcct    540
cttccgcgtc ttcgccttcg ccctcagacg agtcggatct ccctttgggc cgcctccccg    600
cctgtttcgc ctcgggctc                                                619
```

<210> SEQ ID NO 70
<211> LENGTH: 27
<212> TYPE: DNA
<213> ORGANISM: Artificial Sequence
<220> FEATURE:

<223> OTHER INFORMATION: forward primer for promoter

<400> SEQUENCE: 70
ggatccggct gtcgttttgt tatgatt                                27

<210> SEQ ID NO 71
<211> LENGTH: 27
<212> TYPE: DNA
<213> ORGANISM: Artificial Sequence
<220> FEATURE:
<223> OTHER INFORMATION: reverse primer for promoter

<400> SEQUENCE: 71
ggatccaact aaaaggcaca gggaact                                27

<210> SEQ ID NO 72
<211> LENGTH: 29
<212> TYPE: DNA
<213> ORGANISM: Artificial Sequence
<220> FEATURE:
<223> OTHER INFORMATION: forward primer for 3' arm

<400> SEQUENCE: 72
gcggccgctt acaattcagt gtggggaat                              29

<210> SEQ ID NO 73
<211> LENGTH: 29
<212> TYPE: DNA
<213> ORGANISM: Artificial Sequence
<220> FEATURE:
<223> OTHER INFORMATION: reverse primer for 3' arm

<400> SEQUENCE: 73
gcggccgcca gctttattac aggcagagg                              29

<210> SEQ ID NO 74
<211> LENGTH: 35
<212> TYPE: DNA
<213> ORGANISM: Artificial Sequence
<220> FEATURE:
<223> OTHER INFORMATION: first forward primer for aS1 hEPO

<400> SEQUENCE: 74
gtgttgacaa ccatgggggt gcacggtgag tactc                       35

<210> SEQ ID NO 75
<211> LENGTH: 38
<212> TYPE: DNA
<213> ORGANISM: Artificial Sequence
<220> FEATURE:
<223> OTHER INFORMATION: second forward primer for aS1 hEPO

<400> SEQUENCE: 75
gatatctttt cttatatagg tgttgacaac catggggg                    38

<210> SEQ ID NO 76
<211> LENGTH: 26
<212> TYPE: DNA
<213> ORGANISM: Artificial Sequence
<220> FEATURE:
<223> OTHER INFORMATION: reverse primer for aS1 hEPO

<400> SEQUENCE: 76
gaattcatgg gacaggctgg cgctga                                 26

```
<210> SEQ ID NO 77
<211> LENGTH: 28
<212> TYPE: DNA
<213> ORGANISM: Artificial Sequence
<220> FEATURE:
<223> OTHER INFORMATION: forward primer for promoter

<400> SEQUENCE: 77
gtcgacagct gcaatgaaca tgtgggtg                                          28

<210> SEQ ID NO 78
<211> LENGTH: 31
<212> TYPE: DNA
<213> ORGANISM: Artificial Sequence
<220> FEATURE:
<223> OTHER INFORMATION: reverse primer for promoter

<400> SEQUENCE: 78
gatatccaaa ataaaaattt aggtctgaca g                                      31

<210> SEQ ID NO 79
<211> LENGTH: 30
<212> TYPE: DNA
<213> ORGANISM: Artificial Sequence
<220> FEATURE:
<223> OTHER INFORMATION: forward primer for 3' arm

<400> SEQUENCE: 79
gcggccgcat ggcatatgga agttcccagg                                        30

<210> SEQ ID NO 80
<211> LENGTH: 26
<212> TYPE: DNA
<213> ORGANISM: Artificial Sequence
<220> FEATURE:
<223> OTHER INFORMATION: reverse primer for 3' arm

<400> SEQUENCE: 80
ccgcggtggg aacttccata tgccat                                            26

<210> SEQ ID NO 81
<211> LENGTH: 24
<212> TYPE: DNA
<213> ORGANISM: Artificial Sequence
<220> FEATURE:
<223> OTHER INFORMATION: neo forward primer

<400> SEQUENCE: 81
gcggccgcgc gcgtcaggtg gcac                                              24

<210> SEQ ID NO 82
<211> LENGTH: 29
<212> TYPE: DNA
<213> ORGANISM: Artificial Sequence
<220> FEATURE:
<223> OTHER INFORMATION: neo reverse primer

<400> SEQUENCE: 82
cgatcggacg ctcagtggaa cgaaaactc                                         29

<210> SEQ ID NO 83
<211> LENGTH: 1902
<212> TYPE: DNA
<213> ORGANISM: Artificial Sequence
<220> FEATURE:
<223> OTHER INFORMATION: neo gene sequence
```

<400> SEQUENCE: 83

```
gcgcgtcagg tggcactttt cggggaaatg tgcgcggaac ccctatttgt ttattttct      60
aaatacattc aaatatgtat ccgctcatga acaataacc ctgataaatg cttcaataat    120
attgaaaaag gaagagtcct gaggcggaaa gaaccagctg tggaatgtgt gtcagttagg    180
gtgtggaaag tccccaggct ccccagcagg cagaagtatg caaagcatgc atctcaatta    240
gtcagcaacc aggtgtggaa agtccccagg ctccccagca ggcagaagta tgcaaagcat    300
gcatctcaat tagtcagcaa ccatagtccc gcccctaact ccgcccatcc cgcccctaac    360
tccgcccagt tccgcccatt ctccgcccca tggctgacta attttttta tttatgcaga    420
ggccgaggcc gcctcggcct ctgagctatt ccagaagtag tgaggaggct ttttggagg    480
cctaggcttt tgcaaagatc gatcaagaga caggatgagg atcgtttcgc atgattgaac    540
aagatggatt gcacgcaggt tctccggccg cttgggtgga gaggctattc ggctatgact    600
gggcacaaca gacaatcggc tgctctgatg ccgccgtgtt ccggctgtca gcgcaggggc    660
gcccggttct ttttgtcaag accgacctgt ccggtgccct gaatgaactg caagacgagg    720
cagcgcggct atcgtggctg gccacgacgg gcgttccttg cgcagctgtg ctcgacgttg    780
tcactgaagc gggaagggac tggctgctat tgggcgaagt gccggggcag gatctcctgt    840
catctcacct tgctcctgcc gagaaagtat ccatcatggc tgatgcaatg cggcggctgc    900
atacgcttga tccggctacc tgcccattcg accaccaagc gaaacatcgc atcgagcgag    960
cacgtactcg gatggaagcc ggtcttgtcg atcaggatga tctggacgaa gagcatcagg   1020
ggctcgcgcc agccgaactg ttcgccaggc tcaaggcgag catgcccgac ggcgaggatc   1080
tcgtcgtgac ccatggcgat gcctgcttgc cgaatatcat ggtggaaaat ggccgctttt   1140
ctggattcat cgactgtggc cggctgggtg tggcggaccg ctatcaggac atagcgttgg   1200
ctacccgtga tattgctgaa gagcttggcg gcgaatgggc tgaccgcttc ctcgtgcttt   1260
acggtatcgc cgctcccgat tcgcagcgca tcgccttcta tcgccttctt gacgagttct   1320
tctgagcggg actctggggt tcgaaatgac cgaccaagcg acgcccaacc tgccatcacg   1380
agatttcgat tccaccgccg ccttctatga aaggttgggc ttcggaatcg ttttccggga   1440
cgccggctgg atgatcctcc agcgcgggga tctcatgctg gagttcttcg cccaccctag   1500
ggggaggcta actgaaacac ggaaggagac aataccggaa ggaacccgcg ctatgacggc   1560
aataaaaaga cagaataaaa cgcacggtgt tgggtcgttt gttcataaac gcggggttcg   1620
gtcccagggc tggcactctg tcgataccc accgagaccc cattgggcc aatacgcccg   1680
cgtttcttcc ttttccccac ccaccccccc aagttcgggt gaaggcccag ggctcgcagc   1740
caacgtcggg gcggcaggcc ctgccatagc ctcaggttac tcatatatac tttagattga   1800
tttaaaactt cattttaat ttaaaaggat ctaggtgaag atccttttg ataatctcat   1860
gaccaaaatc ccttaacgtg agttttcgtt ccactgagcg tc                     1902
```

<210> SEQ ID NO 84
<211> LENGTH: 20
<212> TYPE: DNA
<213> ORGANISM: Artificial Sequence
<220> FEATURE:
<223> OTHER INFORMATION: forward primer for EPO

<400> SEQUENCE: 84

```
caaggaggcc gagaatatca                                                20
```

```
<210> SEQ ID NO 85
<211> LENGTH: 22
<212> TYPE: DNA
<213> ORGANISM: Artificial Sequence
<220> FEATURE:
<223> OTHER INFORMATION: reverse primer for EPO

<400> SEQUENCE: 85
aagtgtcagc agtgattgtt cg                                              22

<210> SEQ ID NO 86
<211> LENGTH: 21
<212> TYPE: DNA
<213> ORGANISM: Artificial Sequence
<220> FEATURE:
<223> OTHER INFORMATION: forward primer for Neo

<400> SEQUENCE: 86
gctacccgtg atattgctga a                                               21

<210> SEQ ID NO 87
<211> LENGTH: 21
<212> TYPE: DNA
<213> ORGANISM: Artificial Sequence
<220> FEATURE:
<223> OTHER INFORMATION: reverse primer for Neo

<400> SEQUENCE: 87
caacaccgtg cgttttattc t                                               21

<210> SEQ ID NO 88
<211> LENGTH: 21
<212> TYPE: DNA
<213> ORGANISM: Artificial Sequence
<220> FEATURE:
<223> OTHER INFORMATION: forward primer for human beta actin

<400> SEQUENCE: 88
cgtgggccgc cctaggcacc a                                               21

<210> SEQ ID NO 89
<211> LENGTH: 22
<212> TYPE: DNA
<213> ORGANISM: Artificial Sequence
<220> FEATURE:
<223> OTHER INFORMATION: reverse primer for human beta actin

<400> SEQUENCE: 89
ttggccttag ggttcagggg gg                                              22

<210> SEQ ID NO 90
<211> LENGTH: 22
<212> TYPE: DNA
<213> ORGANISM: Artificial Sequence
<220> FEATURE:
<223> OTHER INFORMATION: forward primer for mouse beta actin

<400> SEQUENCE: 90
tgtgatggtg ggaatgggtc ag                                              22

<210> SEQ ID NO 91
<211> LENGTH: 23
<212> TYPE: DNA
<213> ORGANISM: Artificial Sequence
<220> FEATURE:
<223> OTHER INFORMATION: reverse primer for mouse beta actin
```

```
<400> SEQUENCE: 91
tttgatgtca cgcacgattt tcc                                               23

<210> SEQ ID NO 92
<211> LENGTH: 21
<212> TYPE: DNA
<213> ORGANISM: Artificial Sequence
<220> FEATURE:
<223> OTHER INFORMATION: forward primer for EPO-WPRE

<400> SEQUENCE: 92
aactcttccg agtctactcc a                                                 21

<210> SEQ ID NO 93
<211> LENGTH: 22
<212> TYPE: DNA
<213> ORGANISM: Artificial Sequence
<220> FEATURE:
<223> OTHER INFORMATION: reverse primer for EPO-WPRE

<400> SEQUENCE: 93
ctcctcataa agagacagca ac                                                22

<210> SEQ ID NO 94
<211> LENGTH: 21
<212> TYPE: DNA
<213> ORGANISM: Artificial Sequence
<220> FEATURE:
<223> OTHER INFORMATION: forward primer for WPRE-3'arm

<400> SEQUENCE: 94
ttcctgttaa tcaacctctg g                                                 21

<210> SEQ ID NO 95
<211> LENGTH: 21
<212> TYPE: DNA
<213> ORGANISM: Artificial Sequence
<220> FEATURE:
<223> OTHER INFORMATION: reverse primer for WPRE-3'arm

<400> SEQUENCE: 95
taccaaaggc cataattgtg g                                                 21
```

GENE OF PORCINE ALPHA-S1 CASEIN, A PROMOTER OF THE SAME AND USE THEREOF

RELATED APPLICATIONS

This application is the National Stage of International Application. No. PCT/KR2009/003516, filed 29 Jun. 2009, which claims benefit of priority to KR 10-2008-0062765, filed 30 Jun. 2008.

TECHNICAL FIELD

The present invention relates to a porcine alpha-S1-casein gene, a porcine alpha-S1-casein gene promoter, an expression vector comprising the same, and a method for the production of a target protein using the same.

BACKGROUND ART

As an attempt to achieve maximum production of beneficial proteins (such as EPO with high economic value-added) in the medicinal field, mass production methods using cell culture techniques have been mainly used.

Korean Patent Application No. 94-12082 discloses an expression vector containing a modified recombinant human erythropoietin (rhEPO) gene. Despite feasibility of mass production of EPO in the animal cell line COS-7 (ATCC CRL 1651, African Green Monkey Kidney Cell) transformed with the same expression vector, this technique disadvantageously suffers from a cumbersome need of continuous transformation, which makes it unsuitable for industrial-scale production of a target protein. Further, Korean Patent No. 10-0232640 and Korean Patent No. 10-0434729 also disclose the production of EPO by transgenic cell line culture. However, these cell culture methods still suffer from disadvantages such as high production costs due to use of animal blood as a culture medium, and requirement of expert and sophisticated knowledge in the culture technique.

On the other hand, the production of beneficial proteins using transgenic animals is attracting a great deal of interest due to having advantages such as easy and convenient production, isolation and purification of target proteins and maintenance of superior activity, as compared to conventional cell culture techniques, because the target proteins are contained in body fluids secreted by animals. For example, Korean Patent No. 10-0358754 discloses a transgenic animal for the production of EPO in porcine milk, using a whey acidic milk protein promoter (WAP).

As a result of a variety of extensive and intensive studies and experiments to solve the problems as described above and to develop a mammary gland-specific promoter with high-efficiency expression of a target protein in milk, the inventors of the present invention succeeded in sequencing of an alpha-S1-casein gene and a promoter thereof. The present invention has been completed based on this finding.

DISCLOSURE OF THE INVENTION

Technical Problem

The present invention is intended to provide a porcine alpha-S1-casein gene and a promoter thereof, and a method for mass production of a target protein using the same.

Technical Solution

The present invention provides a porcine alpha-S1-casein gene.

The porcine alpha-S1-casein gene of the present invention specifically comprises a sequence as set forth in SEQ ID NO: 1, and the sequence of SEQ ID NO: 1 contains a promoter, and a sequence of a 3' untranslated region (UTR).

Further, the present invention provides a promoter of SEQ ID NO: 2 corresponding to a sequence of 1 to 9300 contiguous nucleotides, among the sequence of SEQ ID NO: 1, and the promoter is situated at the 5' end of the structural gene to thereby control expression of the structural gene.

The porcine alpha-S1-casein gene or promoter of the present invention may be one selected from functional equivalents thereof having one or more of disruption, deletion, insertion, point, substitution, nonsense, missense, polymorphism and rearrangement mutations in the sequence of SEQ ID NO: 1 or SEQ ID NO: 2.

Further, the present invention provides an expression vector comprising an entire or partial promoter of SEQ ID NO: 2. Preferably, the expression vector of the present invention contains a sequence of SEQ ID NO: 3 or SEQ ID NO: 4. The sequence of SEQ ID NO: 2, SEQ ID NO: 3 or SEQ ID NO: 4 serves as a promoter through the incorporation thereof into the vector and is referred to herein as a promoter sequence or porcine alpha-S1-caseiin gene promoter sequence. As used herein, the term "porcine alpha-S1-casein gene promoter" refers to a promoter derived from a porcine alpha-S1-casein gene.

SEQ ID NO: 3 and SEQ ID NO: 4 respectively correspond to a sequence consisting of 3568 to 9037 nucleotides and a sequence consisting of 4321 to 9300 nucleotides, among an entire genomic sequence of a porcine alpha-S1-caseiin gene of SEQ ID NO: 1, and contain in common an exon-1 region.

If necessary, the expression vector of the present invention may additionally contain regulatory factors at suitable sites or loci thereof. Examples of the regulatory factors may include another promoter, an enhancer, a selective marker, a 5'-untranslated region (UTR), a 3'-UTR, a polyadenylation signal, a ribosome-binding sequence, a sequence(s) capable of being inserted into a specific region of the genome, an intron and a woodchuck hepatitis virus posttranscriptional regulatory element (WPRE). Incorporation of such additional elements into the expression vector will provide various advantages such as easy and convenient construction of a transgenic cell line of interest, and maximized and stable expression of target proteins.

The selective marker is preferably a neomycin-resistant gene or the like. Alternatively, the selective marker may be one excised from a commercially available vector. The neomycin-resistant gene is a gene conferring resistance to G418 (2R,3S,4R,5R,6S)-5-amino-6-[(1R,2S,3S,4R,6S)-4,6-diamino-3-[(2R,3R,4R,5R)-3,5-dihydroxy-5-methyl-4-methylaminooxan-2-yl]oxy-2-hydroxycyclohexyl]oxy-2-(1-hydroxyethyl)oxane-3,4-diol), which is a reagent used in the construction of a cell line, and it may serve as an efficient selective marker upon the construction of an animal cell line that expresses a target protein under the control of a promoter.

The insulator is a factor that assists in the action of a regulatory factor adjacent to the promoter and facilitates position-independent expression of a protein. The insulator factor allows for stable expression of the protein under the control of a promoter. The insulator may be one excised from a commercially available vector.

WPRE is a regulatory factor that can contribute to the stabilization of mRNA molecules to thereby augment the synthesis of proteins. This regulator enables high expression of proteins under the control of a promoter. WPRE may also be a truncated one derived from a commercially available vector.

The expression vector of the present invention may further comprise a sequence as set forth in SEQ ID NO: 5 or SEQ ID NO: 6. The sequence of SEQ ID NO: 5 or ID NO: 6 forms the 3' arm of the vector, and assists in easy construction of a transformed cell line and maximization and stabilization of target protein expression.

SEQ ID NO: 5 and SEQ ID NO: 6 corresponds to a sequence ranging from nucleotide 26344 to nucleotide 30599 and from nucleotide 14447 to nucleotide 19401 among an entire genomic sequence of the porcine aloha-S1-casein gene of SEQ ID NO: 1, respectively.

The positions of the sequences of SEQ ID NOS: 3, 4, 5 and 6 among an entire genomic sequence of the porcine alpha-S1-casein gene are shown as FIG. 1.

The vector of the present invention is preferably constructed to contain the sequence of SEQ ID NO: 3 and the sequence of SEQ ID NO: 5.

Specifically, the vector of the present invention has a cleavage map as shown in FIG. 2. The pBC1-Pig αS1 casein vector was deposited with the Korean Collection for Type Cultures (KCTC), the Korean Research Institute of Bioscience and Biotechnology (KRIBB, Daejon, Korea), under Accession Number KCTC 11324BP. The expression vector pBC1-Pig αS1 casein of the present invention has a pBC1 vector as a basic backbone, to which a neomycin-resistant gene was fused as a selective marker.

The expression vector of the present invention may express a target protein by further incorporation of a target protein-encoding sequence at the 3' end of the promoter sequence.

The target protein is an industrially applicable beneficial protein and may be any protein that is used, for example, as an active ingredient in pharmaceuticals. Examples of the target protein may include EPO (erythropoietin), aldosterone, adrenocorticotropin, blood clotting factors, gonadotropin, insulin, prolactin, and vasopressin. Preferred is hEPO (human erythropoietin).

The present invention provides a vector having a cleavage map of FIG. 3, as a preferable example of an expression vector harboring a neomycin-resistant gene, an insulator, WPRE, and the like. Specifically, the pBC1-Pig αS1 casein+hEPO-WPRE vector was deposited with the Korean Collection for Type Cultures (KCTC), the Korean Research Institute of Bioscience and Biotechnology (KRIBB, Daejon, Korea), under Accession Number KCTC 11325BP.

The expression vector pBC1-Pig αS1 casein+hEPO-WPRE has a pBC1 vector as a basic backbone, wherein an hEPO-encoding gene is fused to a 3' end of the promoter region of the present invention, and WPRE is fused to a 3' end of the hEPO gene.

The expression vector of the present invention may be constructed in the form of a knock-in vector.

In the context of the present invention, the knock-in vector is a vector capable of inserting a target gene into a specific site or locus of a genome, and it contains a sequence homologous to a particular gene to be targeted, so as to result in homologous recombination therebetween. The knock-in vector of the present invention is an alpha-S1-casein targeting vector where a target protein-encoding nucleic acid sequence is inserted into an alpha-S1-casein gene present on the genome.

The knock-in vector of the present invention is preferably constructed to contain a sequence of SEQ ID NO: 4 and a sequence of SEQ ID NO: 6.

The knock-in vector may be constructed to select transgenic cells using a positive and/or negative selective marker, if necessary. The selective marker is intended to select vector-transformed cells and may employ genes capable of conferring selectable phenotypes, such as drug resistance, nutritional auxotrophy, resistance to cytotoxic agents, and expression of surface proteins.

The selective marker may be broadly classified into a positive selective marker and a negative selective marker.

As used herein, the term "positive selective marker" refers to a gene that makes cells expressing the positive selective marker to survive against a selective agent, so that it is capable of conferring positive selective characteristics for the cells expressing that marker. Examples of the positive selective marker may include neomycin (Neo)-resistant gene, hygromycin (Hyg)-resistant gene, etc.

The term "negative selective marker" refers to a gene which removes cells with random integration, so that it is capable of conferring negative selection characteristics for the cells expressing that marker. Examples of the negative selective marker include Herpes simplex virus-thymidine kinase (HSV-tk) gene, hypoxanthine phosphoribosyl transferase (Hprt) gene, cytosine deaminase gene, Diphtheria toxin gene, etc. The negative selective marker is positioned at the 5' terminus of the promoter region or at the 3' terminus of the 3' arm.

The positive selective marker and the negative selective marker may have independent promoters, poly(A), and the like. Examples of the promoter that can be used in the present invention may include simian virus 40 (SV40), mouse mammary tumor virus (MMTV) promoter, HIV long terminal repeat (LTR) promoter, Moloney virus, Cytomegalovirus (CMV) promoter, Epstein-Barr virus (EBV) promoter, Rous sarcoma virus (RSV) promoter, phosphoglycerate kinase (PGK) promoter, etc.

When homologous recombination takes place between the knock-in vector of the present invention and the alpha-S1-casein gene on the genome, a target protein-encoding nucleic acid on the vector is integrated into the alpha-S1-casein-casein genomic gene of the host cell and is then expressed instead of the alpha-S1-casein protein of the host cell.

The present invention provides a vector having a cleavage map of FIG. 4, as a preferable example of a knock-in vector employing a neomycin-resistant gene as a positive selective marker and Herpes simplex virus-thymidine kinase (HSV-tk) as a negative selective marker. Specifically, the Pig αS1 casein-hEPO knock-in vector was deposited with the Korean Collection for Type Cultures (KCTC), the Korean Research Institute of Bioscience and Biotechnology (KRIBB, Daejon, Korea), under Accession Number KCTC 11326BP.

The Pig β casein-hEPO knock-in vector has a Lox A neo vector as a basic backbone, wherein, hEPO is fused to a 3' end of the promoter (referring to the Pig β casein αS1 casein 5' arm shown FIG. 4), a neomycin-resistant gene as a positive selective marker is fused to a 3' end of hEPO, a 3' arm (referring to the Pig αS1 casein 3' arm shown FIG. 4) is fused to a 3' end of the neomycin-resistant gene, and a Herpes simplex virus-thymidine kinase (HSV-tk) gene (TK) is fused to a 3'end of the 3' arm.

The vector of the present invention may be constructed by any conventional gene recombination technique well-known in the art. Site-specific DNA cleavage and splicing may be carried out using conventional enzymes known in the art.

Further, the present invention provides an animal somatic cell transformed by introduction of the expression vector of the present invention.

The animal somatic cell to which the vector of the present invention will be introduced may be a primary, secondary or permanent cell derived from suitable animals including pigs.

Intracellular introduction of the vector of the present invention may be carried out by any conventional intracellular introduction method of nucleic acids, that is, techniques known in the art, such as electroporation, calcium phosphate co-precipitation, retroviral infection, microinjection, DEAE-dextran facilitated transfection, cationic liposome-mediated transfection, etc. When it is desired to perform intracellular introduction of a vector, the vector may be introduced in the form of a linearized vector obtained or in the form of a plasmid-free linearized vector, by digestion of a circular vector with suitable restriction enzymes.

The promoter gene of the present invention specifically expresses a target protein only in mammary gland tissues. Casein accounts for 90% of protein components in porcine milk and is broadly categorized into alpha-, beta- and gamma-casein. Since Alpha-casein, being categorized into alpha-S1-casein and kappa-casein, contributes to a considerable portion of protein components, amounting to 70%, and alpha-S1-casein accounts for 55% of alpha-casein. Thus, the vector employing the porcine alpha-S1-casein promoter may be constructed to exhibit mammary gland-specific expression of exogenous target proteins in lactating animals, particularly pigs.

Further, the present invention provides an animal embryo produced by nuclear transfer of a nucleus of an animal somatic cell, transformed with the expression vector of the present invention, into an enucleated egg.

As used herein, the term "nuclear transfer" refers to implantation of a cell nucleus into an enucleated egg. The offspring produced by implantation of the nucleus-transferred fertilized egg (or embryo) are genetically completely identical clones because genetic materials of a nuclear donor cell were thoroughly and intactly transferred into a nuclear recipient cytoplasm.

Further, the present invention provides a transgenic animal obtained by implantation of an animal embryo of the present invention.

Specifically, the introduction of the expression vector may be performed by, for example, a microinjection technique of injecting a gene into the male pronucleus of a zygote in a pronuclear stage immediately after fertilization, a stem cell insertion technique of inserting a gene into a embryonic stem cell and transferring the cell into a blastocyst embryo, a retroviral insertion technique of injecting a gene into an embryo using a retroviral vector, or a sperm-mediated gene transfer technique of injecting a gene into the testis of a male to insert the gene into the sperm and transferring the sperm into an oocyte. Preferred is the microinjection technique.

The present invention also provides a transgenic animal obtained by implantation of the animal embryo of the present invention. Examples of an animal that can be transformed with the expression vector of the present invention include all kinds of lactating animals, including pigs, mouse, cow, sheep and goat.

Production of a transgenic animal using the expression vector of the present invention is carried out by a conventional method known in the art.

For example, when an animal to be transformed is a mouse, embryos (or fertilized eggs) are collected from a healthy individual, and the expression vector of the present invention is introduced into the embryos. Thereafter, a pseudopregnant mouse is obtained using a vasoligated mouse, the embryos are implanted into the oviduct of the pseudopregnant mouse as a surrogate mother (or recipient), and transgenic mice are then selected from among the offspring obtained from the surrogate mother.

When an animal to be transformed is a pig, porcine follicular oocytes are collected from a healthy animal and cultured in an in vitro maturation (IVM) medium. Further, the expression vector of the present invention is introduced into donor somatic cells, collected and cultured from the porcine fetus, and somatic cells introduced with the vector are selected and cultured. The in vitro matured eggs are enucleated, the donor cells are injected into the enucleated space of the eggs cells from which nuclei were removed, and the donor cells and the cytoplasm of the nucleus-transferred oocytes are fused by an electrofusion technique, followed by in vitro culture of the fusion. The resulting cloned embryos are implanted into the recipient pigs which were subjected to superovulation treatment, and the transgenic pigs are then selected from among the offspring obtained from the recipient pigs.

Thereafter, milk is collected from the individual where correct transformation was confirmed, and a target protein is isolated and purified therefrom to produce a final protein (A. Gokana, J. J. Winchenn, A. Ben-Ghanem, A. Ahaded, J. P. Cartron, P. Lambin (1997) Chromatographic separation of recombinant human erythropoietin isoforms, Journal of Chromatography, 791, 109-118).

In the production of the target protein of the present invention, isolation and purification of the protein may be carried out by a conventional method known in the art, for example, filtration or chromatography may be used for the isolation and purification of the target protein.

The thus-constructed transgenic animal of the present invention can express the target protein in milk.

Therefore, the porcine alpha-S1-casein gene of the present invention, the promoter thereof, and the expression vector and transgenic animal using the same can be beneficially used for the production of target proteins.

Details relating to genetic engineering techniques in the present invention can be found in the following literature: Sambrook, et al. Molecular Cloning, A Laboratory Manual, Cold Spring Harbor Laboratory Press, Cold Spring Harbor, N.Y., (2001); and Frederick M. Ausubel et al., Current Protocols in Molecular Biology volume 1, 2, 3, John Wiley & Sons, Inc., (1994).

Advantageous Effects

The porcine alpha-S1-casein gene promoter facilitates mammary gland-specific expression of a target protein. Therefore, a promoter of the present invention and an animal transformed with an expression vector constructed using the same promoter enable high-concentration secretion of the target protein in milk, which consequently will provide benefits for the production of useful proteins that are medically and pharmaceutically valuable.

MODE FOR INVENTION

Figure 1:
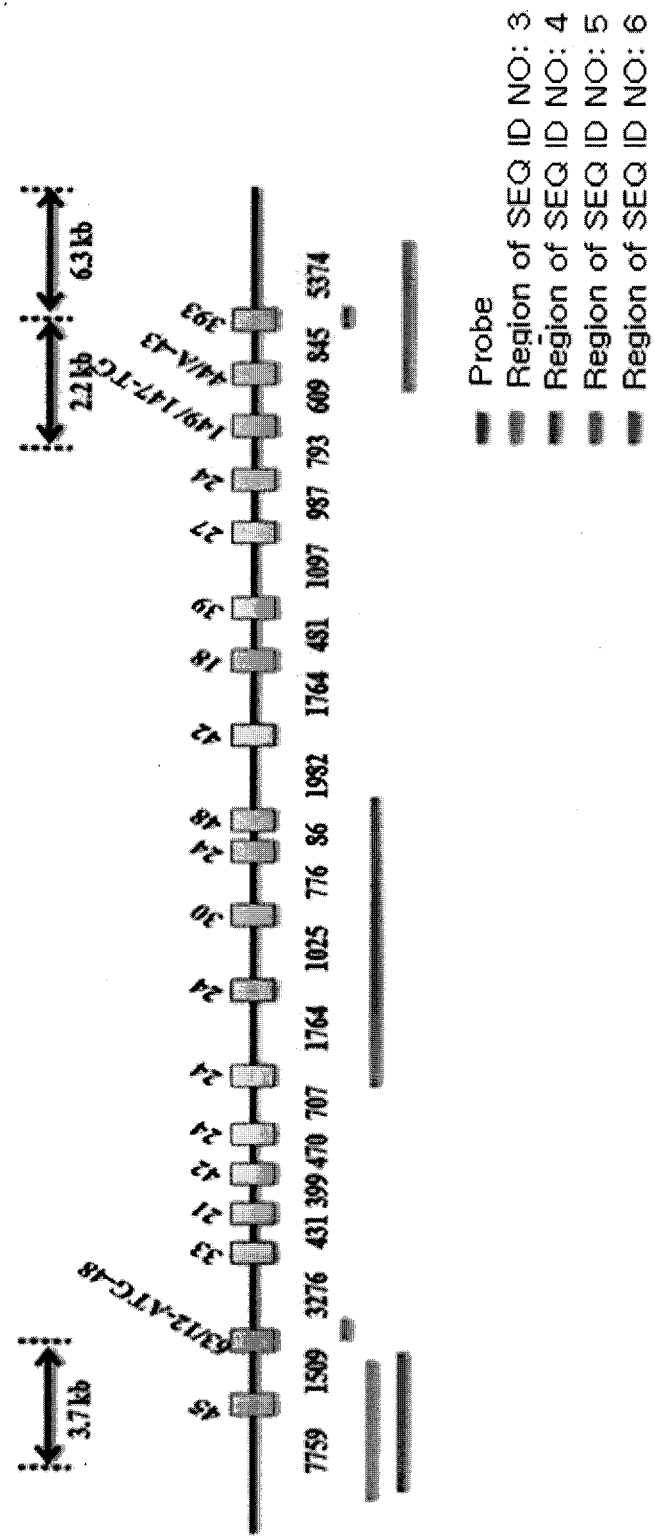
FIG. 1 shows positions of probes used to find the sequence of a porcine alpha-S1-casein gene in accordance with the present invention and the positions of sequences found by the probes.

Now, the present invention will be described in more detail with reference to the following Examples. These examples are provided only for illustrating the present invention and should not be construed as limiting the scope and spirit of the present invention.

Example 1: Isolation and Cloning of Porcine Alpha-S1-Casein Gene

In order to construct a mammary gland-specific gene of the present invention, a porcine alpha-S1-casein gene (pig αS1 casein gene) was sequenced using a pig genomic DNA library (Promega) and bacterial artificial chromosome (BAC) clones provided by The National Livestock Research Institute (77 Chuksan-gil, 564 Omokchun-dong, Gwonsun-gu, Suwon, Korea).

1) Sequencing of Porcine Alpha-S1-Casein Gene Using Pig Genomic DNA Library

Because the sequence of a porcine alpha-S1-casein gene was not yet found, the sequences of primers to be used for the PCR amplification of porcine alpha-S1-casein were constructed with reference to high homology and highly conserved regions between species by comparing the sequences of the alpha-S1-casein cDNAs of humans, cow, horses and mice, the sequences of which were found.

Using a 5' UTR forward primer (5'-TGACAACCAT-GAAACTTCTCAT-3; SEQ ID NO: 8), a 5' UTR reverse primer (5'-GTTCCTGATGCCTGAGAGGA-3; SEQ ID NO: 9), a 3' UTR forward primer (5'-AACCATTTTATCT-GAAGACTTTG-3'; SEQ ID NO: 10) and a 3' UTR reverse primer (5'-TCTCAGTCACTGCACACAATT-3'; SEQ ID NO: 11), porcine genomic DNA was subjected to PCR amplification (PT-200, BIO-RAD) under the following conditions: denaturation at 94° C. for 5 min; followed by 35 cycles of denaturation at 94° C. for 30 sec, primer annealing at 56° C. for 30 sec, and extension at 72° C. for 5 min. As a result, a PCR product comprising a 3.3-kb sequence (SEQ ID NO: 12) for the 5' UTR and a 303-bp sequence (SEQ ID NO: 13) for the 3' UTR was obtained. The obtained product was cloned into a pGEM-T vector (Promega, USA) and then sequenced, thereby confirming that the product was a portion of the porcine alpha-S1-casein gene. The 3.3-kb fragment at the 5' UTR and the 303-bp fragment at the 3' UTR were sequenced.

In order to make a 5' UTR probe from the identified 3.3-kb sequence of the porcine alpha-S1-casein gene, PCR amplification (PT-200, BIO-RAD) was performed using the forward primer 5'-TGACAACCATGAAACTTCTCAT-3' (SEQ ID NO: 14) and the reverse primer 5'-CTAAGACTCTCATACTGAGTG-3' (SEQ ID NO: 15) under the following conditions: denaturation at 94° C. for 5 min; and then 35 cycles of denaturation at 94° C. for 30 sec, primer annealing at 56° C. for 30 sec, and extension at 72° C. for 30 sec. As a result, a 551-bp product (SEQ ID NO: 16) was obtained.

In order to make probes to be used to identify the sequence of porcine alpha-S1-casein, 100 ng of the above-prepared PCR product, comprising the 551-bp 5' UTR and the 303-bp 3' UTR, was boiled for 5 min, and then cooled on ice, so that it was denatured. The denatured DNA was added to a reaction buffer containing primers, dNTP and [α-$^{32}$P] dCTP (3000 Ci/nmol, NEN), and then a Klenow fragment (Promega, USA) was added thereto and allowed to react at 37° C. for 1 hour. Then, the reaction solution was purified using a Sephadex G-50 column, thereby preparing a $^{32}$P-labeled porcine alpha-S1-casein gene probe.

In order to identify the porcine alpha-S1-casein gene, a porcine genomic library was screened. In this Example, a pig genomic DNA library (Promega) was used.

Host bacteria to be introduced with the library were prepared in the following manner.

A bacterial colony was inoculated into 5 ml of 0.2% maltose-containing LB medium (Scharlau, Spain) and cultured overnight at 37° C. 1% of the culture was transferred into 50 ml of fresh LB medium containing 0.2% maltose and was cultured for 2.5 hours. When the absorbance at 600 nm reached about 0.5, the culture was centrifuged at 2500 rpm for 10 minutes. The resulting cell precipitate was suspended in 10 ml of sterilized magnesium sulfate solution to a final concentration of $1×10^{10}$ cells/Ml and stored at 4° C. until use.

For titration, the library was serially diluted in SM buffer (0.1M NaCl, 8 mM MgSO$_4$, 50 mM Tris-HCl (pH 7.5), 0.01% gelatin} at various concentrations. A solid LB medium-containing plate was warmed in an incubator at 37° C., and the top agar was melted and placed in a water bath at 48° C. 10 μl of each of the phage solutions diluted at various concentrations was mixed with 100 μl of the above-prepared host bacteria and infected with the host bacteria at 37° C. The phage-infected phage bacteria were added to the top agar and shaken well, and then poured onto the above-prepared LB medium. After 15 minutes, the plate was overturned upside down and cultured in an incubator overnight at 37° C. On the medium of the plate which had been cultured overnight, plaques were formed, indicating that the phage replicated the library DNA and then lysed the host bacteria. The medium was cooled at 4° C. for 1 hour or more for use in a subsequent experiment.

NC filters (Amersham Biosciences; GB) with serial numbers were prepared, and the above-prepared DNA library plate was covered with the filter in such a manner that the middle portion of the filters was first contacted.

The filters were pricked with a needle in a vertical direction so as to mark a position, and after one minute, the filters were carefully separated from the medium.

Each of the filters was immersed successively in denaturation solution (0.5 M NaOH, 1.5 M NaCl; Sigma, USA), neutralization solution (1 M Tris-HCl (pH 7.5), 1.5 M NaCl; Sigma, USA) and 2×SSC solution (0.3 M NaCl, 0.03 M sodium citrate, Sigma, USA) for a minute for each solution, and then placed in an oven at 80° C. for 2 hours, such that the transferred library DNA was completely immobilized.

Each of the immobilized filters was placed in a vinyl bag, and a prehybridization solution (40 ml of 50% formamide, 20 ml of 20×SSPE (saline-sodium phosphate-EDTA buffer), 8 ml of 50×Denhardt's solution, 1.2 ml of 100 ng/ml salmon sperm DNA, 1.2 ml of 10% SDS (sodium dodecyl sulfate), 0.6 ml of distilled water; Sigma, USA) was added thereto. Then, the filter was subjected to prehybridization with slow stirring at 68° C. for 1 hour. After the prehybridization, 100 ng of the above-prepared probe was added to each filter which was then subjected to hybridization with slow stirring at 68° C. for 18 hours. After the hybridization, a process of immersing the filter in 0.1% SDS-containing 2×SSC solution and washing the filter with shaking at 65° C. for 10 minutes was repeated twice. After the washing, each of the filters was dried in air and subjected to autoradiography. By comparing the autoradiographic results with the plate, a plaque showing a positive sign was selected. The selected plaque was placed in 500 µl of SM buffer solution, and one drop of chloroform was added to and well mixed with the solution, and the mixture was stored at 4° C. This screening process was repeated two times, and clones showing a positive sign were finally obtained. The obtained clones were subjected to PCR amplification (PT-200, BIO-RAD) using a pair of the primers (a forward primer (SEQ ID NO: 14) and a reverse primer (SEQ ID NO: 15)), which were used to make the probes, and a pair of T7 and SP6 primers (Cosmo, Korea), under the following conditions: denaturation at 94° C. for 5 min; and then 35 cycles of denaturation at 94° C. for 30 sec, primer annealing at 56° C. for 30 sec, and extension at 72° C. for 5 min. As a result of the PCR amplification, a 5' product of 3.7 kb (SEQ ID NO: 17) was obtained with the 5' UTR probe of 551 bp, and a 5' product of 303 kb (SEQ ID NO: 18) and a 3' product of 6.3 kb (SEQ ID NO: 19) were obtained with the 3' UTR probe of 303 bp. The PCR products were cloned into a pGEM-T vector (Promega, USA), thereby obtaining a complete nucleotide sequence.

Sequencing of the obtained gene was performed by Solgent (Korea).

2) Sequencing of Porcine Alpha-S1-Casein Using BAC Clones

Using the primers (SEQ ID NO: 14 and SEQ ID NO: 15) used to make the probes in the sequencing process carried out using the pig genomic DNA library, the gene was subjected to PCR amplification ((PT-200, BIO-RAD) under the following conditions: denaturation at 94° C. for 5 min; and then 35 cycles of denaturation at 94° C. for 30 sec, primer annealing at 56° C. for 30 sec, and extension at 72° C. for 30 sec. As a result, four clones (155F1, 188A9, 616B6, and 874E5) were obtained. The obtained clones were continuously sequenced, thereby identifying a complete nucleotide sequence (SEQ ID NO: 41) of a total of 33 kb.

3) Sequencing of Alpha-S1-Casein from Berkshire Pig

Based on the DNA sequence of porcine alpha-S1-casein obtained from the pig genomic DNA library analysis and the Bac clones, alpha-S1-casein was sequenced from the genomic DNA of Berkshire pigs. The genomic DNA used herein was one separated from porcine somatic cells, obtained from the Advanced Swine Research Institute (Gyeongsangnam-do, Korea), using a genomic DNA extraction kit (cat. No. 17231; iNtRON, Korea). The 33-kb sequence of alpha-S1-casein determined in the above section 2) was divided into a total of a total of seven parts (4.6 kb, 5.7 kb, 4.9 kb, 5.4 kb, 5.3 kb, 4.7 kb; and 4.4 kb) which correspond to primer sequences (SEQ ID NO: 42 to SEQ ID NO: 55) for use in PCR amplification (PT-200, BIO-RAD). PCR was carried out as follows: one cycle of denaturation at 94° C. for 5 minutes; and 35 cycles of denaturation at 94° C. for 30 seconds, primer annealing at 56° C. for 30 seconds and elongation at 72° C. for 4 minutes.

The resulting PCR products were each cloned into a pGEM-T vector, followed by sequencing. Analysis of sequences was conducted by Sogent (Korea) using a Bioedit program.

TABLE 1

| SEQ ID NO | Sequencing primer |
|---|---|
| 20 | 5'-TAACGAATCCAACTAGGAACC-3' |
| 21 | 5'-TCCTTCTCCAACCCTATATTC-3' |
| 22 | 5'-TGAGAGGGGAATAGAAAGAAC-3' |
| 23 | 5'-TATCAATAGGTCTCAGAAGATC-3' |
| 24 | 5'-TAGACTTCGAGTTTGGAGGG-3' |
| 25 | 5'-TATAAGGCACAAATGAGCCCTT-3' |
| 26 | 5'-AAATGCTCAACATCCCTGATTA-3' |
| 27 | 5'-TATTCCGTGTTCATGGATTGG-3' |
| 28 | 5'-AAGTATTCTCCACTGCCTTAC-3' |

TABLE 1-continued

| SEQ ID NO | Sequencing primer |
|---|---|
| 29 | 5'-TGTGAGTATGGTAGAGAATTT-3' |
| 30 | 5'-CTATTGTGAATAGAGCTGCAAT-3' |
| 31 | 5'-GTGTGAGAGTGTGTACCAGTT-3' |
| 32 | 5'-TGTTCCCTTGTGATATATAGC-3' |
| 33 | 5'-CTTGTTCCCACAGTTCAAATG-3' |
| 34 | 5'-TAGATACCTCCACCAAGAGC-3' |
| 35 | 5'-TTCTCAGGTTTCCTGAGGTG-3' |
| 36 | 5'-GTGCACATTTACATACTGATAG-3' |
| 37 | 5'-ATCATCAATGAACTGAACAGGGT-3' |
| 38 | 5'-TTGAGACCTAAGTCACAGCTA-3' |
| 39 | 5'-TCCATAATAATTTATGTCAAGGG-3' |
| 40 | 5'-TAAGGCAAAATGTGCATGAGTG-3' |

TABLE 2

| | Primer | SEQ ID NO |
|---|---|---|
| Forward 4.6 kb | 5'-AGGATTACAAGATTGCTGTTGGA-3' | 42 |
| Reverse 4.6 kb | 5'-AAAATCGTCAACTACCCTGATTA-3' | 43 |
| Forward 5.7 kb | 5'-AGCTGCAATGAACATGGGTG-3' | 44 |
| Reverse 5.7 kb | 5'-CACCCACATGTTCATTGCAGCT-3' | 45 |
| Forward 4.9 kb | 5'-CACTCAGTATGAGAGTCTTAG-3' | 46 |
| Reverse 4.9 kb | 5'-CTGTTCAGTTCATTGATGATTTC-3' | 47 |
| Forward 5.4 kb | 5'-TTTGGTTCTGCTGTGCCATAA-3' | 48 |
| Reverse 5.4 kb | 5'-GTAGAGCTTAGAGTTCAACTC-3' | 49 |
| Forward 5.3 kb | 5'-CACTCAGGATGAGATTCTCTA-3' | 50 |

TABLE 2-continued

| Primer | | SEQ ID NO |
|---|---|---|
| Reverse 5.3 kb | 5'-AACTGATTGATGACTACTATGTT-3' | 51 |
| Forward 4.7 kb | 5'-AGATCTGACACCTTCTAATTAC-3' | 52 |
| Reverse 4.7 kb | 5'-GTGTATTCCTGCACAGCAAC-3' | 53 |
| Forward 4.4 kb | 5'-GTCAAACTGCCTTCTAGAGTC-3' | 54 |
| Reverse 4.4 kb | 5'-GTAGACTTATGTGAAGCTCTG-3' | 55 |

As a result, the porcine beta-casein genomic DNA sequence (SEQ ID NO: 1) of the Berkshire pig and sequence information thereof were successfully acquired.

The sequence of SEQ ID NO: 1 is the entire genomic sequence of the porcine alpha-S1-casein gene and has a length of 33248 bp. In the sequence of SEQ ID NO: 1, the structural gene region is a sequence ranging from nucleotide 7760 to nucleotide 27875, the initiation codon is a sequence ranging from nucleotide 9326 to nucleotide 9328, and the termination codon is a sequence ranging from nucleotide 25982 to 25983 and nucleotide 26593. Also, the 5' UTR region is a sequence ranging from nucleotide 7760 to nucleotide 7804 and from nucleotide 9314 to nucleotide 9325, the 3' UTR region is a sequence ranging from nucleotide 26594 to nucleotide 26636 and nucleotide 27482 to nucleotide 27875, and the poly(A) signal region is a sequence ranging from nucleotide 27855 to nucleotide 27860. The exon region is a sequence ranging from nucleotide 7760 to nucleotide 7804, from nucleotide 9314 to nucleotide 9376, from nucleotide 12653 to nucleotide 12685, from nucleotide 13117 to nucleotide 13137, from nucleotide 13537 to nucleotide 13578, from nucleotide 14049 to nucleotide 14072, from nucleotide 14780 to nucleotide 14803, from nucleotide 16568 to nucleotide 16591, from nucleotide 17617 to nucleotide 17646, from nucleotide 18423 to nucleotide 18446, from nucleotide 18533 to nucleotide 18580, from nucleotide 20563 to nucleotide 20604, from nucleotide 22369 to nucleotide 22386, from nucleotide 22868 to nucleotide 22906, from nucleotide 24004 to nucleotide 24030, from nucleotide 25018 to nucleotide 25041, from nucleotide 25835 to nucleotide 25983, from nucleotide 26593 to nucleotide 26636, and from nucleotide 27482 to nucleotide 27875. The intron region is a sequence ranging from nucleotide 7805 to nucleotide 9313, from nucleotide 9377 to nucleotide 12652, from nucleotide 12686 to nucleotide 13116, from nucleotide 13138 to nucleotide 13536, from nucleotide 13579 to nucleotide 14018, from nucleotide 14073 to nucleotide 14779, from nucleotide 14804 to nucleotide 16567, from nucleotide 16592 to nucleotide 17616, from nucleotide 17647 to nucleotide 18422, from nucleotide 18447 to nucleotide 18532, from nucleotide 18581 to nucleotide 20562, nucleotide 20605 to nucleotide 22368, from nucleotide 22387 to nucleotide 22867, from nucleotide 22907 to nucleotide 24003, from nucleotide 24031 to nucleotide 25017, from nucleotide 25042 to nucleotide 25834, from nucleotide 25984 to nucleotide 26592, and from nucleotide 26637 to nucleotide 27481. Also, the coding sequence (CDS) is a sequence ranging from nucleotide 9326 to nucleotide 9376, from nucleotide 12653 to nucleotide 12685, from nucleotide 13117 to nucleotide 13137, from nucleotide 13537 to nucleotide 13578, from nucleotide 14049 to nucleotide 14072, from nucleotide 14780 to nucleotide 14803, from nucleotide 16568 to nucleotide 16591, from nucleotide from 17617 to nucleotide 17646, from nucleotide 18423 to nucleotide 18446, from nucleotide 18533 to nucleotide 18580, from nucleotide 20563 to nucleotide 20604, from nucleotide 22369 to nucleotide 22386, from nucleotide 22868 to nucleotide 22906, from nucleotide 24004 to nucleotide 24030, from nucleotide 25018 to nucleotide 25041, from 25835 to nucleotide 25983 and nucleotide 26593.

In addition, an alpha-S1-casein amino acid sequence (SEQ ID NO: 7) was analyzed.

FIG. 1 shows the positions of the probes and the positions and structures of the sequences identified by the probes.

In FIG. 1, "63/12-ATG-48" indicates that ATG (initiation codon) is located after a sequence of 12 nucleotides among 63 nucleotides of exon 2 of porcine alpha-S1-casein, followed by 48 nucleotides of exon 2. Also, "149/147-TG" indicates that TG of TGA (termination codon) is located after a sequence of 147 nucleotides among 149 nucleotides of exon 17 of porcine alpha-S1-casein. In addition, "44/A-43" indicates that A of the termination codon is located among 44 nucleotides of exon 18 of porcine alpha-S1-casein, followed by 43 nucleotides of exon 18.

The analyzed porcine alpha-S1-casein sequence and information thereof were registered in NCBI (EU025875).

Example 2: Construction of pBC1-Pig αS1 Casein Cloning Vector

A cloning vector was constructed by respectively replacing a goat beta-casein promoter region and a 3' genomic DNA region with the porcine alpha-S1-casein sequence and the 3' arm sequence in a vector having substitution of an ampicillin-resistant gene of a pBC1 vector (Invitrogen, USA) with a neomycin-resistant gene {A "neo" gene capable of conferring drug resistance to G418 was obtained from a pEGFP-N1 vector (Clontech, USA) by amplification of a 1.9-kb PCR product (SEQ ID NO: 83) using a forward primer 5'-GCGGCCGCGCGCGTCAGGTGGCAC-3' (SEQ ID NO: 81) and a reverse primer 5'-CGATCGGACGCTCA-GTGGAACGAAAACTC-3' (SEQ ID NO: 82), and was then cloned into a pGEM T-easy vector. The 1.9-kb neo gene cloned into the T-vector was digested with restriction endonucleases Not I and Pvu I to prepare an insert. In addition, an amp gene (ampicillin-resistance gene) region of the pBC1 vector was removed by Not I and Pvu I cleavage to prepare a vector. The resulting insert fragment and vector part were ligated to construct a pBC1 vector into which the neo gene (neomycin-resistance gene) was inserted}.

The porcine alpha-S1-casein promoter sequence of 5.5 kb (SEQ ID NO: 3) and the 3' arm sequence of 4.3 kb (SEQ ID NO: 5) were subjected to PCR amplification (PT-200, BIO-RAD) using primer sequences (SEQ ID NO: 56 to SEQ ID NO: 59). PCR was carried out as follows: one cycle of denaturation at 94° C. for 5 minutes; and 35 cycles of denaturation at 94° C. for 30 seconds primer annealing at 56° C. for 30 seconds and elongation at 72° C. for 5 minutes. Each of the resulting PCR products was cloned into a pGEM-T vector (Promega, USA).

TABLE 3

|  | Primer | SEQ ID NO |
|---|---|---|
| Forward primer for amplification of promoter | 5'-GGATCCGGCTGTCGTTTTGTTATGATT-3' | 56 |
| Reverse primer for amplification of promoter | 5'-CTCGAGAACTAAAAGGCACAGGGAACT-3' | 57 |
| Forward primer for amplification of 3' arm amplification | 5'-CTCGAGTTACAATTCAGTGTGGGGAAT-3' | 58 |
| Reverse primer for amplification of 3' arm amplification | 5'-GCGGCCGCCAGCTTTATTACAGGCAGAGG-3' | 59 |

In order to avoid possible Bam HI digestion, two Bam HI sites (GGATCC) present in the porcine beta-casein promoter sequence were subjected to repetitive point mutations as follows. For introduction of point mutations, one of two restriction sites was first selected and the corresponding primer was constructed. The pGEM-T vector DNA containing a porcine alpha-S1-casein 5' promoter region was purified and then subjected to PCR amplification using 20 ng of template DNA and a pair of point mutation primers. PCR was carried out as follows: one cycle of denaturation at 95° C. for 30 seconds; and 15 cycles of denaturation at 95° C. for 30 seconds, primer annealing at 55° C. for 1 minute and elongation at 72° C. for 8.5 minutes. In order to eliminate the template (with no introduction of point mutation) DNA, 1 µl of Mutazyme™ was added thereto, followed by reaction at 37° C. for 1 hour. 10 µl of the reaction product was transformed into DH10B competent cells (Invitrogen, USA) which were then plated on an LB+Ampicillin solid medium and cultured at 37° C. for 20 hours. Colonies gown on the LB+Ampicillin solid medium were cultured on an LB+Ampicillin liquid medium, followed by DNA purification and sequencing to confirm whether Bam HI sites underwent point mutations (GGATCC→GGACCC). Using DNA of colonies having the point mutation at one restriction site, the other Bam HI site was also made to have a point mutation according to the same method. The point mutation method used herein was carried out using a Site-Directed Mutagenesis kit (iNtRON).

Primer sequences used in the point mutation of the promoter sequence are shown in Table 4 below.

TABLE 4

|  | Primer | SEQ ID NO |
|---|---|---|
| Forward primer for primary point mutation | 5'-TATATACTACATCTTCCGGGTCCAATCATCTGTTGATGG-3' | 60 |
| Reverse primer for primary point mutation | 5'-CCATCAACAGATGATTGGACCCGGAAGATGTAGTATATA-3' | 61 |
| Forward primer for secondary point mutation | 5'-AAGACGTGGCTTGGGTCCCACGTTGCTGT-3' | 62 |
| Reverse primer for secondary point mutation | 5'-ACAGCAACGTGGGACCCAAGCCACGTCTT-3' | 63 |

The porcine alpha-S1-casein promoter sequence present in the pGEM-T vector was digested with Bam HI and Xho I to prepare an 8.5-kb vector. In addition, the sequence region comprising the 3' arm was digested with Xho I and Not I to prepare a 4.3-kb insert (SEQ ID NO: 5). The resulting two restriction fragments were ligated to clone a pGEM-T-pig αS1 casein 5'+3' vector.

The pBC1 vector was digested with Bam HI and Not I to prepare a 10-kb vector, and the pGEM-T-pig αS1 casein 5'+3' vector was digested with Bam HI and Not I to prepare a 9.8-kb insert. The resulting two restriction fragments were ligated to construct a pBC1-pig αS1 casein cloning vector.

Figure 2:
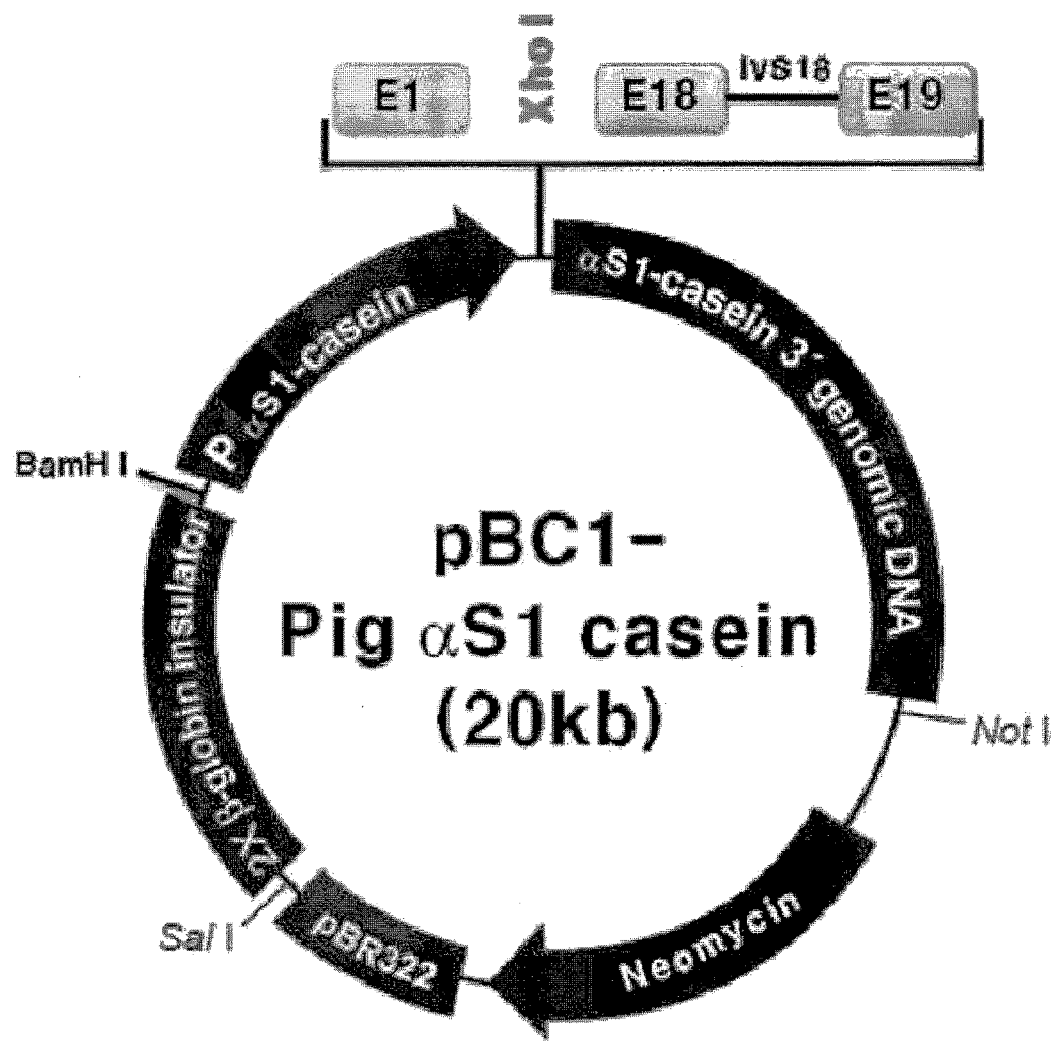
FIG. 2 shows the structure of a pBC1-pig αS1 casein vector according to in accordance with one embodiment of the present invention.

The structure of the constructed pBC1-pig αS1 casein cloning vector is shown in FIG. 2.

In FIG. 2, "P αS1 casein" represents a porcine αS1 casein promoter sequence (SEQ ID NO: 2) containing exon 1 (E1). "Exon 1" refers to an exon which is first arranged in the direction of 5'→3' in the sequence of SEQ ID NO: 1.

In FIG. 2, "αS1-casein 3'genomic DNA" represents a 3' arm sequence (SEQ ID NO: 5) containing exon 18 (E18), exon 19 (E19) and intron 18 (WS 18). "Exon 18" and "exon 19" refer to the $18^{th}$ and $19^{th}$ exons in the direction of 5'→3' in the sequence of SEQ ID NO: 1, respectively.

Due to having an Xho I restriction site, the gene of a target protein can be inserted into the vector.

2Xβ-globin insulator and pBR322 respectively represent the insulator and vector component derived from the pBC1 vector. Neomycin represents a neomycin-resistant gene which is derived from the pEGFP-N1 vector (Clontech, USA).

The thus-constructed pBC1-pig αS1 casein vector was deposited with the Korean Collection for Type Cultures (KCTC), the Korean Research Institute of Bioscience and Biotechnology (KRIBB, Daejon, Korea), under Accession Number KCTC 11324BP.

Example 3: Construction of pBC1-Pig αS1 Casein+hEPO-WPRE Vector

Erythropoietin (hEPO) was cloned into a vector having substitution of an ampicillin-resistant gene of a pBC1 vector (Invitrogen, USA) with a neomycin-resistant gene {A 'neo' gene capable of conferring drug resistance to G418 was obtained from a pEGFP-N1 vector (Clontech, USA) by amplification of a 1.9-kb PCR product (SEQ ID NO: 83) using the forward primer 5'-GCGGCCGCGCGCGTCAG-GTGGCAC-3' (SEQ ID NO: 81) and the reverse primer 5'-CGATCGGACGCTCAGTGGAACGAAAACTC-3' (SEQ ID NO: 82), and was then cloned into a pGEM T-easy vector. The 1.9-kb neo gene cloned into the T-vector was digested with restriction endonucleases Not I and Pvu I to prepare an insert. In addition, an amp gene (ampicillin-resistance gene) region of the pBC1 vector was removed by Not I and Pvu I cleavage to prepare a vector. The resulting insert fragment and vector part were ligated to construct a pBC1 vector into which the neo gene (neomycin-resistance gene) was inserted}, followed by replacement of the goat beta-casein promoter region and the 3' genomic DNA region The pBC1 vector was digested with Bam HI and Not I to remove the goat beta-casein promoter region and the 3' genomic DNA region, thereby preparing a vector. In addition, hEPO+WPRE cloned into the pGEM-T vector was digested with Bam HI and Not I to prepare a 2.9-kb insert. The resulting vector and insert were ligated to construct pBC1+hEPO-WPRE. For cloning of the porcine alpha-S1-casein promoter and the 3' arm region into pBC1+hEPO-WPRE, the promoter sequence of 5.4 kb (SEQ ID NO: 3) and the 3' arm sequence of 4.3 kb (SEQ ID NO: 5) were cloned into a pGEM-T vector (Promega, USA) by means of PCR amplification.

The primer sequences used for the PCR amplification of the porcine alpha-S1-casein promoter sequence and the 3' arm sequence are shown in Table 6 below.

TABLE 6

|  | Primer | SEQ ID NO |
| --- | --- | --- |
| Forward promoter for amplification of promoter | 5'-GGATCCGGCTGTCGTTTTGTTATGATT-3' | 70 |
| Reverse promoter for amplification of promoter | 5'-GGATCCAACTAAAAGGCACAGGGAACT-3' | 71 |
| Forward promoter for amplification of 3' arm | 5'-GCGGCCGCTTACAATTCAGTGTGGGGAAT-3' | 72 |
| Reverse promoter for amplification of 3' arm | 5'-GCGGCCGCCAGCTTTATTACAGGCAGAGG-3' | 73 | present in the vector with a porcine alpha-S1-casein promoter sequence (SEQ ID NO: 3) and a 3' arm sequence (SEQ ID NO: 5). In addition, expression of hEPO was maximized by adding to a 3' end of hEPO, WPRE (woodchuck hepatitis virus post-transcriptional regulatory element) which is known to augment protein expression through stabilization of mRNA.

hEPO and WPRE were each subjected to PCR amplification (PT-200, BIO-RAD). PCR was carried out as follows: denaturation at 94° C. for 5 minutes; and 35 cycles of denaturation at 94° C. for 30 seconds, primer annealing at 56° C. for 30 seconds, and elongation at 72° C. for 2.5 minutes for hEPO and 30 seconds for WPRE. Each of the resulting PCR products 2.3 kb (SEQ ID NO: 69) and 0.6 kb (SEQ ID NO: 70) was cloned into a pGEM-T vector (Promega, USA), followed by confirmation of the sequence thereof. The pGEM-T vector harboring hEPO was digested with Eco RV and Not I, and the pGEM-T vector harboring WPRE was digested with Eco RV and Not I. The resulting two restriction fragments were ligated.

Primer sequences used for the PCR amplification of hEPO and WPRE are shown in Table 5 below.

Point mutations were introduced into two Bam HI sites (GGATCC) present on the porcine alpha-S1-casein promoter sequence, by a Site-Directed Mutagenesis kit (iNtRON) using primers (SEQ ID NO: 60 to SEQ ID NO: 63). The pBC1+hEPO-WPRE vector was digested with Bam HI, and treated with alkaline phosphatase (CIP) for 30 minutes to prepare a vector. In addition, the pGEM-T vector containing the point-mutated porcine alpha-S1-casein 5' promoter DNA was digested with Bam HI to prepare a 5.5-kb insert (SEQ ID NO: 3). The resulting two restriction fragments were ligated to clone a pBC1-pig αS1 casein 5'+EPO-WPRE vector. The pBC1-pig αS1 casein 5'+EPO-WPRE vector was digested with Not I and treated with CIP for 30 minutes to prepare a vector. In addition, the pGEM-T vector containing the 3' arm DNA was digested with Not I to prepare a 4.3-kb insert (SEQ ID NO: 5). The resulting two restriction fragments were ligated to construct a pBC1-pig αS1 casein+hEPO-WPRE vector.

Figure 3:
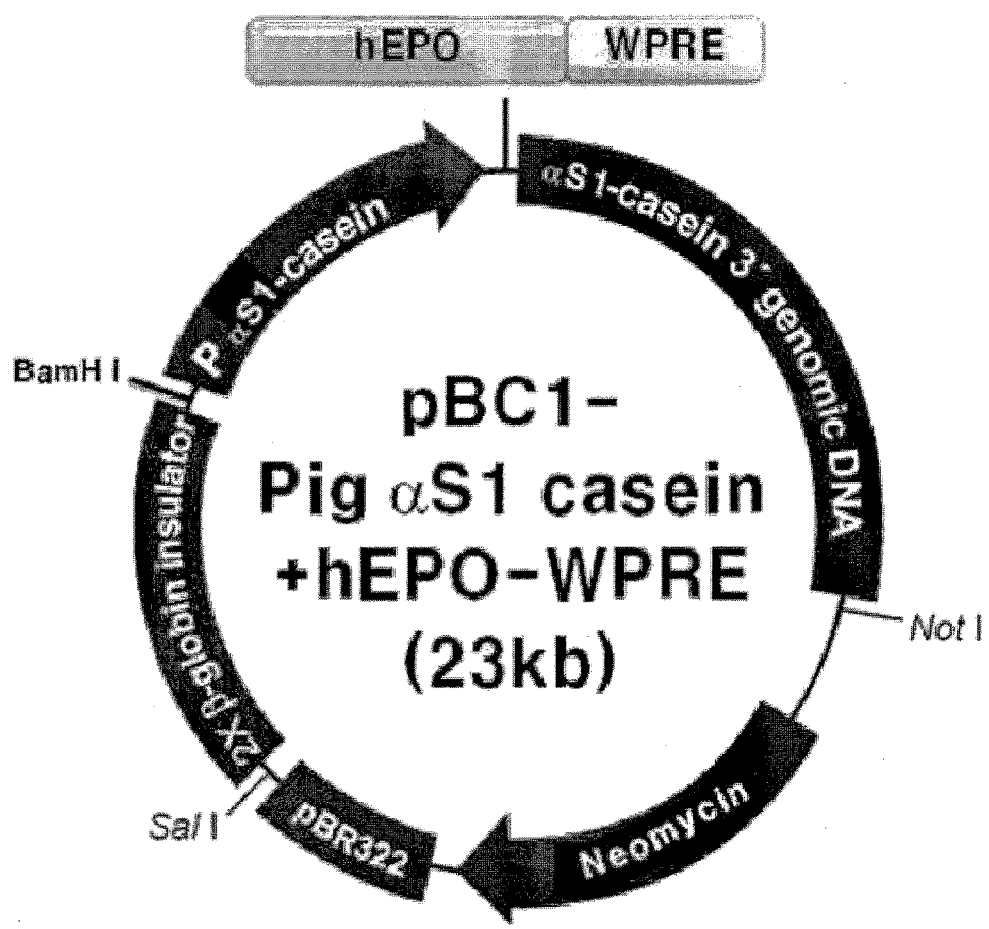
FIG. 3 shows the structure of a pBC1-pig αS1 casein+hEPO-WPRE vector in accordance with one embodiment of the present invention.

The structure of the constructed pBC1-pig αS1 casein+hEPO-WPRE vector is shown in FIG. 3.

TABLE 5

|  | Primer | SEQ ID NO |
| --- | --- | --- |
| Forward primer for amplification of hEPO | 5'-GGATCCTGTGGTCACCCGGCGCGC-3' | 64 |
| Reverse primer for amplification of hEPO | 5'-GATATCCCATGGGACAGGCTGGCGCT-3' | 65 |
| Forward primer for amplification of WPRE | 5'-GATATCTCTGTTCCTGTTAATCAACCTC-3' | 66 |
| Reverse primer for amplification of WPRE | 5'-GCGGCCGCGAGCCCGAGGCGAAACAG-3' | 67 |

In FIG. 3, P αS1 casein represents a porcine αS1 casein promoter sequence (SEQ ID NO: 3), and αS1-casein genomic DNA represents a 3' arm sequence (SEQ ID NO: 6).

hEPO represents a human EPO gene, and WPRE represents a woodchuck hepatitis virus post-transcriptional regulatory element gene.

2Xβ-globin insulator and pBR322 represent the insulator and vector component derived from the pBC1 vector, respectively. Neomycin represents a neomycin-resistant gene derived from the pEGFP-N1 vector (Clontech, USA).

The thus-constructed pBC1-pig αS1 casein+hEPO-WPRE vector was deposited with the Korean Collection for Type Cultures (KCTC), the Korean Research Institute of Bioscience and Biotechnology (KRIBB, Daejon, Korea), under Accession Number KCTC 11325BP.

primary PCR amplification (PT-200, BIO-RAD) was carried out from the human genomic DNA (Cho-A Pharm Co., Ltd.; a pBC1-hEPO vector of Korean Patent No. 10-0769291) under the following conditions: denaturation at 94° C. for 5 min; and then 30 cycles of denaturation at 94° C. for 30 sec, primer annealing at 56° C. for 30 sec and extension at 72° C. for 2.5 min. Then, secondary PCR amplification (PT-200, BIO-RAD) was performed using the primary PCR products as templates under the following conditions: denaturation at 94° C. for 5 min; and then 30 cycles of denaturation at 94° C. for 30 sec, primer annealing at 56° C. for 30 sec and extension at 72° C. for 2.5 min.

The PCR-amplification product 2.3 kb hEPO gene (SEQ ID NO: 68) containing the sequence spanning from the porcine alpha-S1-casein exon 2 region to the initiation codon was cloned into a pGEM-T vector (Promega, USA).

Figure 7:
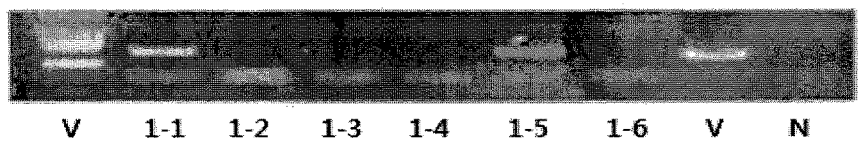
FIG. 7 shows the results of PCR performed to identify transformation in the offspring of mice transformed with a pBC1-pig αS1 casein+hEPO-WPRE according to one embodiment of the present invention.
Figure 7:
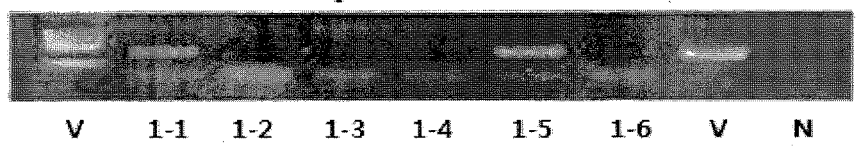

Primer sequences used for the PCR amplification of hEPO are shown in FIG. 7 below.

TABLE 7

| Primer | | SEQ ID NO |
|---|---|---|
| Primary forward primer for amplification of hEPO | 5'-GTGTTGACAACCATGGGGGTGCACGGTGAGTACTC-3' | 74 |
| Secondary forward primer for amplification of hEPO | 5'-GATATCTTTTCTTATATAGGTGTTGACAACCATGGGGG-3' | 75 |
| Reverse primer for amplification of hEPO | 5'-GAATTCATGGGACAGGCTGGCGCTGA-3' | 76 |

Example 4: Construction of Pig αS1 Casein-hEPO Knock-In Vector Using Porcine Alpha-S1-Casein Gene 1) Cloning of pGEM-T-hEPO Vector For construction of a porcine alpha-S1-casein hEPO knock-in vector capable of confirming correct introduction of a gene into a specific site by TK gene selection, two pairs of specific primers (SEQ ID NO: 74 to 76) were prepared which contain from the beginning of an exon 2 region to an initiation codon in the porcine alpha-S1-casein gene and enables amplification of a sequence of the hEPO gene from after the initiation codon. With the above-prepared primers containing the exon 2 region of porcine alpha-S1-casein, 2) Construction of pGEM-T-Pig αS1 Casein 5'Arm and pGEM-T-Pig αS1 Casein 3'Arm In order to clone the promoter sequence (5' arm) and 3' arm sequence (3' arm) of the porcine alpha-S1-casein gene, primers of SEQ ID NO: 77 to SEQ ID NO: 80 were constructed, and PCR amplification was then carried out from the porcine genomic DNA using the constructed primers. The resulting PCR products 5.0 kb (SEQ ID NO: 4) and 4.9 kb (SEQ ID NO: 6) were cloned into a pGEM-T vector to thereby construct pGEM-T-pig αS1 casein 5' arm and pGEM-T-pig αS1 casein 3' arm.

TABLE 8

| Primer | | SEQ ID NO |
|---|---|---|
| Forward primer of amplification of promoter | 5'-GTCGACAGCTGCAATGAACATGTGGGTG-3' | 77 |
| Reverse primer of amplification of promoter | 5'-GATATCCAAAATAAAAATTTAGGTCTGACAG-3' | 78 |
| Forward primer of amplification of 3' arm | 5'-GCGGCCGCATGGCATATGGAAGTTCCCAGG-3' | 79 |
| Reverse primer of amplification of 3' arm | 5'-CCGCGGTGGGAACTTCCATATGCCAT-3' | 80 |

3) Construction of Lox A Neo-hEPO Vector

A Lox A neo vector (Gerard Karsenty's, Department of Genetics and Development, College of Physicians and Surgeons, Columbia University, New York, N.Y. 10032) was restricted with the restriction enzymes Eco RV and Eco RI to prepare a vector. In addition, the cloned pGEM-T-hEPO was restricted with the restriction enzymes Eco RV and Eco RI to prepare a 2.3-kb insert (SEQ ID NO: 68). The resulting two restriction fragments were ligated to construct a Lox A neo-hEPO vector.

4) Construction of Lox a Neo-hEPO-polyA Vector

In order to insert a poly A sequence for stabilization of RNA into the 3' end of the Lox A neo-hEPO vector, the Lox A neo-hEPO vector was restricted with the restriction enzyme Eco RI and treated with alkaline phosphatase (New England Biolabs (NEB), USA) for 30 minutes to prepare a vector. In addition, the bovine growth hormone (BGH) poly A derived from a pcDNA3 vector (Invitrogen, USA) was restricted with the restriction enzyme Eco RI to prepare a 0.3-kb insert. The two prepared fragments were ligated to construct a Lox A neo-hEPO-poly A vector.

5) Construction of Lox A Neo-hEPO-Poly A-5' Arm Vector

In order to insert a porcine alpha-S1-casein 5' arm into the 5' end of the Lox A neo-hEPO-poly A vector, the Lox A neo-hEPO-poly A vector was restricted with the restriction enzymes Sal I and Eco RV (New England Biolabs (NEB), USA) to prepare a vector. In addition, the cloned pGEM-T-pig αS1 casein 5' arm vector was restricted with the restriction enzymes Sal I and Eco RV to prepare a 5.0-kb insert (SEQ ID NO: 4. The resulting two restriction fragments were ligated to construct a Lox A neo-hEPO-poly A-5' arm vector.

6) Construction of Lox A Neo-hEPO-PolyA-5' Arm-3' Arm Vector

In order to insert a porcine alpha-S1-casein 3' arm into the 3' end of the Lox A neo-hEPO-poly A-5' arm vector, the Lox A neo-hEPO-polyA-5' arm vector was restricted with the restriction enzyme Not I (New England Biolabs (NEB), USA) and treated with alkaline phosphatase for 30 minutes to construct a vector. In addition, the cloned pGEM-T-pig αS1 casein 3' arm vector was restricted with the restriction enzyme Not I to prepare a 4.9-kb insert (SEQ ID NO: 6). The resulting two restriction fragments were ligated to construct a Lox A neo-hEPO-poly A-5' arm-3' arm vector.

7) Construction of Lox A Neo-hEPO-Poly A-5' Arm-3' Arm-TK Vector

In order to insert a Herpes simplex virus-thymidine kinase (HSV-tk) gene as an apoptotic gene into the 3' end of the Lox A neo-hEPO-poly A-5' arm-3' arm vector, the Lox A neo-hEPO-poly A-5' arm-3' arm vector was restricted with the restriction enzyme Sac II (New England Biolabs (NEB), USA) and treated with alkaline phosphatase for 30 minutes to prepare a vector. A pBS-TK vector (Gerard Karsenty's, Department of Genetics and Development, College of Physicians and Surgeons, Columbia University, New York, N.Y. 10032) was restricted with the restriction enzyme Not I to prepare a 2.3-kb insert (encoding the Herpes simplex virus-thymidine kinase gene). The resulting two restriction fragments were ligated to construct a Lox A neo-hEPO-polyA-5' arm-3' arm-TK vector (Pig αS1 casein-hEPO knock-in vector).

Figure 4:
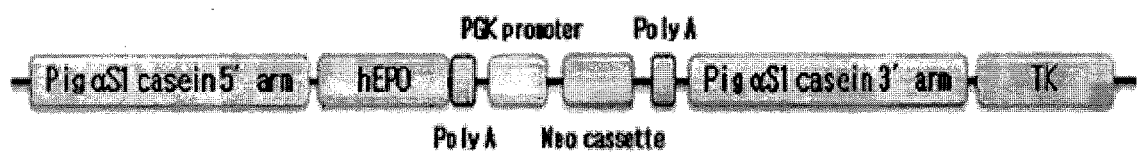
FIG. 4 shows the structure of a Pig αS1 casein-hEPO knock-in vector in accordance with one embodiment of the present invention.

The structure of the constructed Pig αS1 casein-hEPO knock-in vector is shown in FIG. 4. In FIG. 4, Pig αS1 casein 5' arm represents the porcine αS1 casein promoter (SEQ ID NO: 4), and Pig αS1 casein 3' arm represents the 3' arm (SEQ ID NO: 6).

hEPO represents a human EPO gene, poly A represents a poly A signal-encoding gene, Neo cassette represents a neomycin-resistant gene which serves as a positive selective gene, PGK promoter represents a phosphoglycerate kinase (PGK) promoter, and TK represents a Herpes simplex virus-thymidine kinase (HSV-tk) gene which serves as a negative selective gene and is derived from the pBS-TK vector.

The thus-constructed Pig αS1 casein-hEPO knock-in vector was deposited with the Korean Collection for Type Cultures (KCTC), the Korean Research Institute of Bioscience and Biotechnology (KRIBB, Daejon, Korea), under Accession Number KCTC 11326BP.

Example 5: Preparation of Transformed Cell Line and Identification of Expression of hEPO 1) Exogenous Gene Transfection Mammary mouse cells (HC11, National Institute of Animal Science, Korea), mouse muscle cells (C2C12, ATCC, USA), human hepatoma cells (HepG2, ATCC, USA), human kidney cells (Caki, ATCC, USA), human leukemia cells (U937, ATCC, USA), rat brain glioma cells (C6, ATCC, USA) and the like were cultured in incubators under the following conditions:

HC11-RPMI 1640 (Gibco, USA), 10% Fetal Bovine Serum (FBS, HyClone, USA), 1% penicillin streptomycin (HyClone, USA), 5 µg/ml insulin (Sigma, USA), 39° C., 5% $CO_2$;

C2C12 and HepG2-DMEM (Gibco, USA), 10% FBS, 1% penicillin streptomycin, 37' C., 5% $CO_2$;

Caki-McCoy's 5A (Gibco, USA), 10% FBS, 1% penicillin streptomycin, 37° C., 5% $CO_2$;

U937-RPMI 1640 (Gibco, USA), 10% FBS, 1% penicillin streptomycin, 37° C., 5% $CO_2$.

Each of the cell lines grown to a confluence of about 80-90% was detached from the cell culture dish using trypsin (HyClone), and then centrifuged at 1500 rpm for 5 minutes, followed by removal of the supernatant. The cells were counted with a Hemocytometer (Reichert, USA), and then cultured in 60-mm culture dishes in an incubator at a density of $5 \times 10^5$ cells/dish for 16-20 hours. Transfection of an exogenous gene was performed by introducing 4 µg of each of the vectors, prepared in Examples 2 and 3, into each of the 60-mm culture dishes using lipofectamine (Invitrogen, USA). In the case of the HC 11 cell line, 4 hours after the exogenous gene transfection, 5 µg/ml of insulin (Sigma, USA), 5 µg/ml of prolactin (Sigma, USA) and 5 µg/ml of hydrocortisone (Sigma, USA) were added to the cells.

2) Reverse Transcription (RT)

24 hours after the exogenous gene transfection, RNA was purified from the cells using an easy-BLUE total RNA Extraction Solution (iNtRON Biotechnology, Korea). Using 4 µg of the purified RNA, and superscript III reverse transcriptase (Invitrogen, USA), reverse transcription was performed. Herein, in order to prevent the contamination of DNA introduced as the exogenous gene, treatment with DNase I was performed. In the reverse transcriptase, 1 µl of 10 pM oligo dT and 1 µl of 10 mM dNTPs were added to the RNA and then allowed to react at 65° C. for 5 minutes, followed by reaction on ice for 1 minute. Next, 4 µl of 5× buffer, 1 µl of 0.1 M DTT and 1 µl of reverse transcriptase were added thereto, and then allowed to react at 50° C. for 60 minutes, followed by reaction at 70° C. for 15 minutes, thereby synthesizing cDNA.

3) Real-Time PCR

Using a highly sensitivity real-time PCR assay, the expression of EPO in each of cell line was analyzed. Real-time PCR was performed using cDNA (prepared using reverse transcriptase) with SYBR Green qPCR kit (FINNZYMES, Finland) and DNA engine Opticon 2 (BIO-RAD, USA) under the following conditions: denaturation at 94° C. for 5 min; and then 50 cycles of denaturation at 94° C. for 30 sec, primer annealing at 56° C. for 30 sec, and extension at 72° C. for 60 sec, followed by measurement of fluorescence. The fluorescence values were corrected with respect to the Neo gene of the vector and the beta actin gene of the cell. The results of the real-time PCR were analyzed using GeneExMacro 3.0 (BIO-RAD) program. The primers (SEQ ID NO: 84 to SEQ ID NO: 91) used for the above PCE amplification are shown in Table 9 below.

TABLE 9

| Primer | | SEQ ID NO |
|---|---|---|
| Forward primer for amplification of EPO | 5'-CAAGGAGGCCGAGAATATCA-3' | 84 |
| Reverse primer for amplification of EPO | 5'-AAGTGTCAGCAGTGATTGTTCG-3' | 85 |
| Forward primer for amplification of Neo | 5'-GCTACCCGTGATATTGCTGAA-3' | 86 |
| Reverse primer for amplification of Neo | 5'-CAACACCGTGCGTTTTATTCT-3' | 87 |
| Forward primer for amplification of human beta actin | 5'-CGTGGGCCGCCCTAGGCACCA-3' | 88 |
| Reverse primer for amplification of human beta actin | 5'-TTGGCCTTAGGGTTCAGGGGGG-3' | 89 |
| Forward primer for amplification of mouse beta actin | 5'-TGTGATGGTGGGAATGGGTCAG-3' | 90 |
| Reverse primer for amplification of mouse beta actin | 5'-TTTGATGTCACGCACGATTTTCC-3' | 91 |

Figure 5:
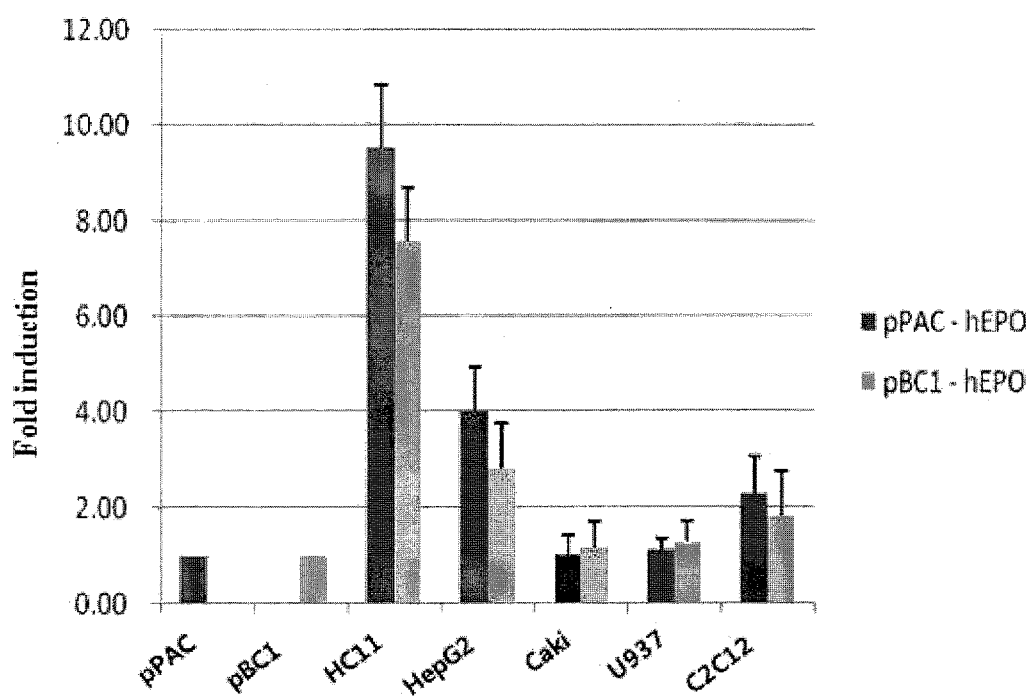
FIG. 5 is a graphic diagram showing the results of expression of hEPO in a cell line transfected with a Pig αS1 casein+hEPO-WPRE vector according to one embodiment of the present invention.

The results of the real-time PCR are shown in FIG. 5.

FIG. 5 shows the results of expression of hEPO in the mammary gland cell line and other tissue cell lines, transfected with the pBC1-pig αS1 casein vector and the pBC1-pig αS1 casein+hEPO-WPRE vector. As control, a pBC1 vector (Invitrogen) and a pBC1-hEPO-WPRE vector (Cho-A Pharm Co., Ltd.; Korean Patent No. 10-0769291) were introduced into the same cells. In FIG. 5, the x-axis indicates the cell lines, and the y-axis indicates the ratio of the expression of hEPO relative to the expression of each of the pBC1-pig αS1 casein and pBC1 vectors taken as 1. In FIG. 5, pPAC indicates the pBC1-pig αS1 casein vector of Example 2, and pPAC-hEPO indicates the pBC1-pig αS1 casein+hEPO-WPRE vector. In addition, pBC1 indicates an Invitrogen's vector which has a goat promoter and permits mammary gland-specific expression, and pBC1-hEPO indicates pBC1-hEPO-WPRE.

As can be seen in FIG. 5, hEPO was most highly expressed in the mouse mammary gland cell line HC11, was weakly expressed in the human hepatoma cell line HepG2 and the mouse muscle cell line C2C12 and was not expressed in other tissue cells. This suggests that a target protein can be produced in mammary gland cells transformed with the vector of the present invention.

Example 6: Preparation of Animal Embryo by Microinjection, Construction of Transgenic Animal Using the Animal Embryo and Production of EPO in the Transgenic Animal 1) Purification of Gene The vector prepared in Example was linearized with SaII (NEB, R0138), and DNA was purified from the linearized vector using a QIAquick Gel Extraction kit (Q-28706) and eluted in injection buffer (10 mM Tris-HCl, 0.1 mM EDTA, pH 7.4) at a final concentration of 2 ng/μl. Aliquots of 5 μl were stored at −20° C.

2) Collection of Fertilized Embryos from Superovulated Male Mice 8-week-old C57BL/6 female mice (Orient Bio, Korea) were induced to superovulate by intraperitoneal injection of 5 IU of pregnant mare serum gonadotropin (PM SG; Intervet, Netherlands) followed 46-hour later by 5 IU of human chorionic gonadotropin (hCG, Intervet). Light was controlled at a 12-hr cycle from 7 AM to 7 PM, and PMSG and hCG were intraperitoneally injected at 11 AM and 9 AM, respectively. After the injection of hCG, the mice were mated with males of the same strain. The female mice were inspected for vaginal plugs the next day as an indication of successful mating, followed by oviduct excision. To separate oocytes from cumulus cells, the excised oviducts were transferred to M2 medium (Sigma, M7167) containing 0.1% hyaluronidase (Sigma, H3884), and then the ampulla was ruptured. After a while, only embryos from which cumulus cells had been excluded were collected, washed in fresh M2 medium, transferred into M16 medium (Sigma, M7292), and incubated in a 5% CO) incubator until for microinjection.

3) Microinjection of Gene

A small amount of M2 medium was dropped on chamber slides (Nunclon, Denmark) which were then covered with oil in order to prevent evaporation, thereby preparing dishes for microinjection. Then, the collected embryos were placed on the dishes. Microinjection of the embryos was carried out in an OLYMPUS 1X71 TH4-200 inverted microscope which is a system for micromanipulation of embryos. Using a microloader (Eppendorf, Hamburg, Germany), the purified gene prepared in the above section 1) was loaded into a Femtotip injection pipette (Eppendorf) connected to a Femtojet automatic injector (Eppendorf). To prepare microinjection, the embryos were pulled to a holding pipette by negative pressure, and the microscope was focused to locate the pronuclei. When the tip of the pipette appeared to be inside the pronucleus, the injection pressure was applied through the Femtojet automatic injector. If the swelling of pronucleus was visible, the injection pipette was withdrawn from the egg. After microinjection, survived eggs were transferred into M16 medium and cultured in a 5% $CO_2$ incubator at 37° C.

4) Transfer of Embryos

One day before microinjection, 6-week-old female BDF-1 mice (Orient Bio, Korea) were mated with castrated males of the same strain to elicit pseudopregnancy. Before the experiment, the female mice were checked for vaginal plugs to confirm pseudopregnancy. Female mice whose pseudopregnancy was induced were anesthetized by intraperitoneal injection of avertin (Sigma), and then the portion between the flank and the leg attached to the chest was incised, and ovarian fat was pulled to extract the ovary and the oviduct. The ovarian fat was fixed with surgical forceps, the cyst surrounding the ovary and the oviduct was ruptured, and a transfer pipette was inserted into the entrance of the oviduct, thereby transferring the eggs. Herein, the embryos were transferred into both oviducts. The transfer pipette used herein consisted of 4 marker bubbles for confirmation of transfer, 15 microinjection embryos and a final marker bubble.

5) Examination of Gene Transfection

When offspring were born 3 weeks after embryo transfer, the tail of the offspring was cut, and genomic DNA was extracted therefrom using a Dneasy Blood&Tissue kit (Qiagen, Q-69506). In order to identify transgenic mice transfected with the porcine alpha-S1-casein gene, using primers amplifying the EPO-WPRE gene region and WPRE-3' arm gene region of the extracted DNA, PCR amplification ((PT-200, BIO-RAD) was performed under the following conditions: denaturation at 94° C. for 5 min; and then 35 cycles of denaturation at 94° C. for 30 sec, primer annealing at 55° C. for 30 sec and extension at 72° C. for 30 sec. In this way, the transfection of the porcine alpha-S1-casein gene was identified.

The sequences of the primers used for PCR amplification of EPO-WPRE and WPRE-3' arm are shown in Table 10 below.

TABLE 10

| Primer | | SEQ ID NO |
|---|---|---|
| Forward primer for amplification of EPO-WPRE | 5'-AACTCTTCCGAGTCTACTCCA-3' | 92 |
| Reverse primer for amplification of EPO-WPRE | 5'-CTCCTCATAAAGAGACAGCAAC-3' | 93 |
| Forward primer for amplification of WPRE-3' arm | 5'-TTCCTGTTAATCAACCTCTGG-3' | 94 |
| Reverse primer for amplification of WPRE-3' arm | 5'-TACCAAAGGCCATAATTGTGG-3' | 95 |

Figure 6:
FIG. 6 shows the results of PCR performed to select mice transformed with a pBC1-pig αS1 casein+hEPO-WPRE vector according to one embodiment of the present invention.
Figure 6:
Figure 6:
Figure 6:
Figure 6:
Figure 6:
Figure 6:
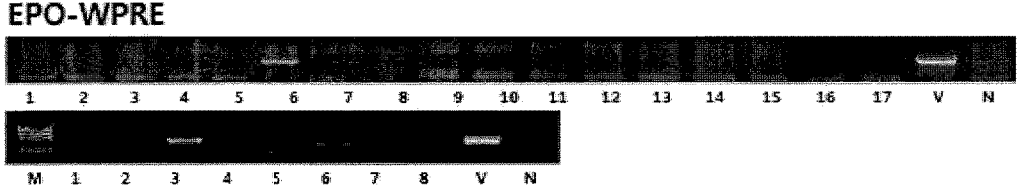
Figure 6:
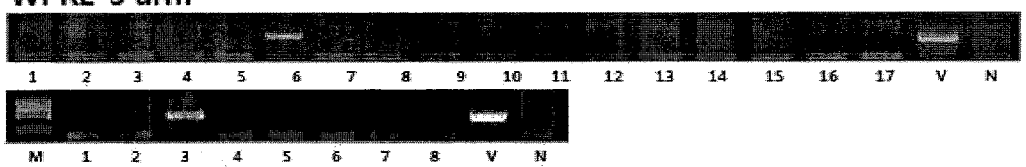

The results of the PCR amplification are shown in FIG. 6. FIG. 6 shows the results of PCR performed to select mice transformed with the expression vector pBC1-pig alpha S1 casein+hEPO-WPRE of Example 3. In FIG. 6, EPO-WPRE indicates the results for the EPO-WPRE gene region, and WPRE-3'arm indicates the results for EPO-alpha S1 3'arm-.gene region. "M" indicates a size marker, "V" indicates the pBC1-pig-alpha S1 casein-EPO-WPRE vector, "N" indicates normal mouse genomic DNA for negative control, and numerals indicate individuals.

Based on the above results, whether the gene was introduced was determined, thereby selecting transgenic mice.

6) Examination of Reproduction of Transgenic Experimental Animals and Gene Transfer Among the transgenic mice confirmed to be transfected with the porcine alpha-S1-casein gene, the females were mated with normal males after 6 weeks (reached sexual maturity) to produce offspring. The offspring were examined for transfection of the exogenous gene in the same manner as the above section 5).

FIG. 7 shows the results of PCR performed to select mice transformed with the expression vector pBC1-pig alpha S1 casein+hEPO-WPRE of Example 3. In FIG. 7, EPO-WPRE indicates the results for the EPO-WPRE gene region, and WPRE-alpha S1 indicates the results for the EPO-alpha S1 3' arm gene region. "M" indicates a size marker, "V" indicates the pBC1-pig-alpha S1 casein-EPO-WPRE vector, "N" indicates normal mouse genomic DNA for negative control, and "1-1" to "1-6" indicate offspring of the transgenic mice.

7) Analysis of Presence and Content of EOP in Transgenic Lactating Mice 7 days after lactation, the offspring were isolated, and 2 hours, the lactating mice were injected intraperitoneally with 10 IU of oxycotin. Then, milk was collected from the lactating mice while massaging the mammary gland. The collected milk was subjected to a Western blot assay. For this purpose, the milk was loaded on 12% SDS-PAGE gel which was then transferred to a PVDF membrane (Millipore, USA), followed by incubation in 5% skim milk blocking solution. Anti-human EPO antibody (1:1,000, hEPO anti-rabbit antibody, R&D systems Cat. No. AB-286-NA, Lot No. HX01, USA) was added to the membrane according to the manufacturer's protocol, followed by incubation at room temperature for 1 hour. Then, the membrane was washed with TBST buffer (Tris buffered saline buffer, 0.01% tween-20) for 30 minutes, and then peroxidase-labeled anti-rabbit antibody (1:3,000; GE healthcare, Cat. No. NA9340V, Lot No. 348424, GB) was added thereto, followed by incubation at room temperature for 1 hour. Next, the membrane was washed with TBST buffer and then exposed to an X-ray film.

Figure 8:
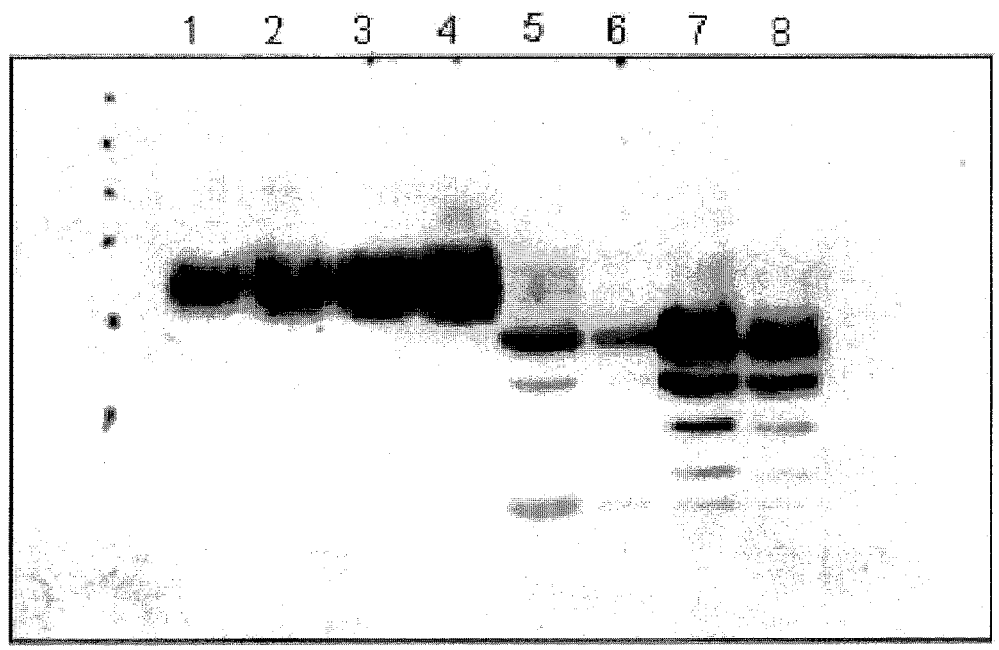
FIG. 8 shows the results of a Western blot assay performed using milk of transgenic mice according to one embodiment of the present invention.

The results of the Western blot assay are shown in FIG. 8. FIG. 8 shows the results of the Western blot assay carried out using the milk of the transgenic lactating mice. In FIG. 8, "1 to 4" indicates an EPO standard (Calbiochem, USA), and 5 and 6 indicate the milk sample.

As a result, it was observed that a protein having a molecular weight of 32 KDa was expressed in the milk.

In addition, in order to determine the concentration of hEPO in the milk of the lactating mice, ELISA (Enzyme-linked immunosorbent assay) was performed using an ELISA kit (Stem Cell Technology) according to the manufacturer's instruction. As a result, it was found that hEPO was expressed in the milk at a concentration of 50,000-200,000 IU/ml.

INDUSTRIAL APPLICABILITY

As apparent from the above description, the porcine alpha-S1-casein gene of the present invention can be used for the production of porcine alpha-S1-casein, and the porcine alpha-S1-casein gene promoter promotes the mammary gland-specific expression of a target proteins. Accordingly, a transgenic animal transformed with an expression vector employing the promoter of the present invention same allow for high-concentration secretion of target proteins in milk, which consequently will provide benefits for the production of useful proteins that are medically and pharmaceutically valuable.

What is claimed is:

1. An expression vector, comprising:
   a) one or more sequences of nucleotides that comprise a promoter and that are selected from among the sequences set forth as SEQ ID NO: 2, SEQ ID NO: 3 and SEQ ID NO: 4, wherein:
   the one or more sequences of nucleotides that comprise a promoter is operatively linked for expression to DNA encoding a protein; and
   the protein is heterologous to the promoter; and
   b) one or both sequences of nucleotides set forth as SEQ ID NO: 5 and SEQ ID NO: 6, and located 3' to the DNA encoding the protein.

2. The expression vector of claim 1, wherein the sequence of nucleotides comprising the promoter is set forth as SEQ ID NO: 3 or SEQ ID NO: 4.

3. The expression vector of claim 1, wherein the expression vector additionally comprises one or more elements selected from among a selective marker gene, an insulator, and WPRE (woodchuck hepatitis virus posttranscriptional regulatory element).

4. The expression vector of claim 3, wherein the vector is pBC1-pig αS1 casein.

5. The expression vector of claim 1, wherein the vector additionally comprises a target protein-encoding sequence at a 3 end of the promoter sequence.

6. The expression vector of claim 5, wherein the target protein is human EPO (erythropoietin).

7. The expression vector of claim 6, wherein the vector is pBC1-pig αS1 casein+hEPO-WPRE.

8. The expression vector of claim 1, wherein the vector is a knock-in vector.

9. The expression vector of claim 8, wherein the knock-in vector comprises a selective marker gene.

10. The expression vector of claim 9, wherein the expression vector is Pig αS1 casein-hEPO knock-in.

11. A non-human animal somatic cell, comprising the vector of claim 1.

12. The non-human animal somatic cell of claim 11, wherein the vector is a knock-in vector.

* * * * *